US012606546B2

(12) United States Patent
Wang et al.

(10) Patent No.: US 12,606,546 B2
(45) Date of Patent: Apr. 21, 2026

(54) SMALL MOLECULE INHIBITORS OF CALCIUM CHANNEL ACTIVITY AND USES THEREOF

(71) Applicant: Arizona Board of Regents on Behalf of the University of Arizona, Tucson, AZ (US)

(72) Inventors: Jun Wang, Tucson, AZ (US); Rajesh Khanna, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 18/069,030

(22) Filed: Dec. 20, 2022

(65) Prior Publication Data

US 2023/0365544 A1     Nov. 16, 2023

Related U.S. Application Data

(63) Continuation-in-part of application No. 17/924,863, filed as application No. PCT/US2021/031964 on May 12, 2021.

(Continued)

(51) Int. Cl.
*C07D 409/14* (2006.01)
*A61K 45/06* (2006.01)
(Continued)

(52) U.S. Cl.
CPC ............ *C07D 409/14* (2013.01); *A61K 45/06* (2013.01); *C07D 401/12* (2013.01);
(Continued)

(58) Field of Classification Search
None
See application file for complete search history.

(56) References Cited

FOREIGN PATENT DOCUMENTS

WO     WO-2011068899 A1 *  6/2011   ......... A61K 31/4985

OTHER PUBLICATIONS

Zhang, J., Hu, Y., Foley, C. et al. Exploring Ugi-Azide Four-Component Reaction Products for Broad-Spectrum Influenza Antivirals with a High Genetic Barrier to Drug Resistance. Sci Rep 8, 4653 (2018). doi.org/10.1038/s41598-018-22875-9 (Year: 2018).*

(Continued)

*Primary Examiner* — Jeffrey S Lundgren
*Assistant Examiner* — Anthony Joseph Seitz
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a piperazine or piperidine structure which function as either inhibitors of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx) or specific inhibitors of CaV3.2 voltage gated calcium channel activity, and their use as therapeutics for the treatment and/or prevention of pan-T-type calcium channel related pain (e.g., CaV3.1 related pain) (e.g., CaV3.2 related pain) (e.g., CaV3.3 related pain) (e.g., HIV-associated peripheral sensory neuropathy, chemotherapy-induced peripheral neuropathy (CIPN), spinal nerve ligation (SNL) induced neuropathy) (e.g., tonic, neuropathic, and/or inflammatory pain) and related conditions.

9 Claims, 42 Drawing Sheets

Specification includes a Sequence Listing.

Related U.S. Application Data

(60) Provisional application No. 63/291,828, filed on Dec. 20, 2021, provisional application No. 63/023,672, filed on May 12, 2020.

(51) Int. Cl.

| | |
|---|---|
| *C07D 401/12* | (2006.01) |
| *C07D 401/14* | (2006.01) |
| *C07D 405/12* | (2006.01) |
| *C07D 409/06* | (2006.01) |

(52) U.S. Cl.
CPC ......... *C07D 401/14* (2013.01); *C07D 405/12* (2013.01); *C07D 409/06* (2013.01)

(56) References Cited

OTHER PUBLICATIONS

Stewart et al., J. Org. Chem. 1948, 13, 1, 134-143 (Year: 1948).*
Sarker et al., Mymensingh Med J. Jul. 2007;16(2 Suppl):S7-11 (Year: 2007).*
CAS RN No. 823206-78-6 and CAS RN No. 823206-94-6 (Year: 2005).*

* cited by examiner

FIG. 1A

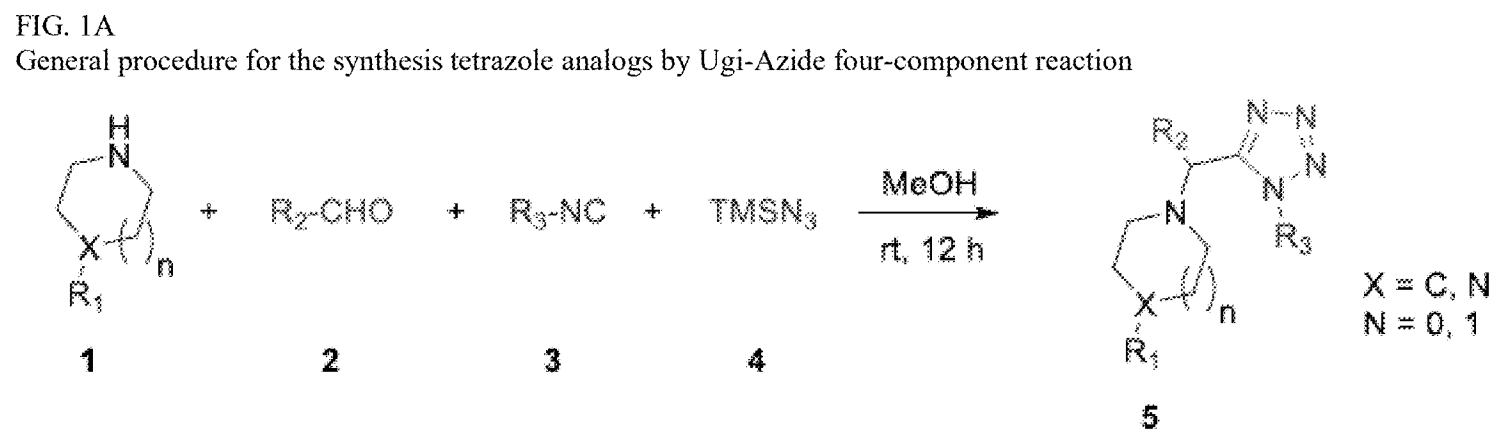

General procedure for the synthesis tetrazole analogs by Ugi-Azide four-component reaction FIG. 1B
List of compounds synthesized and tested in the Ca²⁺ flux assay

A

5bk

Pimozid
antipsychotic drug

Flibanserin
Oral drug for the treatment of
hypoactive sexual desire disorder

Cilostazol
Oral drug for the treatment of
intermittent claudication

DuloxetinOral
Oral antidepressant drug

| M.W. | 485.6 |
|------|-------|
| tPSA | 92.2 |
| cLogP | 4.6 |
| Caco-2 permeability | $105^a$ |
| M.W. = molecular weight; tPSA = total polar surface; cLog = lipophilicity; $^a$ nm/sec | |

FIG. 3A-B
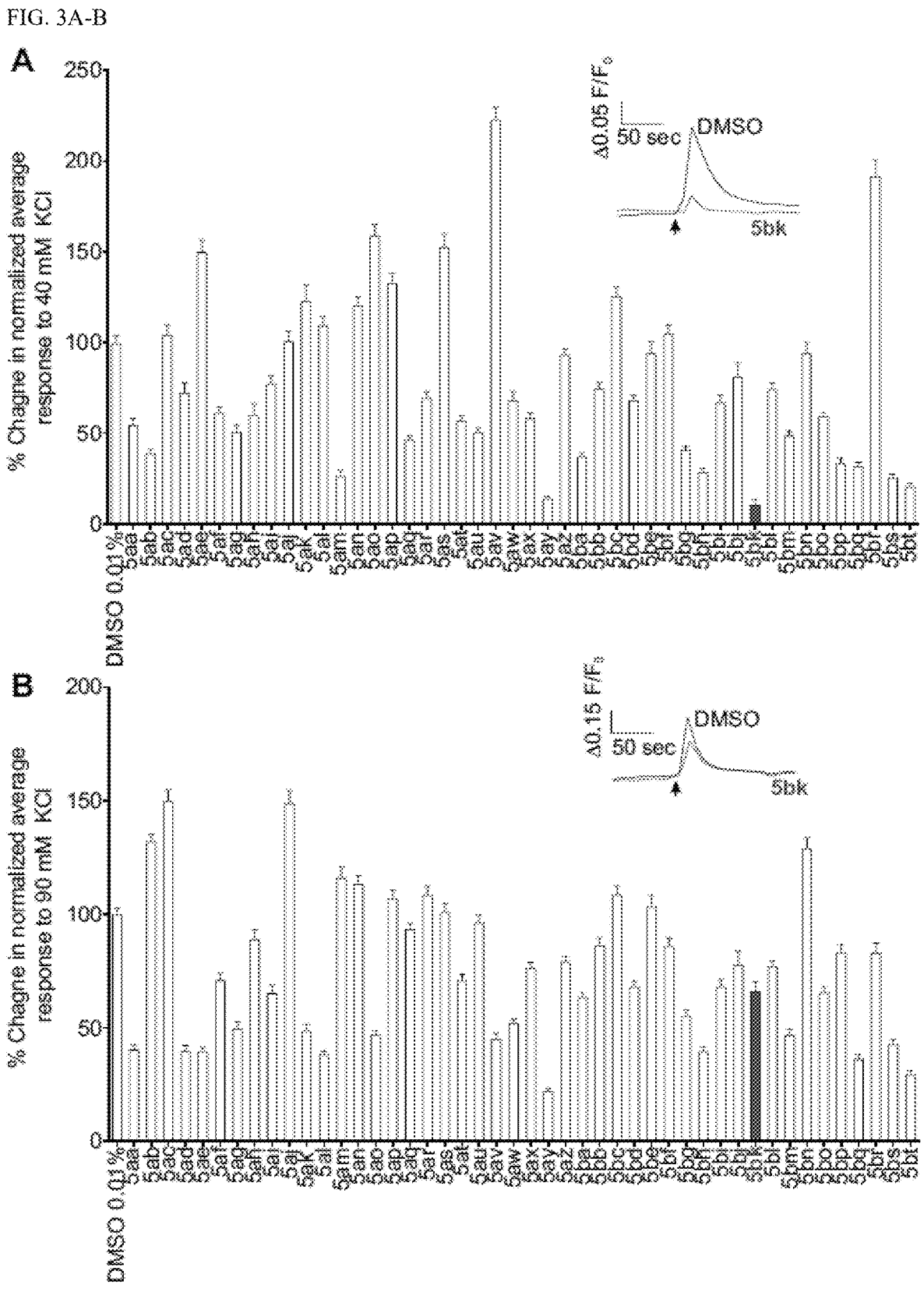

FIG. 3C-D
C
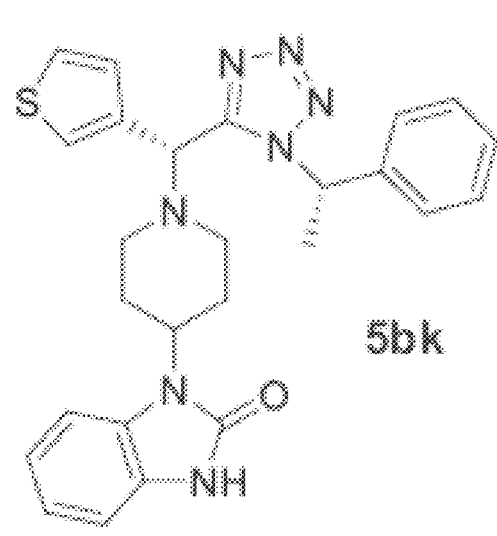
5bk
D
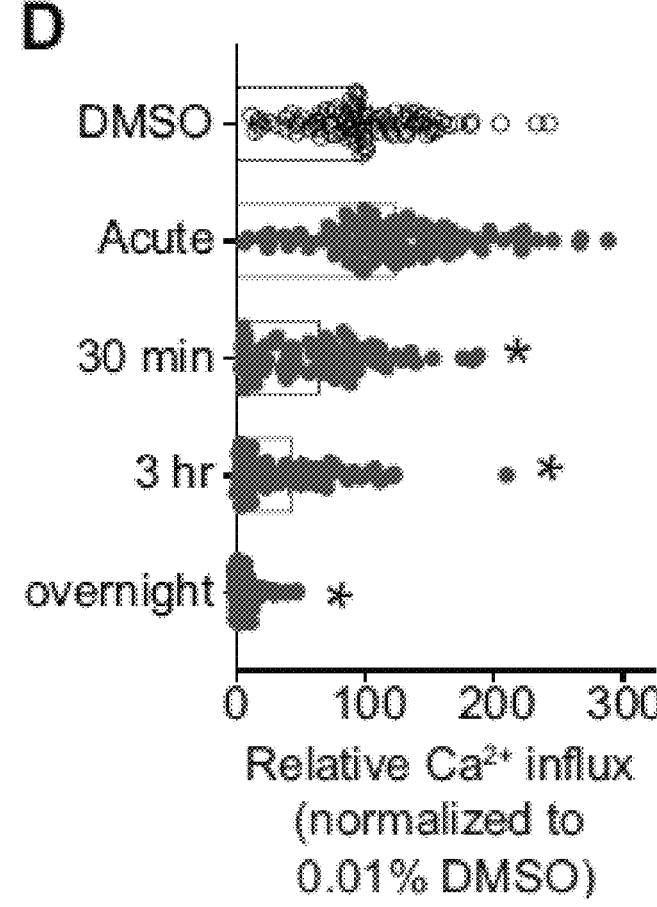
Relative Ca²⁺ influx
(normalized to
0.01% DMSO)

FIG. 4A-F
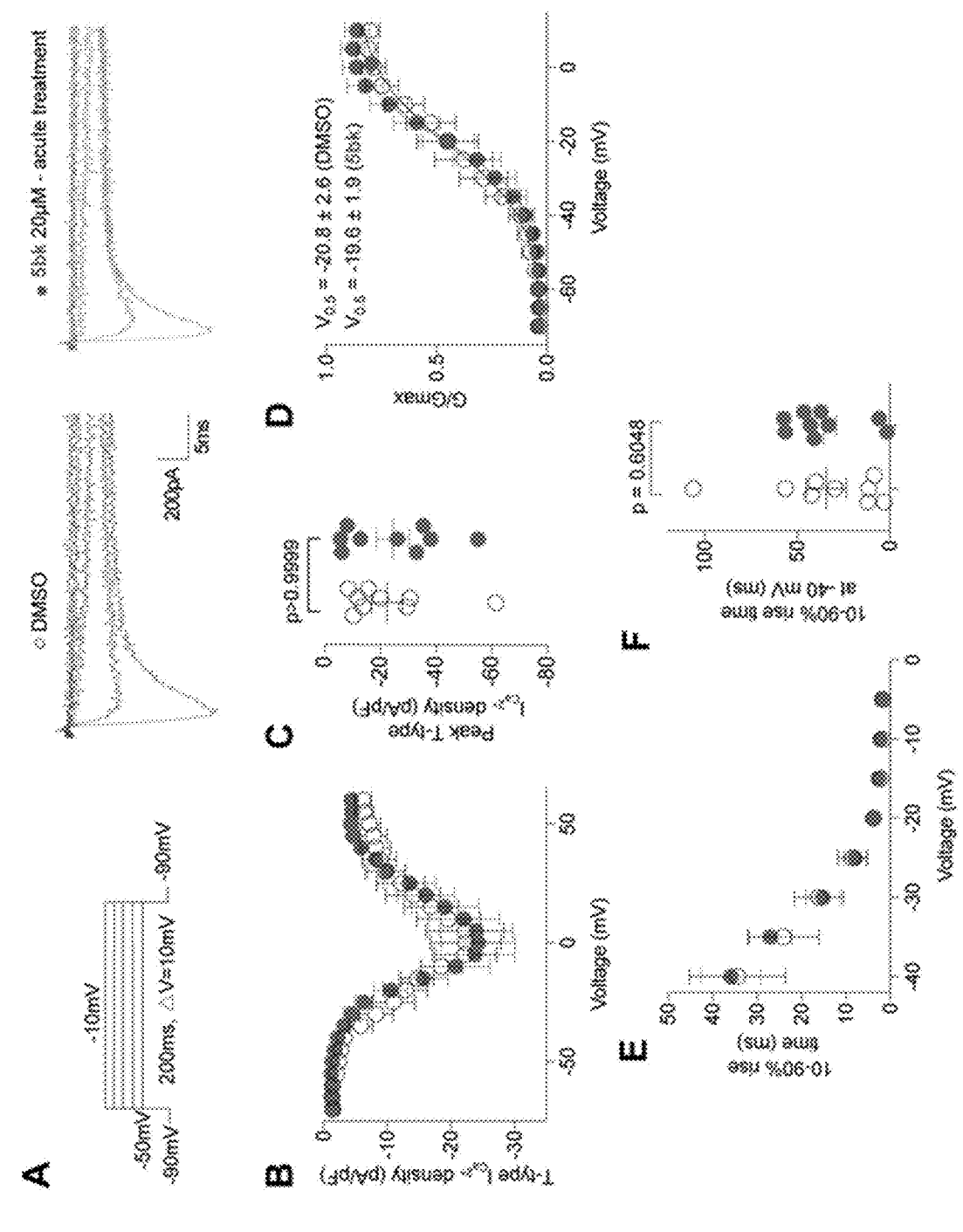

FIG. 4G-I
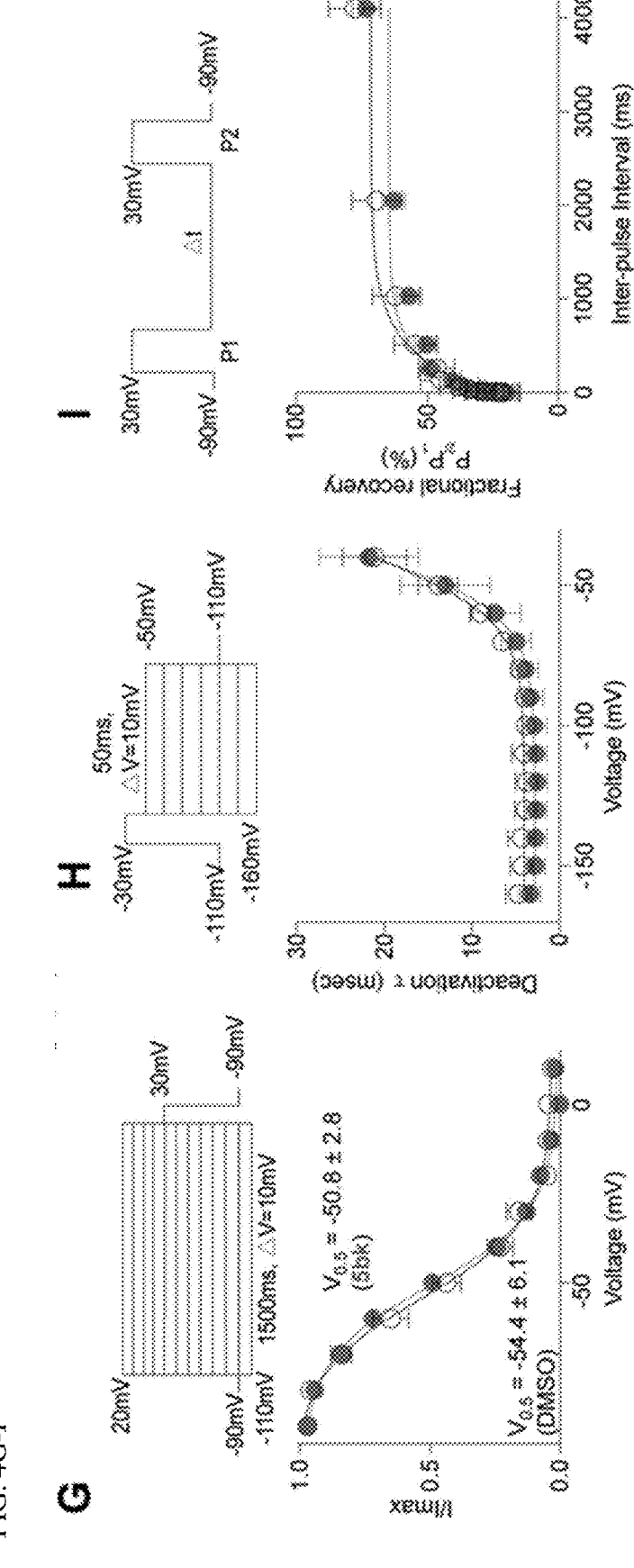

FIG. 5A-H
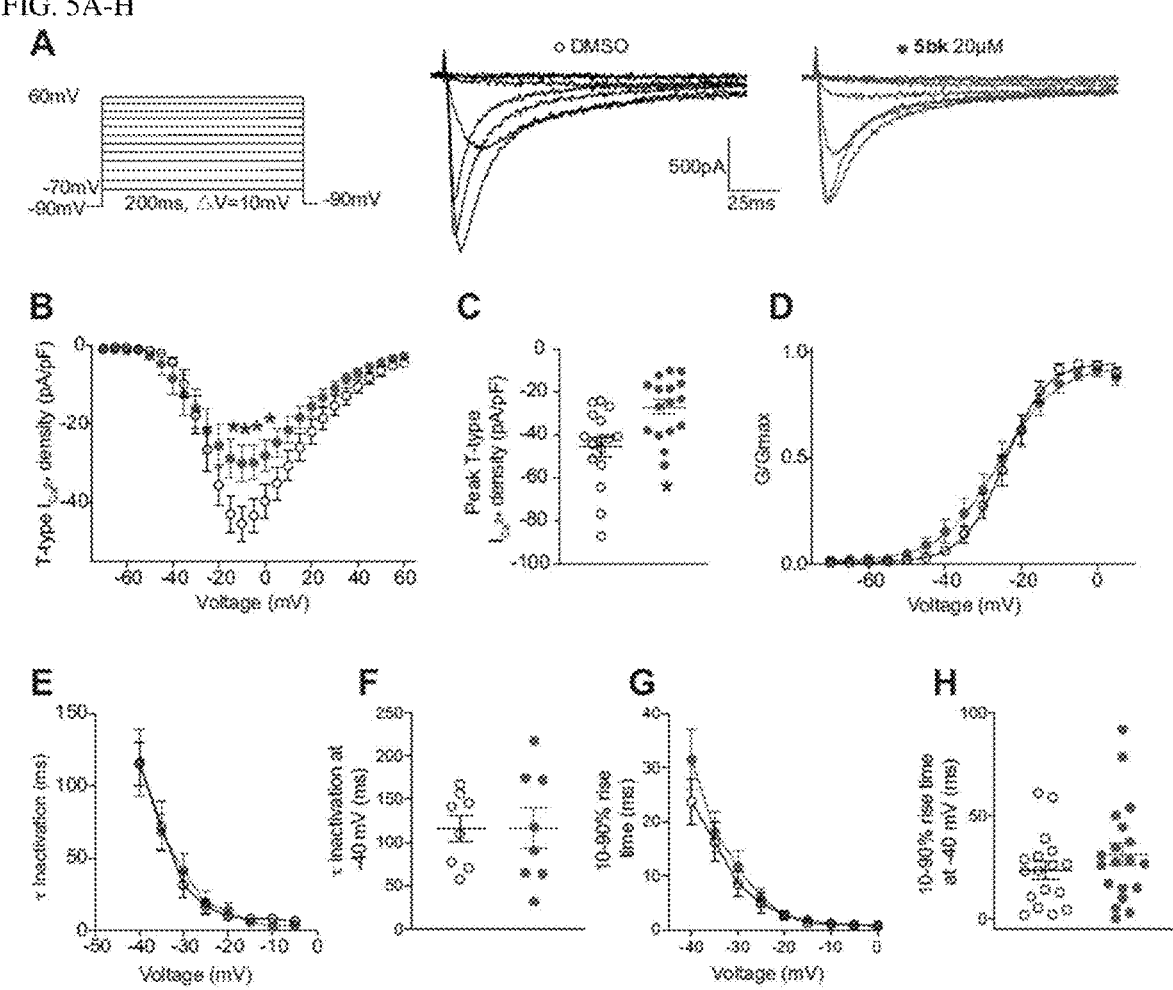

FIG. 5I-K
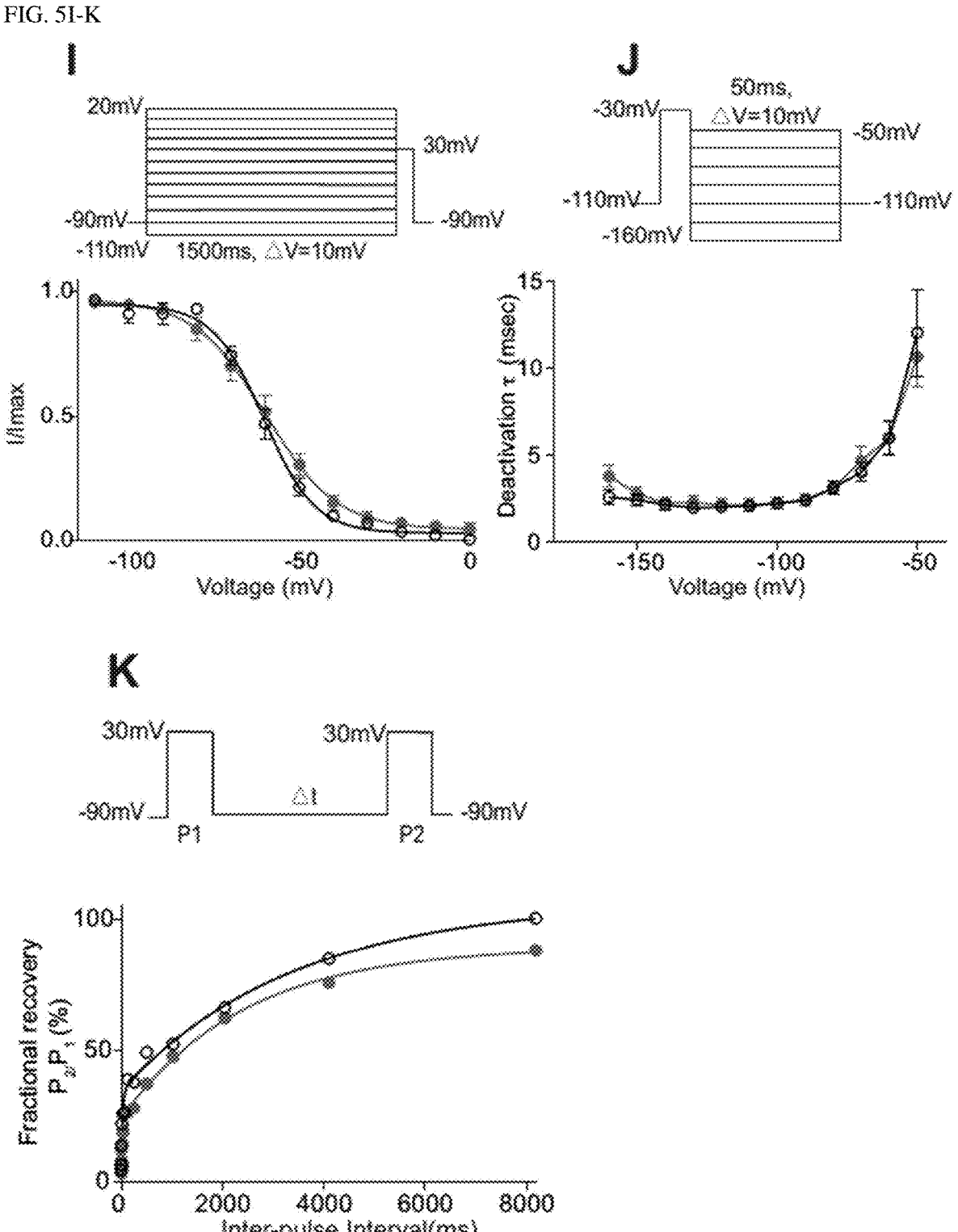

FIG. 6A-R
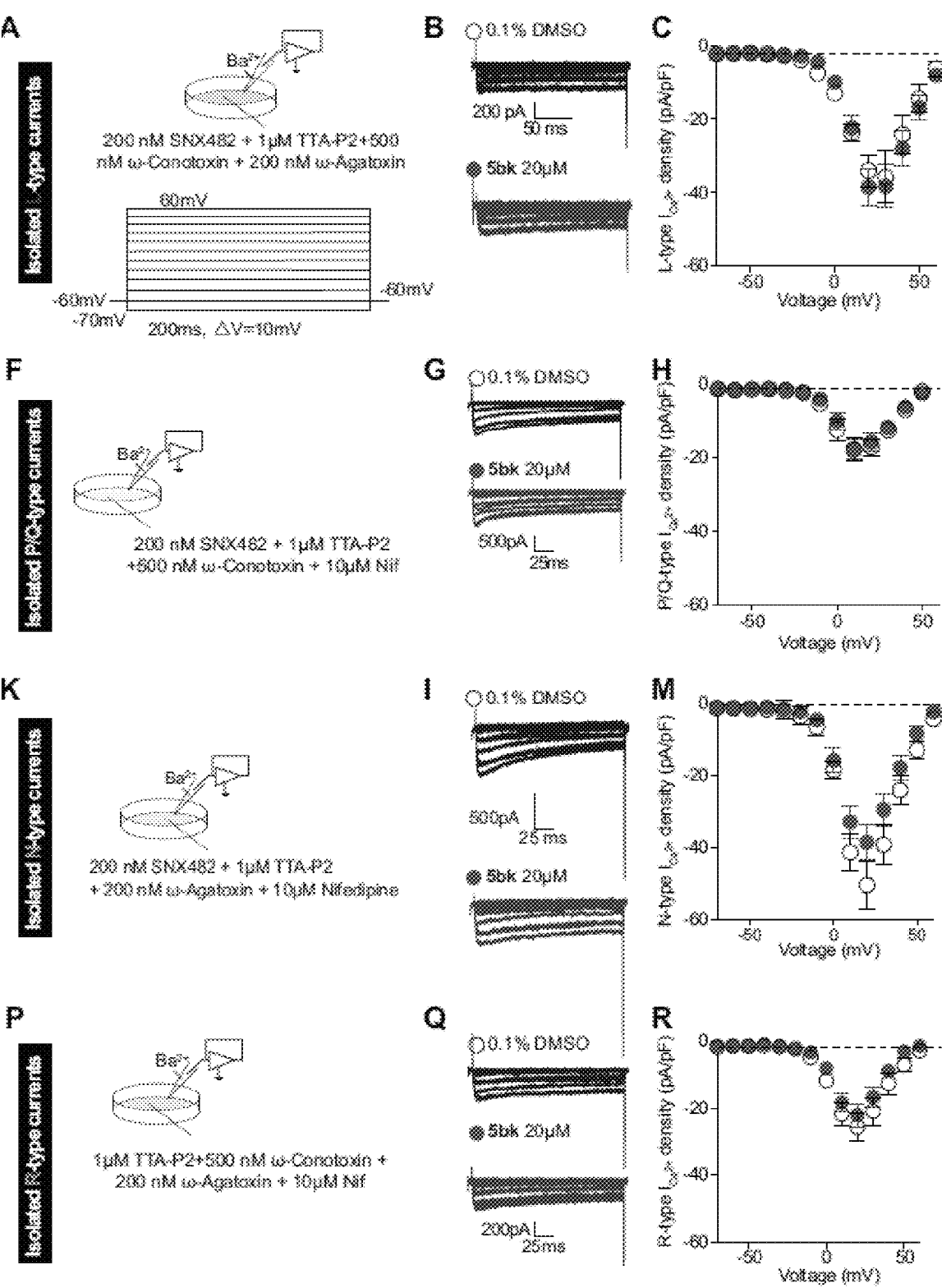

FIG. 6D-T
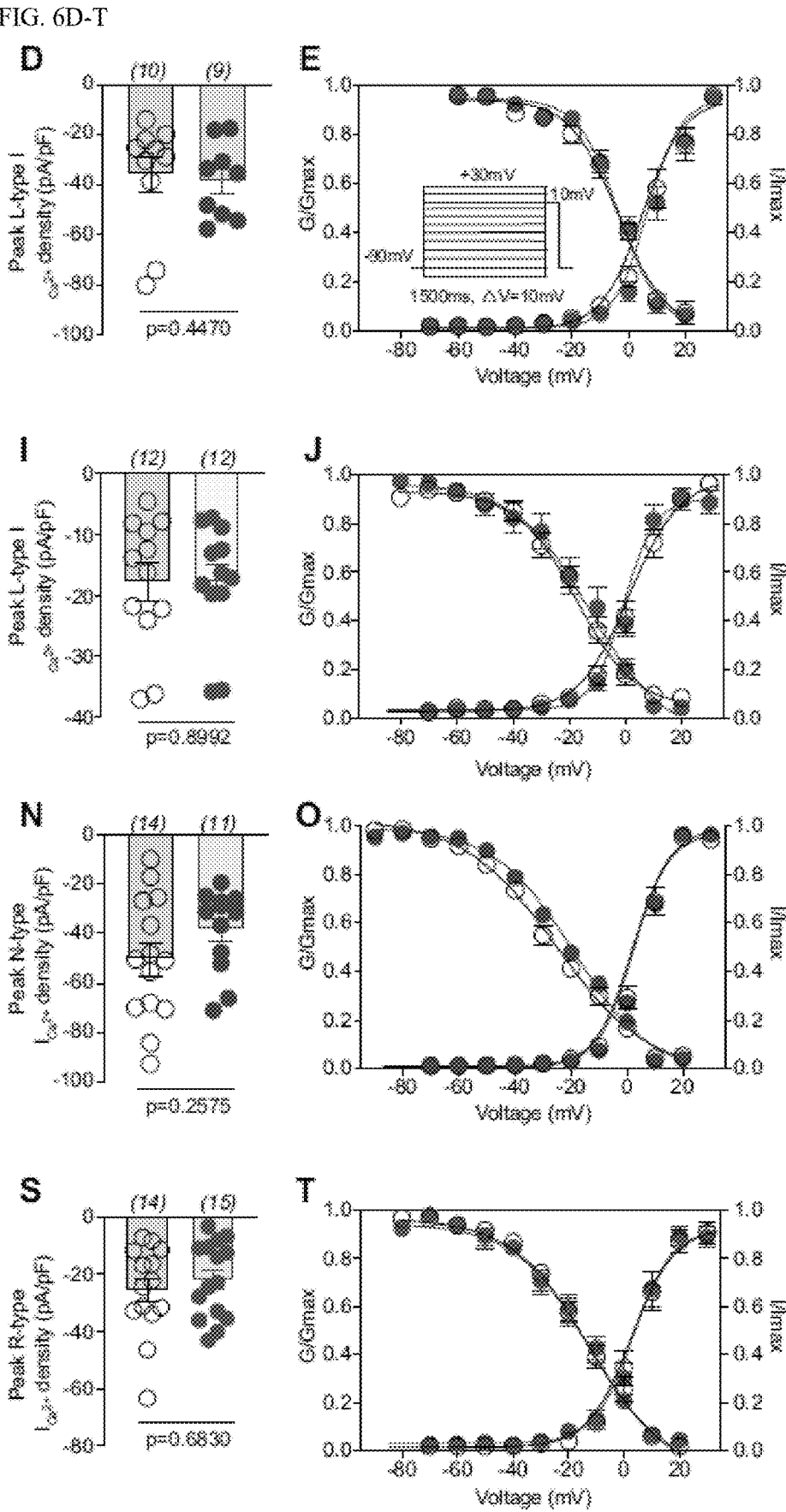

FIG. 7A-D
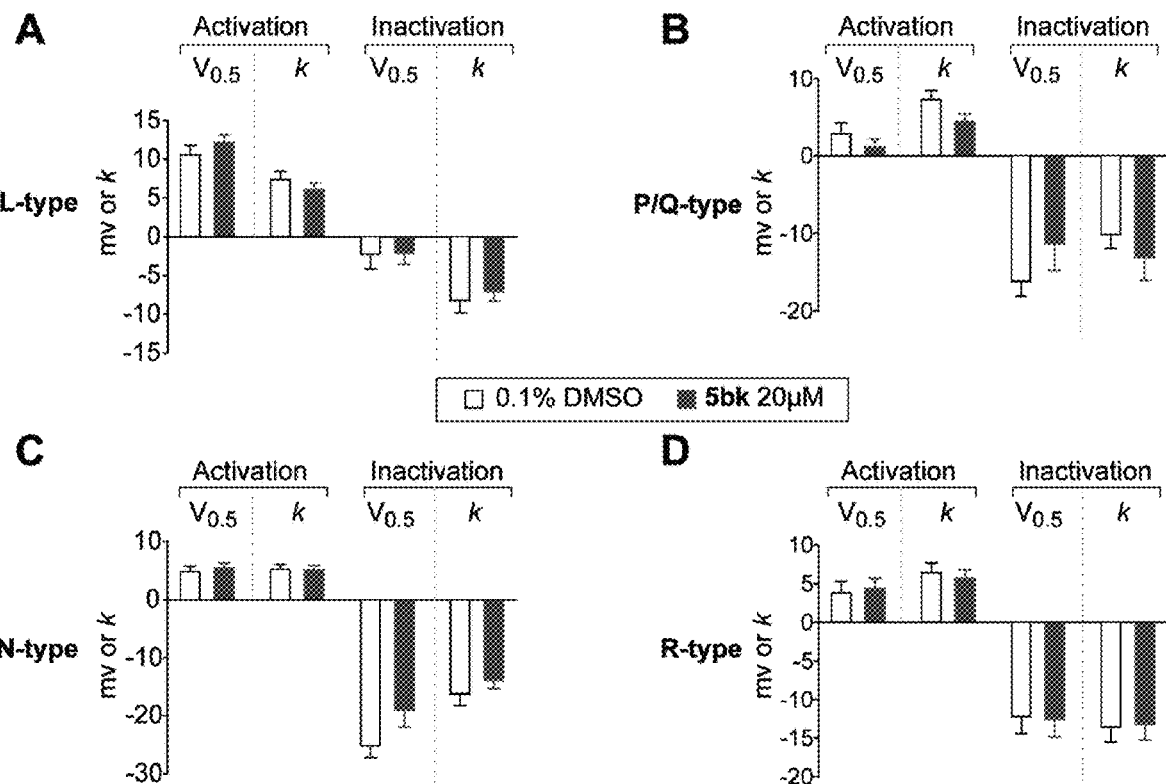
One-way ANOVA with Tukey's post hoc analysis: No comparisons significant FIG. 8A-E
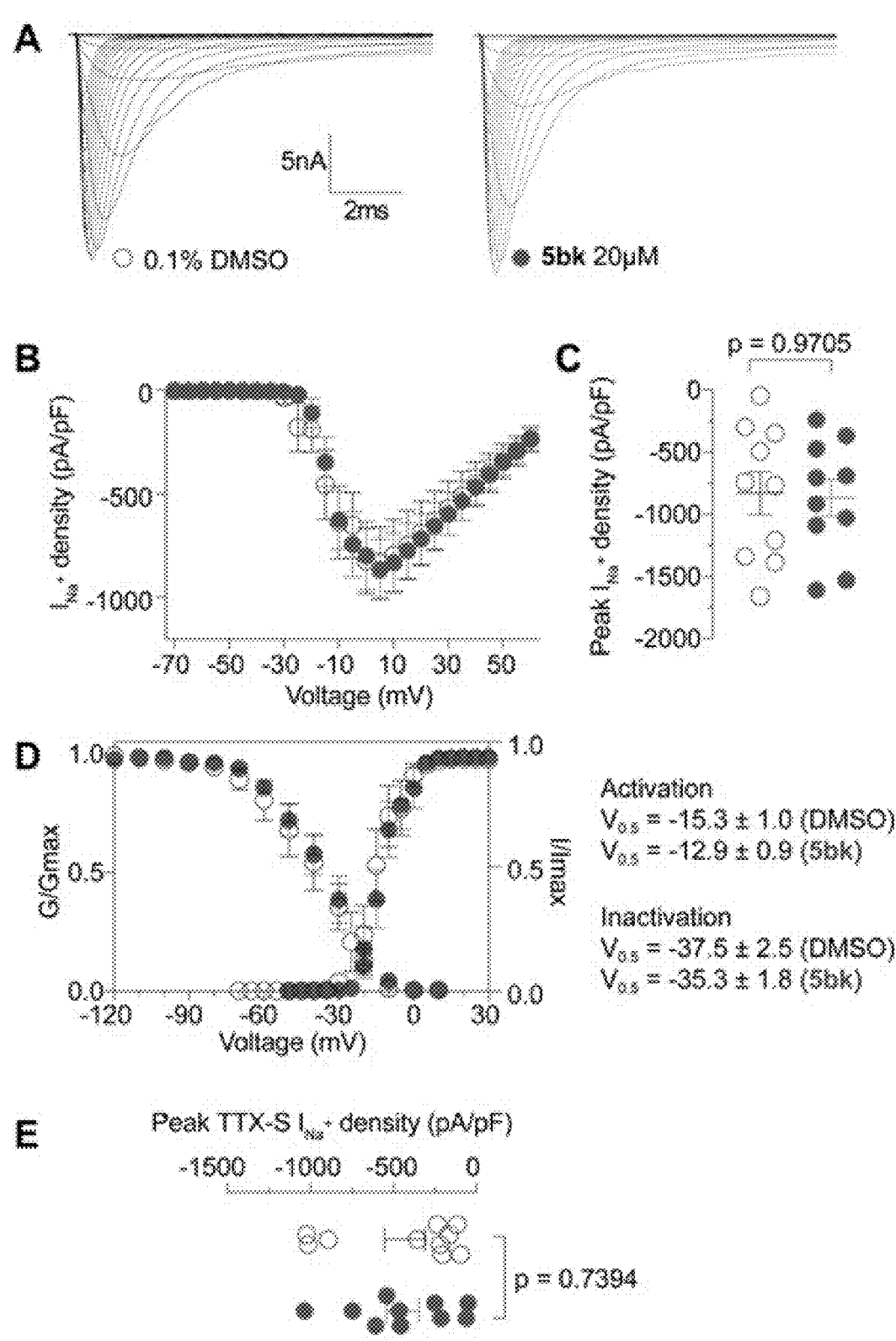

FIG. 10A-I

FIG. 13A-C
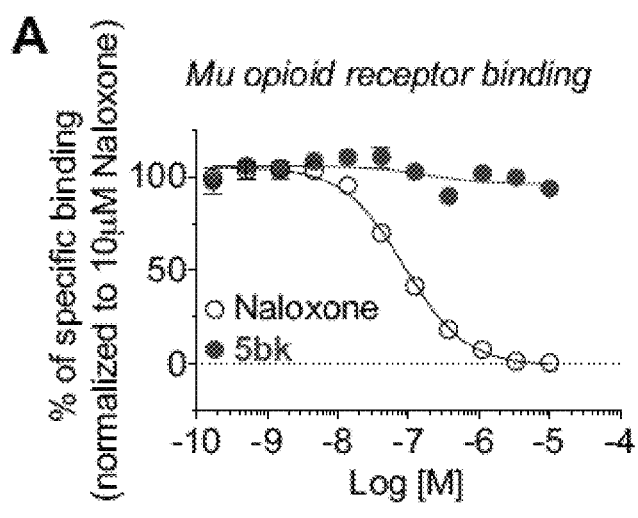
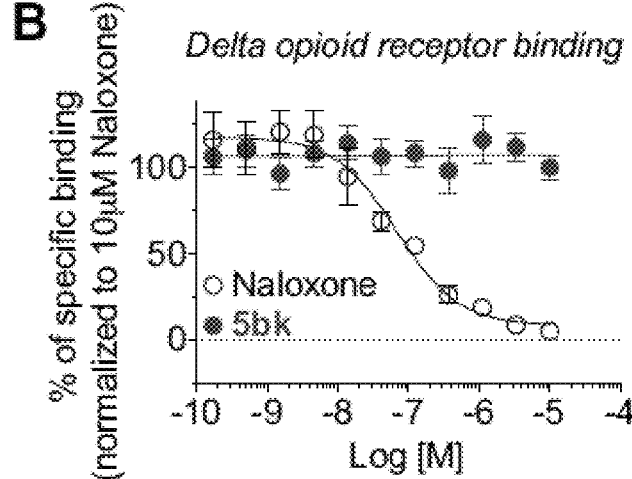
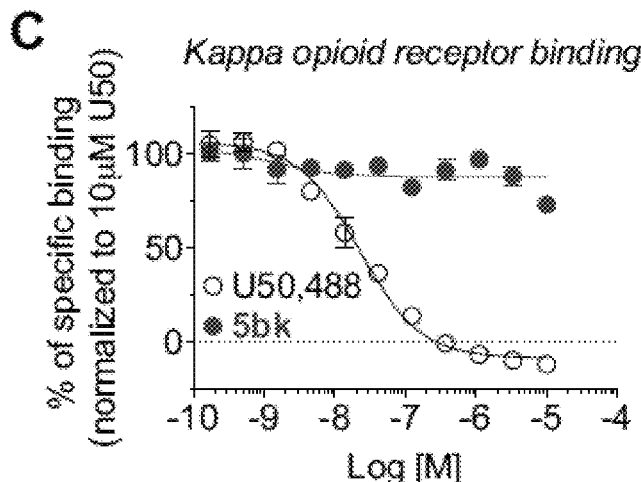

FIG. 14A-C
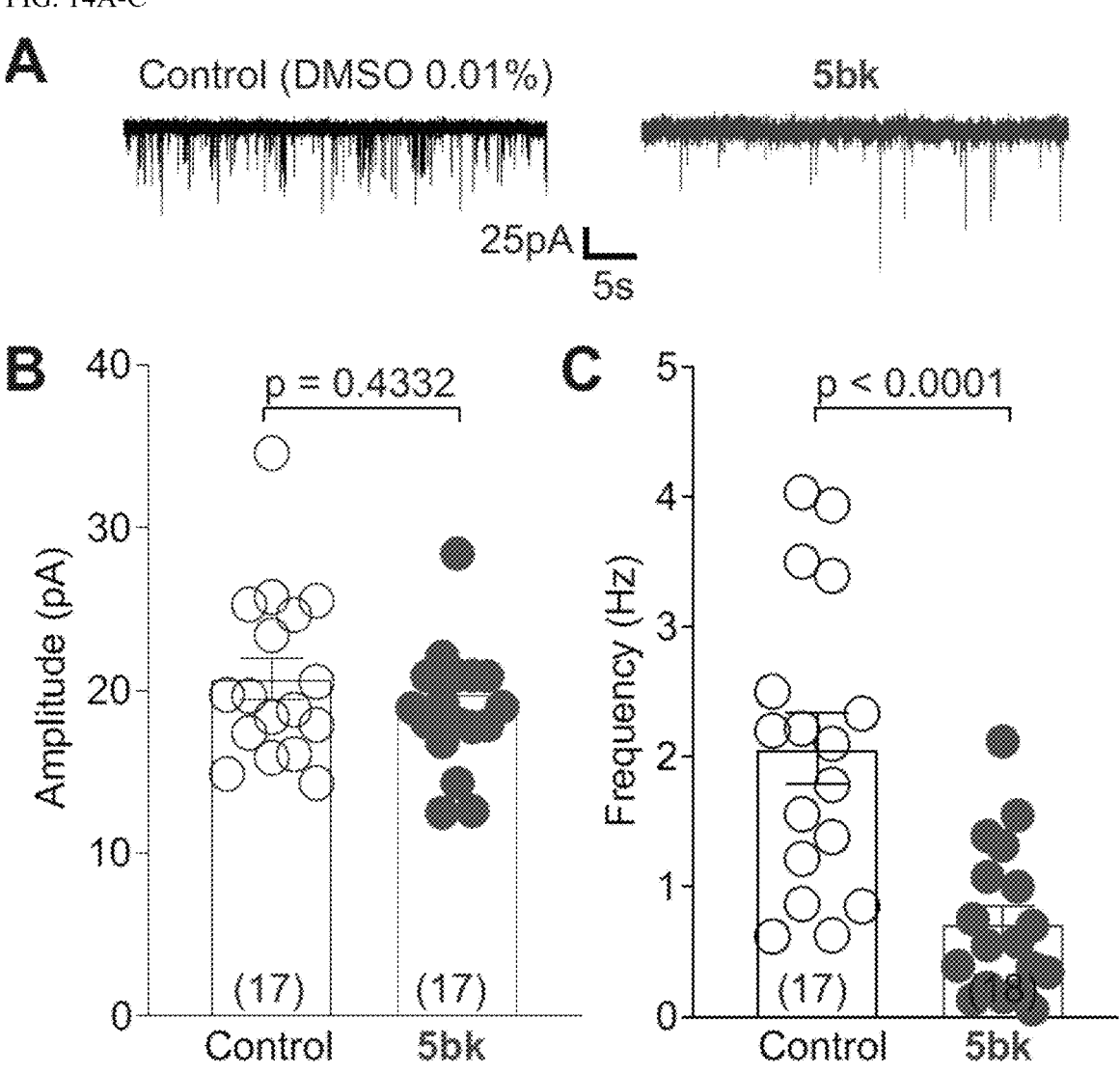

FIG. 15

1- Baseline 1
2- Baseline 2
3- Treatment
4- Treatment + 90 mM KCl
5- Wash 1

FIG. 16A-I
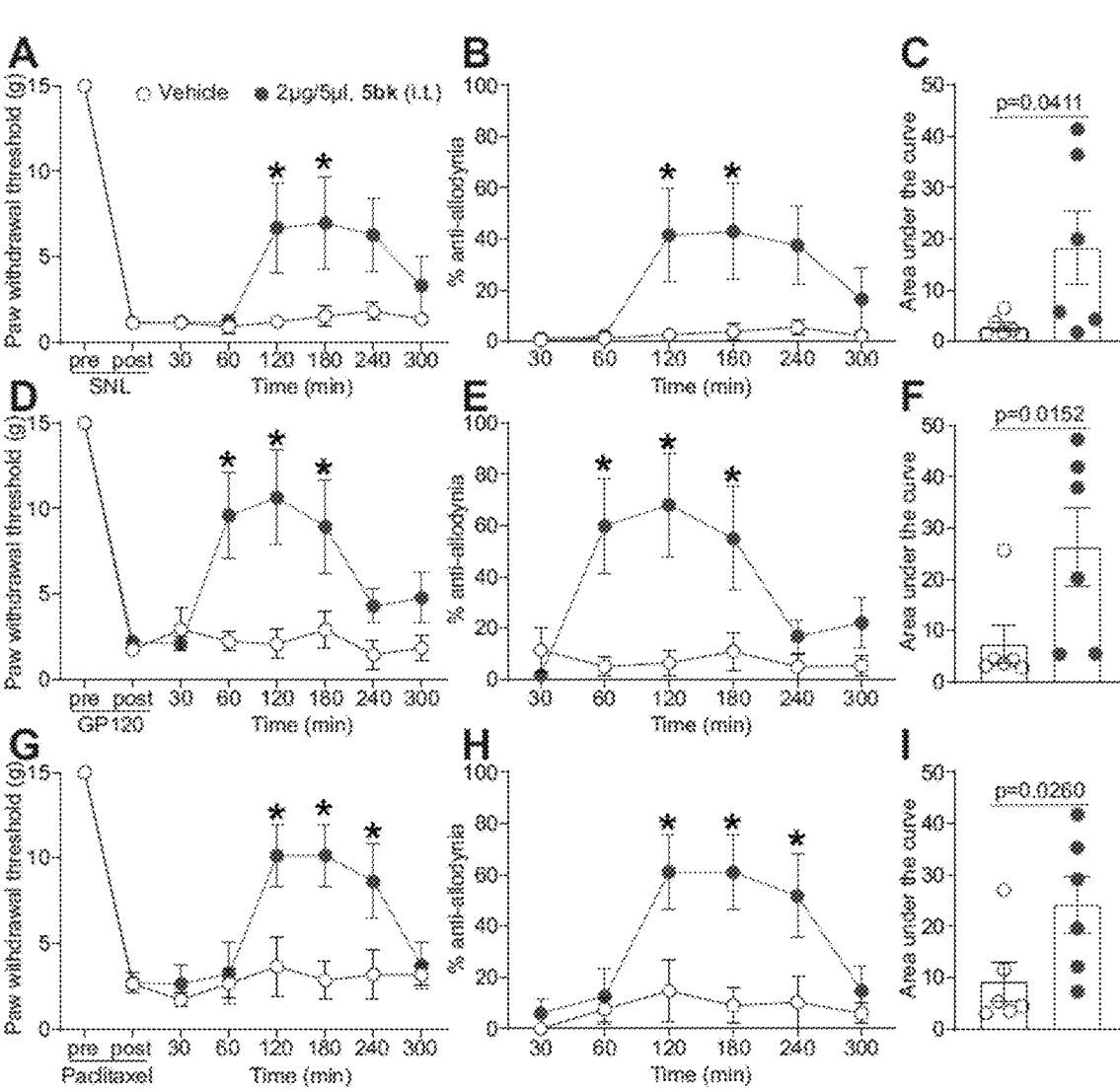

FIG. 17A-B
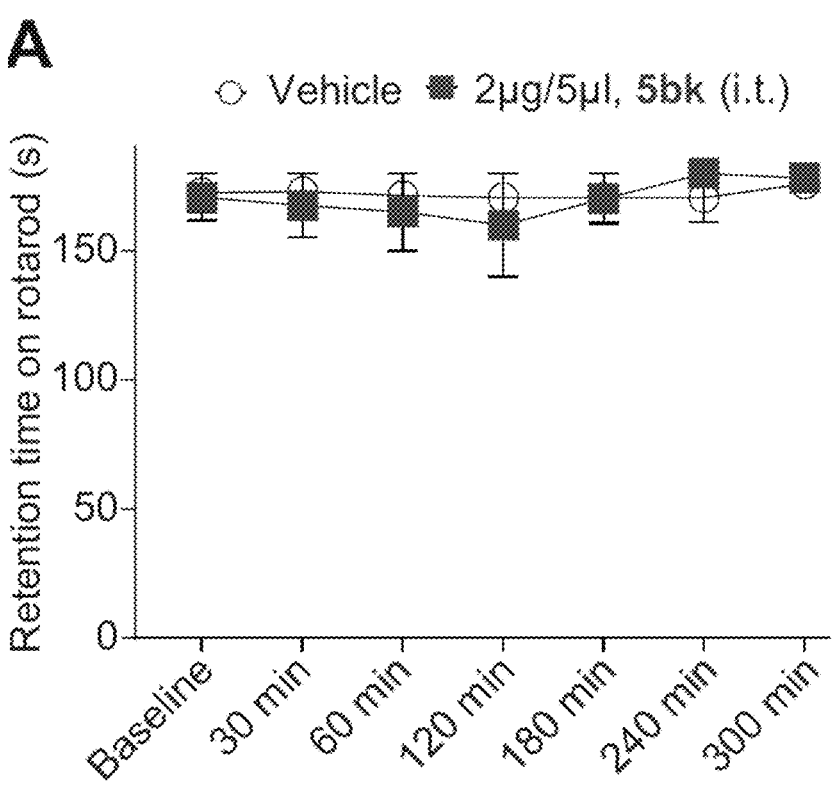
A
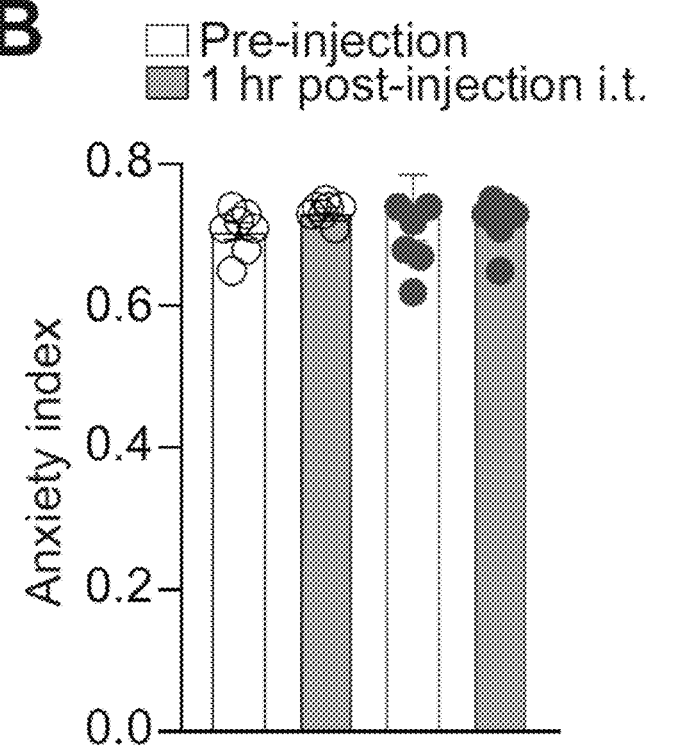
B

FIG. 18A-C
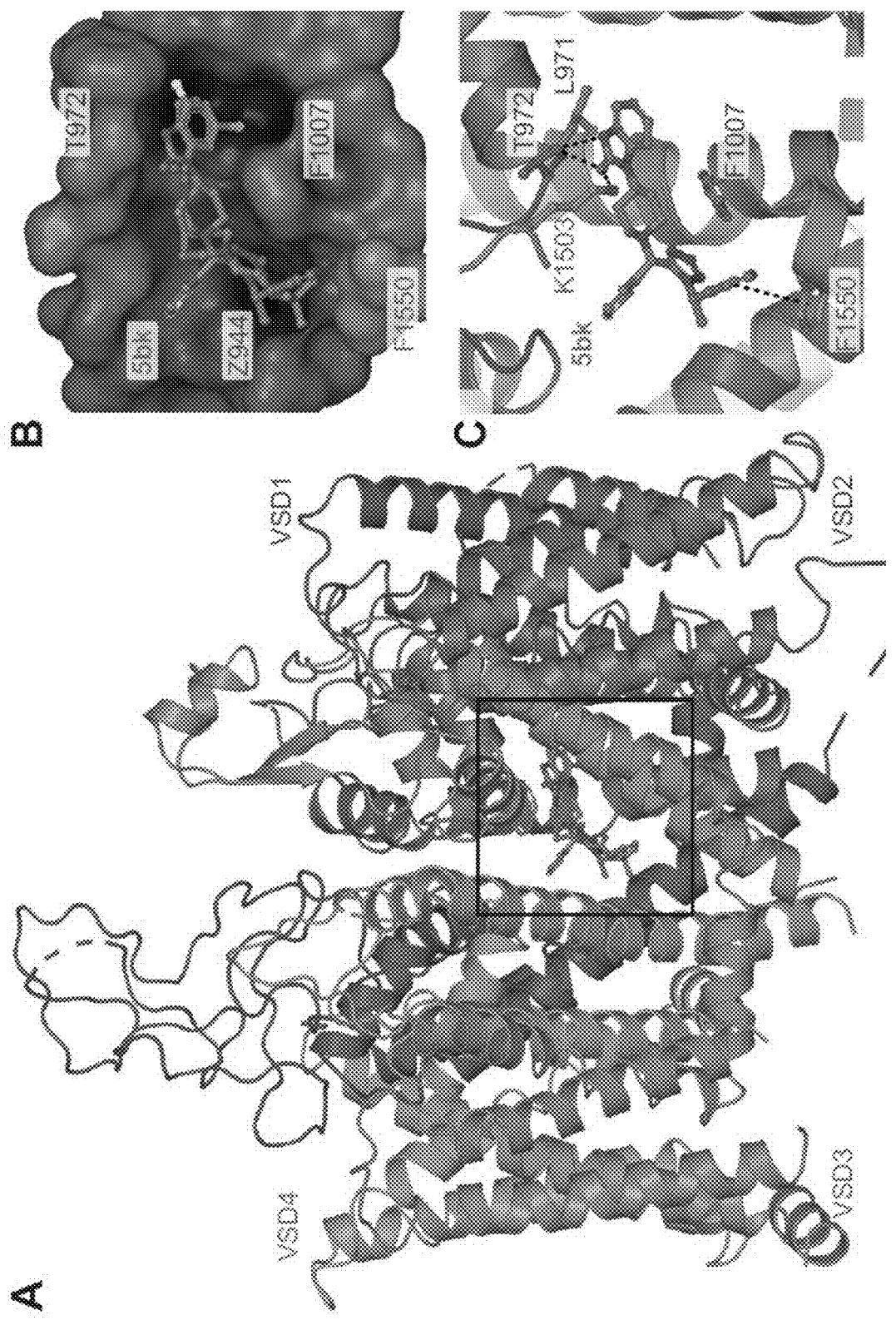

FIG. 19A-B
A
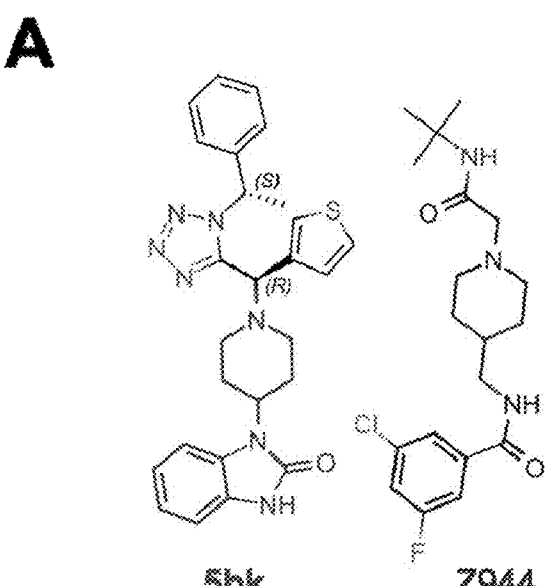
5bk          Z944
B
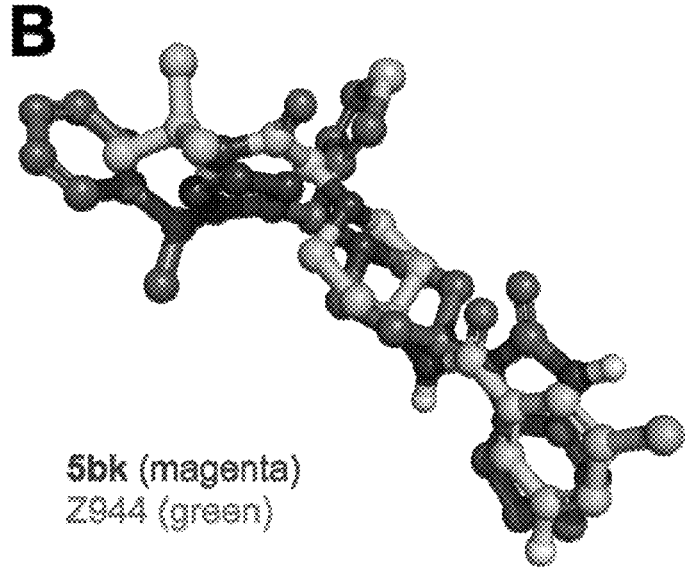
5bk (magenta)
Z944 (green)

3-2-1                    , 2-143-2                    , 2-193-2                    , 2-193-1                    , 2-201-2                    , and 3-3-2

1-159-2          1-159-2-S          1-159-2-R 3-14-3          3-14-3-R          3-14-3-S 3-25          3-25-S          3-25-R

FIG. 22A-D
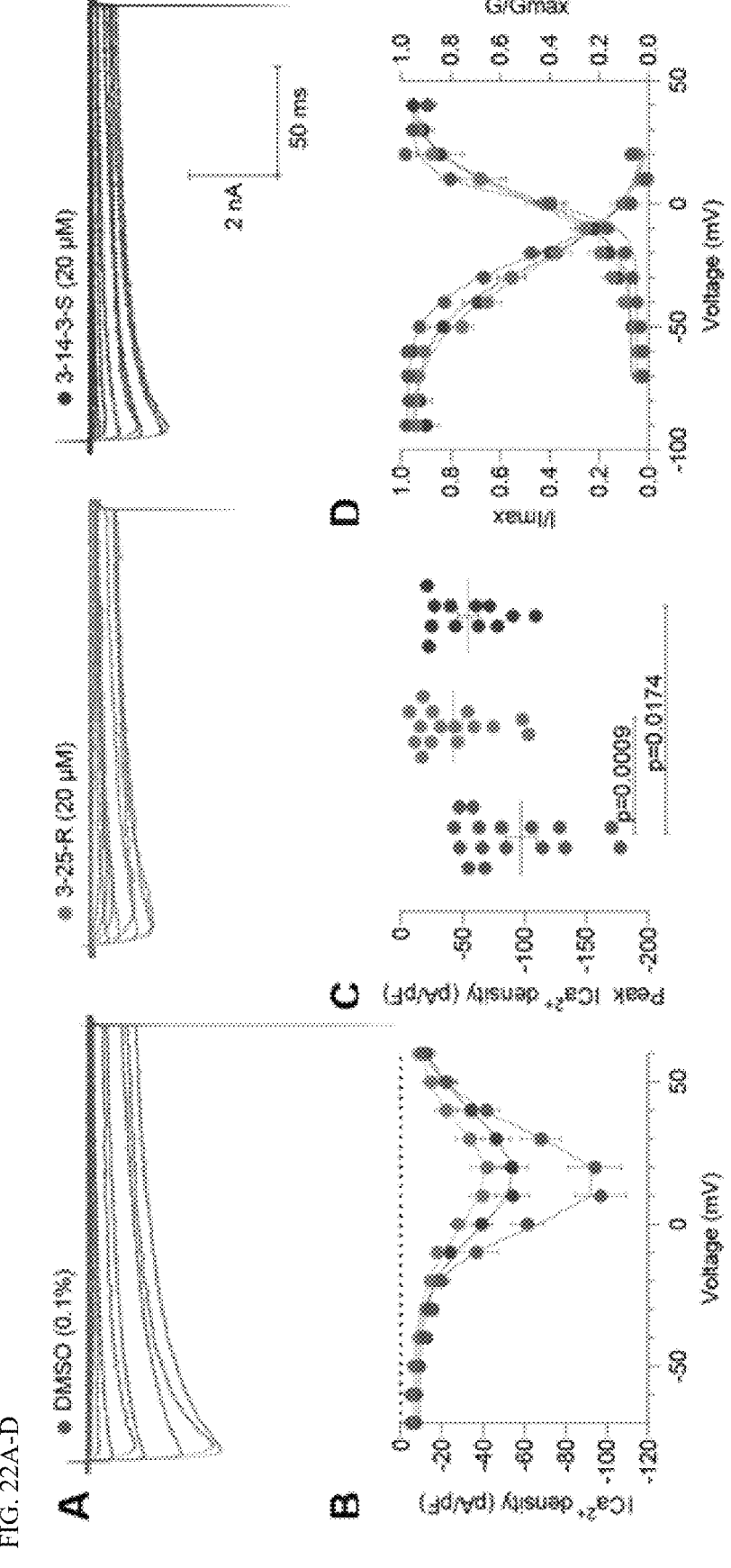

FIG. 23A-C
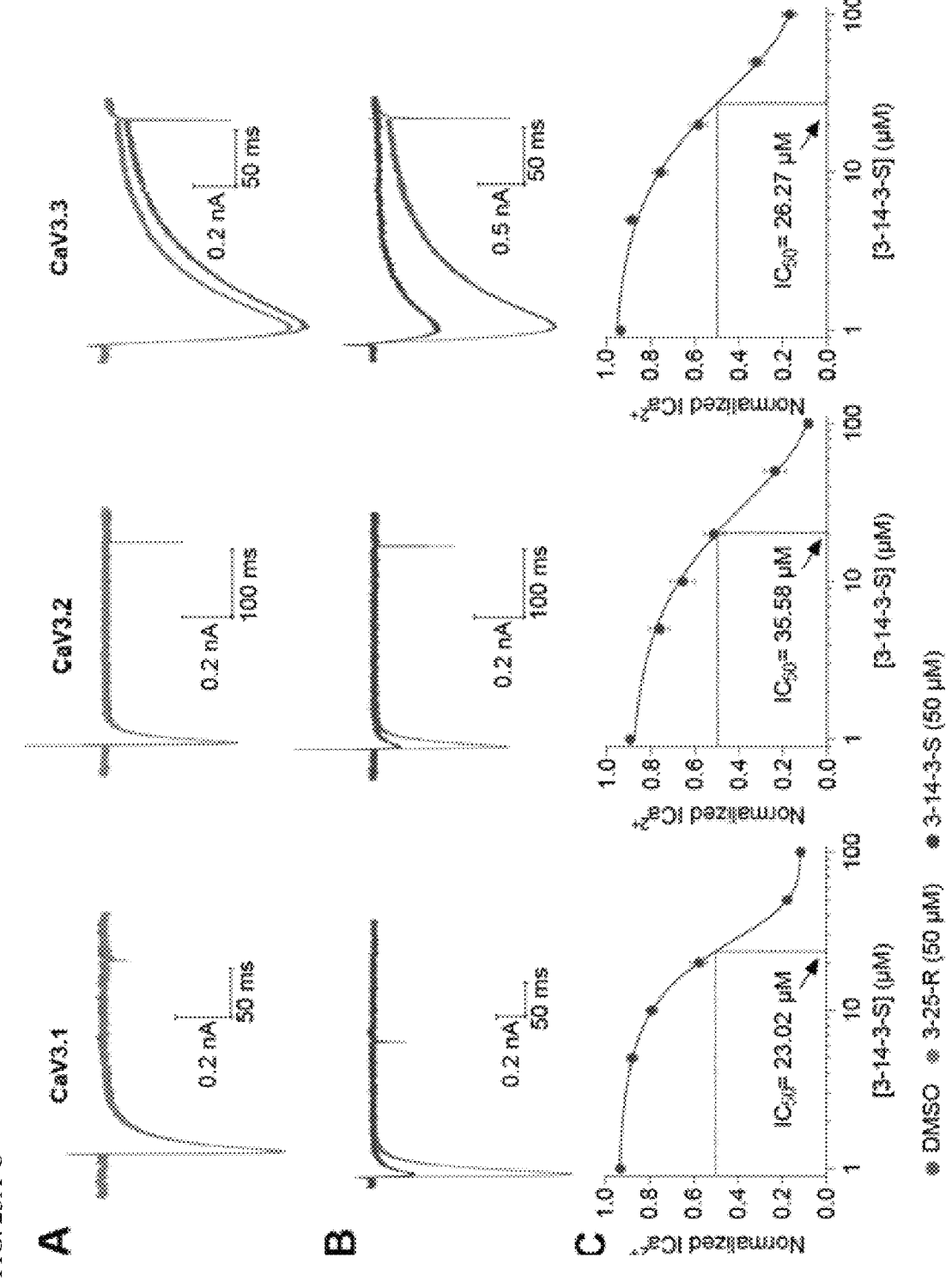

FIG. 24A-E
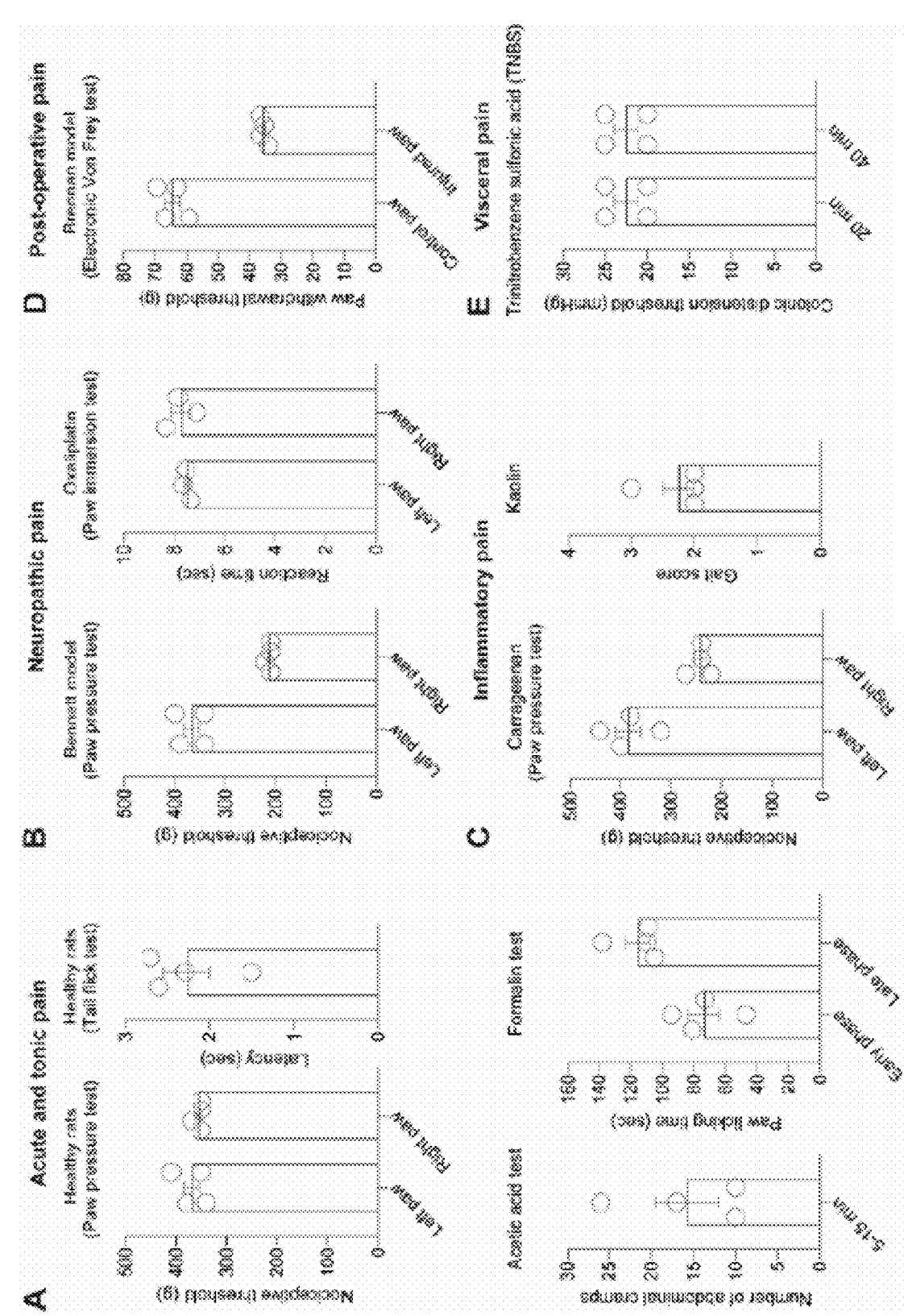

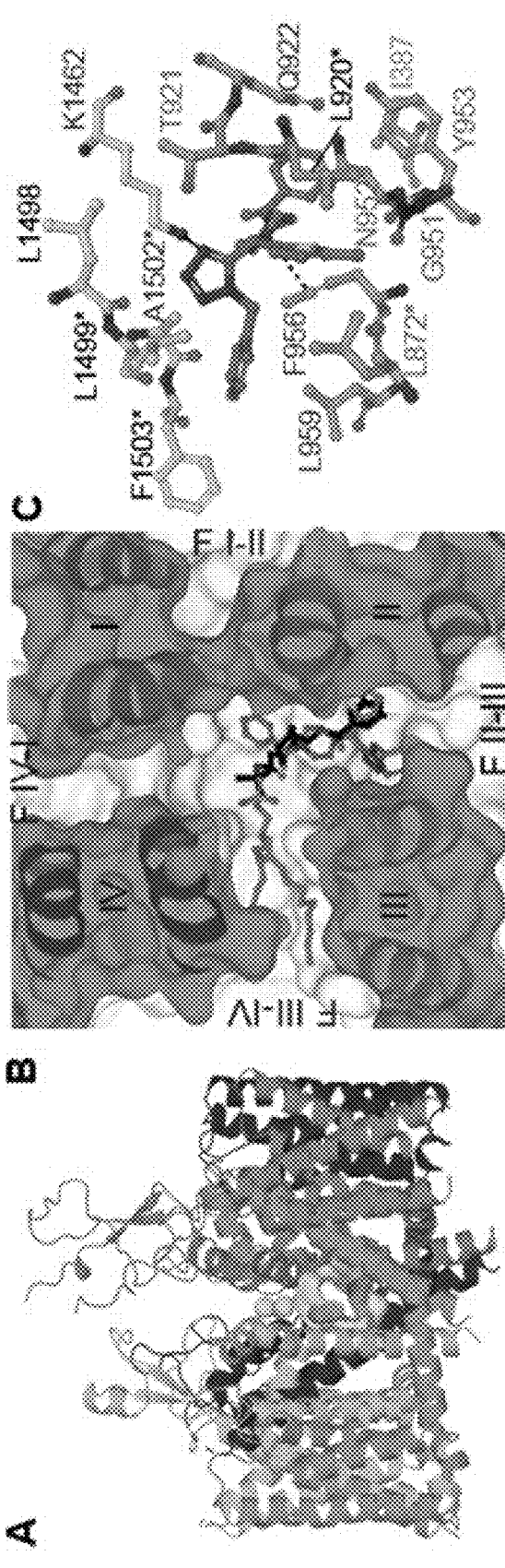
FIG. 25A-C

SEQUENCE LISTING

```
Sequence total quantity: 3
SEQ ID NO: 1            moltype = RNA   length = 25
FEATURE                 Location/Qualifiers
source                  1..25
                        mol_type = other RNA
                        organism = synthetic construct
SEQUENCE: 1
tagatagcaa atactttggc cgggg                                    25

SEQ ID NO: 2            moltype = RNA   length = 25
FEATURE                 Location/Qualifiers
source                  1..25
                        mol_type = other RNA
                        organism = synthetic construct
SEQUENCE: 2
cagccatctt cgtggtggag atgat                                    25

SEQ ID NO: 3            moltype = RNA   length = 25
FEATURE                 Location/Qualifiers
source                  1..25
                        mol_type = other RNA
                        organism = synthetic construct
SEQUENCE: 3
cagcatcctt gggatgcata tcttt                                    25
```

SMALL MOLECULE INHIBITORS OF CALCIUM CHANNEL ACTIVITY AND USES THEREOF

CROSS REFERENCE TO RELATED APPLICATIONS

This application claims priority to U.S. Provisional Application No. 63/291,828, filed Dec. 20, 2021, and is a continuation-in-part of U.S. application Ser. No. 17/924,863, filed Nov. 11, 2022, which is a U.S. 371 national phase entry of International Patent No. PCT/US2021/031964, filed May 12, 2021, which claims priority to and the benefit of U.S. Provisional Application No. 63/023,672, filed May 12, 2020, which are hereby incorporated by reference in their entireties.

STATEMENT REGARDING FEDERALLY SPONSORED RESEARCH OR DEVELOPMENT

This invention was made with government support under Grant No. R41 NS116784 awarded by National Institutes of Health. The government has certain rights in the invention.

SEQUENCE LISTING

The text of the computer readable sequence listing filed herewith, titled "38427_503_SequenceListing", created Dec. 20, 2022, having a file size of 4,000 bytes, is hereby incorporated by reference in its entirety.

FIELD OF THE INVENTION

This invention is in the field of medicinal chemistry. In particular, the invention relates to a new class of small-molecules having a piperazine or piperidine structure which function as either inhibitors of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx) or specific inhibitors of CaV3.2 voltage gated calcium channel activity, and their use as therapeutics for the treatment and/or prevention of pan-T-type calcium channel related pain (e.g., CaV3.1 related pain) (e.g., CaV3.2 related pain) (e.g., CaV3.3 related pain) (e.g., HIV-associated peripheral sensory neuropathy, chemotherapy-induced peripheral neuropathy (CIPN), spinal nerve ligation (SNL) induced neuropathy) (e.g., tonic, neuropathic, and/or inflammatory pain) and related conditions.

INTRODUCTION

The International Association for the Study of Pain defines pain as "An unpleasant sensory and emotional experience associated with, or resembling that associated with, actual or potential tissue damage". Pain is the most common reason patients seek medical care. Its control has been designed to minimize physical discomfort and improve the quality of life of patients.

Nonetheless, prescribing large amounts of opioid analgesics for pain treatment has led to a growing public health crisis of prescription drug abuse. Effective pain medication is undoubtedly one of the most neglected areas of global public health.

Notably, major advances in drug development over the past decades have vastly improved technical ability to treat pain. For instance, gabapentin (Neurontin*) and pregabalin (Lyrica®) are ligands of the $\alpha_2\delta$-1 auxiliary subunit of the voltage-gated $Ca^{2+}$ channel (VGCC) and both alleviate pain by disrupting channel trafficking to reduce $Ca^{2+}$ influx through high voltage-activated (HVA) $Ca^{2+}$ channels. However, the use of gabapentin causes severe side effects and has low efficacy. On the other hand, ziconotide (PRIALT®), an N-type (CaV2.2) VGCC blocker, was the first non-opioid intrathecal analgesic approved by the US Food and Drug Administration for the treatment of intractable chronic pain. Nevertheless, its invasive mode of delivery and narrow therapeutic window has caused complications for patients. Although the field of pain research is still evolving, developing novel therapeutic strategies to combat pain is still a great challenge. In this regard, discovering more selective and potent drugs targeting VGCCs will be beneficial for pain therapy.

Notably, neuropathic pain is a major health burden [27]. Despite intense research on the topic, very limited non-opioid treatments are available as alternatives. A failure to develop new drugs to combat pain is primarily because neuropathic pain is a complicated disease that can originate from many different types of injuries (nerve injury, chemotherapy [70], human immunodeficiency virus -HIV- infection [1] and others) and whose establishment involves central and peripheral systems. While neuropathic pain is a multisystemic disease, spinal block has been clinically demonstrated to curb neuropathic pain in patients [32]. Thus, targeting molecular components of spinal transmission is a valid therapeutic strategy for the treatment of chronic neuropathic pain [8] as evidenced by the N-type voltage gated calcium channel (CaV2.2) blocker Prialt® [82].

Ion channels regulating afferent fiber excitability and synaptic function in the spinal dorsal horn are prime targets for the treatment of neuropathic pain [81]. One of these channels is the T-type $Ca^{2+}$ channel [9]. These voltage-gated ion channels have a half activation voltage of $-45$ mV [78], thus their contribution to the initiation of an action potential precedes the contribution of $Na^+$ channels. The family of T-type $Ca^{2+}$ channels contain three isoforms in mammals, CaV3.1, CaV3.2 and CaV3.3 with distinct expression pattern in tissues [41; 43]. The biophysical properties of T-type $Ca^{2+}$ channels allow them to regulate neuronal excitability and to contribute to the generation of membrane potential oscillations that lead to action potential burst firing and pacemaker activity. Their dysfunction is associated with certain pathologies including epilepsy, cardiovascular diseases, cancer, and pain, among others. These channels are expressed in peripheral sensory neurons where they participate in nociceptive transmission and pain processing. For this reason, T-type calcium channels are salient molecular targets for the development of new non-opioid analgesics.

In dorsal root ganglia (DRG) neurons, the predominant CaV3 channel isoform involved in pain signaling is CaV3.2 [4; 6]. CaV3.2 expression is restricted to the nociceptive A- and C-low-threshold mechanoreceptors (LTMRs)[22]. CaV3.2 expression is increased following nerve injury [26]. Cav3.2 activity is also increased in paclitaxel-induced peripheral neuropathy [21; 58; 65; 87]. A specific role of CaV3.2 in pain was demonstrated by the observation that silencing this channel in DRG neurons reversed neuropathic pain in rats while silencing CaV3.1 or CaV3.3 did not [6]. Further evidence in support of CaV3 channels as important therapeutic targets for pain comes from studies of the T-type $Ca^{2+}$ channels inhibitors ethosuximide [13; 31; 69], mibefradil, TTA-A2 or TTA-P2 [14; 77]—all of which reverse experimental neuropathic pain in rodents. However, clinical trials using T-type $Ca^{2+}$ channel blockers for pain, such as ABT-639 [77] and MK-8998 [19], failed to meet the expected clinical endpoints. This may have been due to lack of selectivity for CaV3.2 leading to dose limitations. Another promising compound that may advance to clinic is Z944 used for treating neuropathic, inflammatory, visceral and acute pain [42; 80] passed Phase 1a and 1b clinical trials, however, it is unclear whether Z944 advanced into Phase II.

Thus, there is a need for pan-T-type calcium channel activity (e.g., CaV3.1 voltage gated calcium channel activity) (e.g., CaV3.2 voltage gated calcium channel activity) (e.g., CaV3.3 voltage gated calcium channel activity) blockers.

In addition, there is a need for a specific CaV3.2 blocker.

The present invention addresses these needs.

SUMMARY OF THE INVENTION

It has been shown before that a natural compound betulinic acid (3β)-3-Hydroxy-lup-20(29)-en-28-oic acid), preferentially targets CaV3.2 and could reverse a could reverse allodynia in the paclitaxel induced peripheral neuropathy and HIV related sensory neuropathy models [3].

In searching for selective CaV3.2 T-type calcium channel blockers, experiments conducted during the course of developing embodiments for the present invention first performed a screening of an in-house chemical library using Fura 2-AM based ratiometric calcium-imaging assay. One hit compound, 5aa see FIG. 1B) was identified to inhibit ~50% of the $Ca^{2+}$ influx when DRGs were depolarized with 40 mM KCl. Subsequent structure-activity relationship studies led to a more potent analog 5bk see FIG. 1B). The T-type calcium channel block of 5bk was further confirmed in whole-cell patch clamp assays in rat DRGs, where pharmacological isolation of T-type currents leads to a concentration-dependent inhibition with an $IC_{50}$ of 4.2±0.6 µM. By silencing each of the CaV3 channels, it was found that 5bk could selectively inhibit CaV3.2. 5bk was shown to reverse mechanical allodynia in neuropathic— Chemotherapy-(paclitaxel) and HIV-induced—pain. 5bk inhibited spontaneous excitatory post-synaptic currents via actions presynaptically and inhibited release of the pronociceptive neurotransmitter calcitonin gene related peptide (CGRP). As 5bk did not affect locomotion or anxiety and was without action on opioid receptors, it appears to be a promising, safe, and non-opioid candidate for the treatment of neuropathic pain by virtue of its selective block of CaV3.2 T-type calcium channels.

In additional experiments, natural small molecules and Ugi-azide four-component reaction products were screened to target T-type calcium channels for pain relief In a previous study, an analog of benzimidazolonepiperidine, 5bk (1-{1-(R)-{1-[(1S)-1-phenylethyl]-1H-1,2,3,4-tetrazol-5-yl}(thiophen-3-yl)methyl]piperidin-4-yl}-2,3-dihydro-1H-1,3-benzodiazol-2-one), was found to decrease $Ca^{2+}$ influx and reverse mechanical allodynia in rodent models of HIV-associated neuropathy, chemotherapy-induced peripheral neuropathy, and spinal nerve ligation-induced neuropathy (Cai, S., Tuohy, P., Ma, C., Kitamura, N., Gomez, K., Zhou, Y., Ran, D., Bellampalli, S. S., Yu, J., Luo, S., Dorame, A., Yen Ngan Pham, N., Molnar, G., Streicher, J. M., Patek, M., Perez-Miller, S., Moutal, A., Wang, J., and Khanna, R. (2020) A modulator of the low-voltage-activated T-type calcium channel that reverses HIV glycoprotein 120-, paclitaxel-, and spinal nerve ligation-induced peripheral neuropathies, Pain 161, 2551-2570) (herein referred to as "Cai et al."). Such experiments further determined that the compound 3-14-3-S (S)-(4-((1-benzyl-1H-tetrazol-5-yl)(5-methylthiophen-2-yl)methyl)piperazin-1-yl)(furan-2-yl)methanone was found to have the potential to inhibit KCl- Induced $Ca^{2+}$ influx in dorsal root ganglia neurons. Furthermore, 3-14-3-S diminished $Ca^{2+}$ current density in rat sensory neurons and blocked transiently expressed CaV3.1, CaV3.2 and CaV3.3 channels with a similar IC50. Consistent with inhibition of voltage-gated calcium channels, intrathecal delivery of 3-14-3-S mediated relief of tonic, neuropathic and inflammatory pain. Lastly, both 3-14-3 enantiomers were shown through in silico docking to bind to the CaV3.1 structure. These results suggest that multi-targeting T-type $Ca^{2+}$ channel isoforms may yield a more efficacious strategy for non-opioid pain management.

Accordingly, the present invention is in the field of medicinal chemistry. In particular, the invention relates to a new class of small-molecules having a piperazine or piperidine structure which function as either inhibitors of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx) or specific inhibitors of CaV3.2 voltage gated calcium channel activity, and their use as therapeutics for the treatment and/or prevention of pan-T-type calcium channel related pain (e.g., CaV3.1 related pain) (e.g., CaV3.2 related pain) (e.g., CaV3.3 related pain) (e.g., HIV-associated peripheral sensory neuropathy, chemotherapy-induced peripheral neuropathy (CIPN), spinal nerve ligation (SNL) induced neuropathy) (e.g., tonic, neuropathic, and/or inflammatory pain) and related conditions.

Certain piperazine or piperidine (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

including pharmaceutically acceptable salts, solvates, and/or prodrugs thereof.

Formula I is not limited to a particular chemical moiety for X, R1, R2, and R3. In some embodiments, the particular chemical moiety for X, R1, R2, and R3 independently include any chemical moiety that permits the resulting compound to inhibit pan-T-type voltage gated calcium channel activity (e.g., CaV3.1 voltage gated calcium channel activity) (e.g., CaV3.2 voltage gated calcium channel activity) (e.g., CaV3.3 voltage gated calcium channel activity). In some embodiments, the particular chemical moiety for X, R1, R2, and R3 independently include any chemical moiety that permits the resulting compound to specifically inhibit CaV3.2 voltage gated calcium channel activity. In some embodiments, the particular chemical moiety for X, R1, R2, and R3 independently include any chemical moiety that permits the resulting compound to inhibit depolarization-induced calcium influx related to pan-T-type voltage gated calcium channel activity. In some embodiments, the particular chemical moiety for X, R1, R2, and R3 independently include any chemical moiety that permits the resulting compound to inhibit depolarization-induced calcium influx related to CaV3.2 voltage gated calcium channel activity. In some embodiments, the particular chemical moiety for X, R1, R2, and R3 independently include any chemical moiety that permits the resulting compound to inhibit, prevent and/or ameliorate neuropathy pain related to pan-T-type activity. In some embodiments, the particular chemical moiety for X, R1, R2, and R3 independently include any chemical moiety that permits the resulting compound to inhibit, prevent and/or ameliorate neuropathy pain related to CaV3.2 activity. In some embodiments, the particular chemical moiety for X, R1, R2, and R3 independently include any chemical moiety that permits the resulting compound to inhibit, prevent and/or ameliorate pain related to pan-T-type activity. In some embodiments, the particular chemical moiety for X, R1, R2, and R3 independently include any chemical moiety that permits the resulting compound to inhibit, prevent and/or ameliorate pain related to CaV3.2 activity. In some embodiments, the particular chemical moiety for X, R1, R2, and R3 independently include any chemical moiety that permits the resulting compound to inhibit, prevent and/or ameliorate pain related to HIV-associated peripheral sensory neuropathy. In some embodiments, the particular chemical moiety for X, R1, R2, and R3 independently include any chemical moiety that permits the resulting compound to inhibit, prevent and/or ameliorate pain related to chemotherapy-induced peripheral neuropathy (CIPN). In some embodiments, the particular chemical moiety for X, R1, R2, and R3 independently include any chemical moiety that permits the resulting compound to inhibit, prevent and/or ameliorate tonic, neuropathic, and/or inflammatory pain. In some embodiments, the particular chemical moiety for X, R1, R2, and R3 independently include any chemical moiety that permits the resulting compound to inhibit, prevent and/or ameliorate pain related to spinal nerve ligation (SNL) induced neuropathy. In some embodiments, the particular chemical moiety for X, R1, R2, and R3 independently include any chemical moiety that permits the resulting compound to inhibit spontaneous excitatory post-synaptic currents via actions presynaptically. In some embodiments, the particular chemical moiety for X, R1, R2, and R3 independently include any chemical moiety that permits the resulting compound to inhibit release of the pronociceptive neurotransmitter calcitonin gene related peptide (CGRP).

In some embodiments, X is C thereby rendering the compound a piperidine based compound.

In some embodiments, X is N thereby rendering the compound a piperazine based compound.

In some embodiments, R1 is selected from

7

8

In some embodiments, R2 is selected from

In some embodiments, R1 is hydrogen.

-continued

5bk

In some embodiments, R2 is hydrogen.

In some embodiments, R3 is selected from

In some embodiments, R3 is hydrogen.

In some embodiments, the compound is recited in FIG. 1B and FIG. 21A.

In some embodiments, the compound recited in FIG. 1B is a specific inhibitor of CaV3.2 voltage gated calcium channel activity.

In some embodiments, the compound recited in FIG. 21A is an inhibitor of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx).

In some aspects, the present invention features a calcium channel modulator that is a derivative of 5bk below:

According to some embodiments, the modulator is according to any one of the following compounds:

1-159-2

3-14-3

11

3-25

In some embodiments, the modulator can be the S- or R-enantiomer of said compounds, as shown below:

1-159-2-S

1-159-2-R

12

3-14-3-R 3-14-3-S 3-25-S 3-25-R

In some preferred embodiments, the modulator is 3-14-3-S:

3-14-3-S

Without wishing to limit the invention to a particular theory or mechanism, 3-14-3-S may be effective for inhibiting depolarization-induced $Ca^{2+}$ influx through T-type $Ca^{2+}$ channels. Also, 3-14-3-S may be effective for decreasing $Ca^{2+}$ current density and T-type $Ca^{2+}$ currents. In some embodiments, 3-14-3-S is effective for treating and preventing pain.

The invention further provides processes for preparing any of the compounds of the present invention.

The pan-T-type inhibitors and specific CaV3.2 inhibitors described herein can be considered as potential therapeutics for the treatment, prevention, and/or amelioration of conditions characterized with pain related pan-T-type activity or specific CaV3.2 activity (e.g., pain related to general neuropathy; pain related to diabetes related neuropathy; pain related to HIV-associated peripheral sensory neuropathy; inhibiting, preventing and/or ameliorating pain related to chemotherapy-induced peripheral neuropathy (CIPN); inhibiting, preventing and/or ameliorating pain related to spinal nerve ligation (SNL) induced neuropathy; inhibiting, preventing and/or ameliorating tonic, neuropathic, and/or inflammatory pain).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., other agents useful in treating, preventing and/or ameliorating pain related to pan-T-type activity or specific CaV3.2 activity.

According to some embodiments, the present invention features a composition for use in blocking a calcium channel. In preferred embodiments, the composition may comprise one or more of the compounds described herein. In other aspects, the present invention features a method of blocking a calcium channel. In some embodiments, the method may comprise exposing the calcium channel to a compound as described herein.

According to some embodiments, the present invention features a composition for use in treating or preventing pain, such as tonic, neuropathic, and/or inflammatory pain. In preferred embodiments, the composition may comprise one or more of the calcium channel modulators described herein, in a pharmaceutically acceptable carrier. In other embodiments, the present invention features a method of treating or preventing pain in a subject in need of such treatment. The method may comprise administering to the subject a therapeutically effective amount of one or more of the calcium channel modulators described herein.

In certain embodiments, the present invention provides a calcium channel modulator, wherein the modulator is a derivative of 5bk:

5bk

In some embodiments, the modulator is T-type calcium channel blocker. In some embodiments, the modulator is effective for blocking CaV3.1, CaV3.2 and/or CaV3.3 channels. In some embodiments, the modulator is according to any one of the following compounds:

1-159-2

3-14-3

, or

15

-continued 3-25

In some embodiments, the modulator comprises the S- or R- enantiomer of said compounds:

1-159-2-S 1-159-2-R

16

-continued 3-14-3-R 3-14-3-S 3-25-S 3-25-R

In some embodiments, the modulator is 3-14-3-S:

3-14-3-S

In some embodiments, 3-14-3-S is effective for inhibiting depolarization-induced $Ca^{2+}$ influx through T-type $Ca^{2+}$ channels. In some embodiments, 3-14-3-S is effective for decreasing $Ca^{2+}$ current density and T-type $Ca^{2+}$ currents. In some embodiments, 3-14-3-S is effective for treating and preventing pain. In some embodiments, the modulator is effective for treating tonic, neuropathic, and/or inflammatory pain.

In certain embodiments, the present invention provides a composition for use in treating or preventing pain, said composition comprising a calcium channel modulator recited in FIG. 21A, in a pharmaceutically acceptable carrier. In some embodiments, the pain is tonic, neuropathic, and/or inflammatory pain.

In certain embodiments, the present invention provides a method of treating or preventing pain in a subject in need of such treatment, said method comprising administering to the subject a therapeutically effective amount of a composition comprising a calcium channel modulator, wherein the modulator is a derivative of 5bk:

5bk

In some embodiments, the pain is tonic, neuropathic, and/or inflammatory pain. In some embodiments, the modulator is T-type calcium channel blocker. In some embodiments, the modulator is effective for blocking CaV3.1, CaV3.2 and/or CaV3.3 channels. In some embodiments, the modulator is according to any one of the following compounds:

1-159-2

3-14-3

3-25

In some embodiments, the modulator comprises the S- or R- enantiomer of said compounds:

-continued 1-159-2-S 1-159-2-R 3-14-3-R 3-14-3-S 3-25-S 3-25-R

In some embodiments, the modulator is 3-14-3-S:

3-14-3-S

In some embodiments, 3-14-3-S inhibits depolarization-induced $Ca^{2+}$ influx through T-type $Ca^{2+}$ channels. In some embodiments, 3-14-3-S decreases $Ca^{2+}$ current density and T-type $Ca^{2+}$ currents.

In some embodiments, the subject is a mammal. In some embodiments, mammal is a human. In some embodiments, the composition is administered in a dosage of about 0.001 mg/kg to 100 mg/kg of body weight. In some embodiments, the composition is administered at least once daily, at least once every other day, or at least once weekly. In some embodiments, wherein the composition is administered intranasally, intravenously, transdermally, or orally. In some embodiments, the composition comprising a calcium channel modulator according any of the compounds recited in FIG. 21A. In some embodiments, the calcium channel is a T-type calcium channel. In some embodiments, the modulator blocks CaV3.1, CaV3.2 and/or CaV3.3 channels.

In certain embodiments, the present invention provides a method of blocking a calcium channel, comprising exposing the calcium channel to a calcium channel modulator, wherein the modulator is a derivative of 5bk:

5bk

In some embodiments, the calcium channel is T-type calcium channel. In some embodiments, the modulator blocks CaV3.1, CaV3.2 and/or CaV3.3 channels.

In some embodiments, the modulator is according to any one of the following compounds:

1-159-2

3-14-3

-continued 3-25

In some embodiments, the modulator comprises the S- or R- enantiomer of said compounds:

1-159-2-S 1-159-2-R

23

-continued 3-14-3-R 3-14-3-S 3-25-S 3-25-R

24

In some embodiments, modulator is 3-14-3-S:

3-14-3-S

In some embodiments, 3-14-3-S inhibits depolarization-induced $Ca^{2+}$ influx through T-type $Ca^{2+}$ channels. In some embodiments, 3-14-3-S decreases $Ca^{2+}$ current density and T-type $Ca^{2+}$ currents.

In certain embodiments, the present invention provides a calcium channel modulator, wherein the modulator is according to one of the following compounds (recited in FIG. 21A):

2-103-1

2-147-1

25

26

2-153-2

2-195-1

2-153-1

2-197-2

2-147-3

2-203-2

2-105-2

2-203-1

27
-continued 2-145-1

3-32-1

3-32-3

3-32-2

28
-continued 3-32-5

3-32-6

3-10-1

3-10-3

29
-continued

30
-continued 3-32-4

3-8-1

3-8-2

3-9-1

3-8-3

3-32-9

3-32-8

3-1-1

31

-continued 3-13-1

3-13-2

3-13-3

3-14-2

32

-continued 3-14-3

3-5-2

2-199-2

3-6-2

33
-continued

34
-continued 2-183-1

1-157-2

3-25

1-157-1

3-4-2

2-149-1

1-159-2

3-2-1

2-143-2

2-193-2

2-193-1

2-201-2 and

-continued 3-3-2

In some embodiments, the modulator is the S- or R-en-antiomer of the compound. In some embodiments, the modulator is T-type calcium channel blocker. In some embodiments, the modulator is effective for blocking CaV3.1, CaV3.2 and/or CaV3.3 channels. In some embodiments, the modulator is effective for inhibiting depolarization-induced $Ca^{2+}$ influx through T-type $Ca^{2+}$ channels. In some embodiments, the modulator is effective for decreasing $Ca^{2+}$ current density and T-type $Ca^{2+}$ currents. In some embodiments, the modulator is effective for treating tonic, neuropathic, and/or inflammatory pain.

In certain embodiments, the present invention provides a composition for use in treating or preventing pain, said composition comprising a calcium channel modulator according to any one of the compounds recited in FIG. 21A, in a pharmaceutically acceptable carrier.

In certain embodiments, the present invention provides a method of treating or preventing pain in a subject in need of such treatment, said method comprising administering to the subject a therapeutically effective amount of a composition comprising a calcium channel modulator according to any one of compounds recited in FIG. 21A.

In certain embodiments, the present invention provides a composition for use in blocking a calcium channel, said composition comprising a calcium channel modulator according to any one of compounds recited in FIG. 21A.

In certain embodiments, the present invention provides a method of blocking a calcium channel, comprising exposing the calcium channel to a calcium channel modulator according to any one of the compounds recited in FIG. 21A.

The present disclosure further provides bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited. An exemplary advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment, prevention and/or amelioration of pain related to pan-T-type activity or specific CaV3.2 activity, or inhibition of pan-T-type activity or specific CaV3.2 activity.

In an additional aspect, the disclosure provides bifunctional or PROTAC compounds, which comprise an E3 Ubiquitin Ligase binding moiety (e.g., a ligand for an E3 Ubquitin Ligase or "ULM" group), and a moiety that binds a target protein (e.g., a protein/polypeptide targeting ligand or "PTM" group) (e.g., CaV3.1, CaV3.2, and CaV3.3) (e.g., CaV3.2) such that the target protein/polypeptide is placed in proximity to the ubiquitin ligase to effect degradation (and inhibition) of that protein (e.g., inhibit CaV3.1, CaV3.2, and CaV3.3 activity) (e.g., inhibit CaV3.2 activity). In certain embodiments, the PTM is any of the compounds as described herein showing inhibitory activity against CaV3.2 activity. In certain embodiments, the PTM is any of the compounds as described herein showing inhibitory activity against pan-T-type activity. In some embodiments, the ULM is a VHL, cereblon, mouse double minute 2 (MDM2), and/or inhibitor of apoptosis protein (IAP) E3 ligase binding moiety. For example, the structure of the bifunctional compound can be depicted as PTM-ULM.

The respective positions of the PTM and ULM moieties, as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as PTM-L-ULM, where PTM is a protein/polypeptide targeting moiety (e.g., any of the compounds as described herein showing inhibitory activity against pan-T-type activity) (e.g., any of the compounds as described herein showing inhibitory activity specifically against CaV3.2 activity), L is a linker, and ULM is a VHL, cereblon, MDM2, or IAP E3 ligase binding moiety binding moiety.

Such embodiments are not limited to a specific type of linker. In some embodiments, the linker group is optionally substituted (poly)ethyleneglycol having between 1 and about 100 ethylene glycol units, between about 1 and about 50 ethylene glycol units, between 1 and about ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical. In some embodiments, the linker is a substituted or unsubstituted polyethylene glycol group ranging in size from about 1 to about 12 ethylene glycol units, between 1 and about ethylene glycol units, about 2 about 6 ethylene glycol units, between about 2 and 5 ethylene glycol units, between about 2 and 4 ethylene glycol units.

The ULM group and PTM group may be covalently linked to the linker group through any group which is appropriate and stable to the chemistry of the linker. In exemplary aspects of the present invention, the linker is independently covalently bonded to the ULM group and the PTM group in certain embodiments through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain aspects where the PTM group is a ULM group, the target protein for degradation may be the ubiquitin ligase itself. In certain exemplary aspects, the linker may be linked to an optionally substituted alkyl, alkylene, alkene or alkyne group, an aryl group or a heterocyclic group on the ULM and/or PTM groups.

In certain embodiments, the compounds as described herein comprise multiple ULMs, multiple PTMs, multiple chemical linkers, or any combinations thereof.

In some embodiments, the present invention provides a method of ubiquitinating/degrading pan-T-type activity or specifically CaV3.2 activity in a cell comprising administering a bifunctional compound as described herein comprising an ULM and a PTM, in certain embodiments linked through a linker moiety, as otherwise described herein, wherein the ULM is coupled to the PTM and wherein the ULM recognizes a ubiquitin pathway protein and the PTM recognizes the target protein such that degradation of the target protein occurs when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

BRIEF DESCRIPTION OF THE DRAWINGS

FIG. TA-B: Synthesis of compounds by the Ugi-Azide four-component reaction. (A) Synthesis methodology. (B) List of compounds synthesized and tested. 5bk is also referred to as UAWJ111.

FIG. 3A-E: Primary screening using depolarization evoked $Ca^{2+}$ influx in DRG neurons identifies several antagonists of low and high voltage-activated calcium channels. Peak calcium responses of sensory neurons incubated overnight with 20 µM of the indicated compounds in response to 40 mM KCl (A) or 90 mM KCl (B) and normalized to 0.01% DMSO-treated control. N >78 neurons per condition from at least 3-4 rats each. Representative time courses of the change in 340 nm/380 nm ratio for the response of 4 representative neurons imaged in a preparation treated with 0.01% DMSO or 5bk. Because an increase in intracellular calcium induces an increase in 340-nm emission and a decrease in 380-nm emission, the simultaneous increase in 340 nm and decrease in 380-nm fluorescence emission associated with application of KCl is indicative an increase in intracellular calcium. KCl was added at the time indicated by the arrow. (C) The structure of 5bk is shown. (D) Scatter bar graph shows peak calcium responses of sensory neurons in response to a 40 mM KCl challenge. Neurons were incubated with vehicle (0.01% DMSO) or a 20 µM concentration of 5bk for various period of time as indicated: acutely (less than 5 min), 30 min, 2 hours, or 12-18 hours (overnight). (E) Concentration response curve for 5bk inhibition of calcium influx in response to a 40 mM KCl challenge; neurons were treated with vehicle (0.01% DMSO) or a 20 µM concentration of 5bk overnight in this experiment. P values of comparisons between treatments are as indicated; see statistical analysis described in Table 1.

FIG. 4A-I: Acute (<10 min) treatment with 5bk does not inhibit T-Type $Ca^{2+}$ currents in dorsal root ganglion (DRG) sensory neuron. (A) Representative family of traces of T-Type $Ca^{2+}$ currents from DRG sensory treated acutely (<10 min) with vehicle (0.01% DMSO) or 5bk (20 µM). Voltage protocol used to evoke the currents is shown. (B)

Figure 1B:
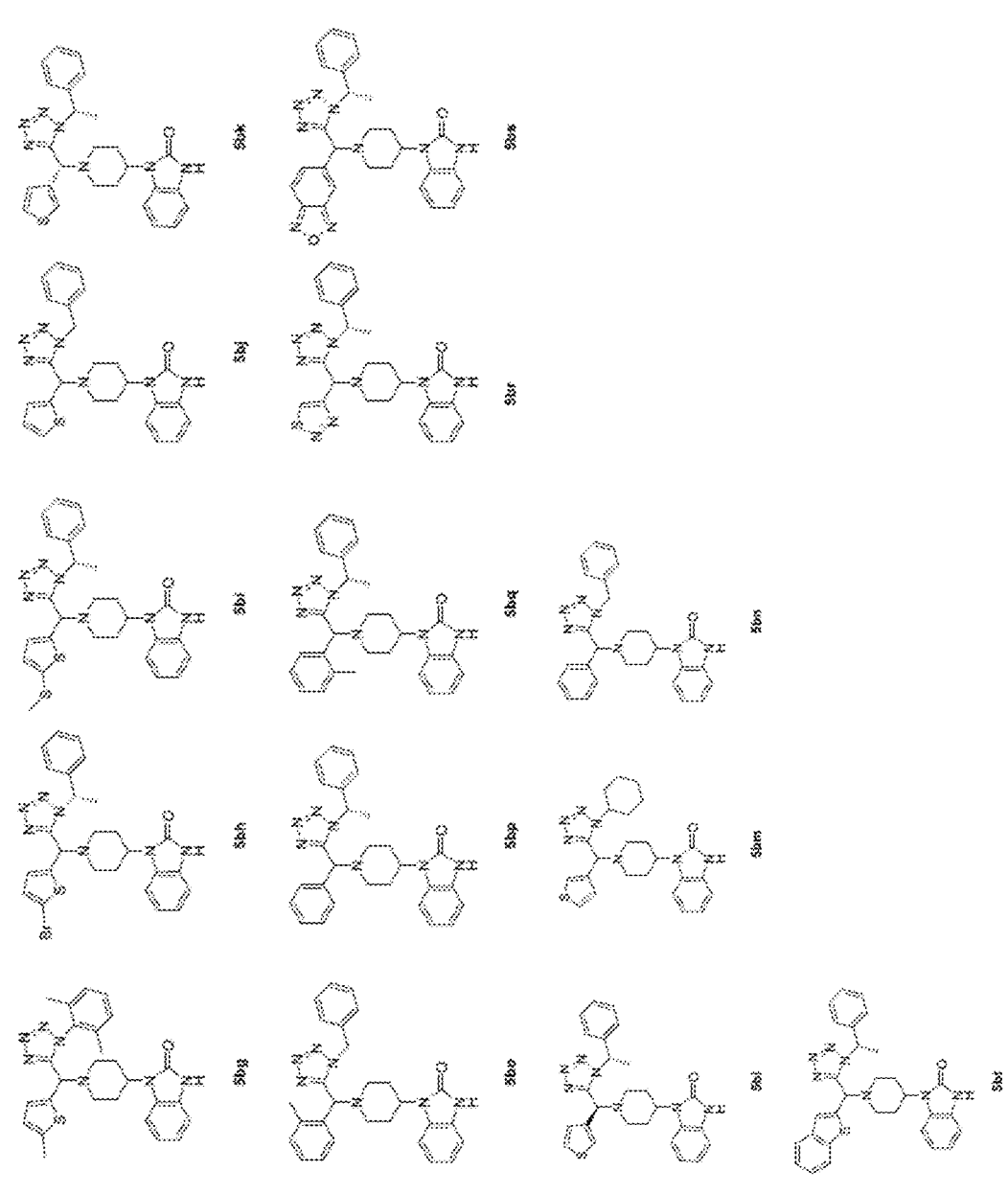

Summary of the normalized (pA/pF) T-Type calcium current density versus voltage relationship and (C) peak T-Type $Ca^{2+}$ current density at −10 mV (mean±SEM) from DRG sensory neurons treated as indicated. (D) Boltzmann fits for normalized conductance $G/G_{max}$ voltage relations for voltage dependent activation of T-type currents. (E) Time-dependent activation (10-90% rise time) from I-V curves and at −40 mV (F) in DRG cells shown calculated from the data in B. (G) Boltzmann fits for normalized conductance $G/G_{max}$ voltage relations for voltage dependent inactivation of sensory neurons treated as indicated. (H) Deactivating tail currents in DRG neurons treated acutely with vehicle (0.01% DMSO) or 5bk (20 μM) were fit with a single-exponential function. The resulting τ values are plotted. (I) Recovery from inactivation in indicated groups. Data are averaged and fitted by double exponential association (p values as indicated, Mann-Whitney test). All graphs show mean±s.e.m. with individual data points showed when possible.

FIG. 5A-K: 5bk inhibits T-Type $Ca^{2+}$ currents in dorsal root ganglion (DRG) sensory neurons. (A) Representative family of traces of T-Type $Ca^{2+}$ currents from DRG sensory treated overnight with vehicle (0.01% DMSO) or 5bk (20 μM). Voltage protocol used to evoke the currents is shown. (B) Summary of the normalized (pA/pF) T-Type calcium current density versus voltage relationship and (C) peak T-Type $Ca^{2+}$ current density at −10 mV (mean±SEM) from DRG sensory neurons treated as indicated. (D) Boltzmann fits for normalized conductance $G/G_{max}$ voltage relations for voltage dependent activation of T-type currents. (E) Inactivation τ, which is calculated from a single-exponential fit of the decaying portion of the current waveforms using a single-exponential equation: $y=A_1 \times e^{(-x/\tau 1)}+y_0$, where $A_1$ is the amplitude, $\tau_1$ is the decay constant, and $y_0$ is the offset. (F) This analysis was also isolated at −40 mV. (G) Time-dependent activation (10-90% rise time) from I-V curves and at −40 mV (H) in DRG cells shown calculated from data in B. (I) Boltzmann fits for normalized conductance $G/G_{max}$ voltage relations for voltage dependent inactivation of sensory neurons treated as indicated. (J) Deactivating tail currents in DRG neurons treated with vehicle (0.01% DMSO) or 5bk (20 μM) were fit with a single-exponential function. The resulting τ values are plotted. (K) Recovery from inactivation in indicated groups. Data are averaged and fitted by double exponential association (n=16-19 cells per condition). All graphs show mean±s.e.m. with individual data points showed when possible. P values of comparisons between treatments are as indicated; see statistical analysis described in Table 1.

FIG. 6A-T: 5bk does not inhibit high voltage-activated Ca, currents in dorsal root ganglion (DRG) sensory neurons. (A, F, K, P) Pharmacological isolation was achieved by the indicated cocktail of toxins/small molecules. The voltage protocol used to elicit the currents is also shown. (B, G, I, Q) Representative traces of DRG neurons treated overnight with 0.10% DMSO (control) or 20 μM 5bk (C, H, M, R) Summary of the normalized (pA/pF) HVA calcium current density versus voltage relationship and (D, I, N, S) peak HVA $Ca^{2+}$ current density at +20 mV (mean±SEM) from DRG sensory neurons treated as indicated. Boltzmann fits for normalized conductance $G/G_{max}$ voltage relations for voltage dependent activation and inactivation (E, J, O, T) of sensory neurons treated as indicated. Voltage dependent activation was assessed with the protocol shown in (E). The $V_{0.5}$ and slope (k) values for activation and inactivation are presented in FIG. 7. P values of comparisons between treatments are as indicated; see statistical analysis described in Table 1.

FIG. 7A-D: Boltzmann fits for normalized conductance $G/G_{max}$ voltage relations for voltage dependent activation and inactivation (data shown in FIG. 6) of the sensory neurons treated overnight as indicated with 0.01% DMSO or 5bk. Half-maximal activation and inactivation (Vu/2) and slope values (k) for activation and inactivation for the various HVA subtypes of calcium channels.

FIG. 8A-E: 5bk does not affect $Na^+$ currents in dorsal root ganglion (DRG) neurons. (A) Representative traces of $Na^+$ currents from DRG sensory neurons treated overnight with 0.1% DMSO (control) or 20 μM 5bk. Currents were evoked by 150 ms pulse between −70 and +60 mV. Summary of the normalized (pA/pF) sodium (B) current density versus voltage relationship and (C) peak $Na^+$ current density at −10 mV (mean±SEM) from DRG neurons treated as indicated. (D) Boltzmann fits for normalized conductance $G/G_{max}$ voltage relations for voltage dependent activation and inactivation of sensory neurons treated as indicated. $V_{1/2}$ values for activation and inactivation are indicated and were not significantly different between the treatment conditions (P>0.05, Mann-Whitney test). (E) Summary of the peak TTX-sensitive (F) $Na^+$ current density (mean±SEM) from DRG neurons treated as indicated. (p value as indicated, Mann-Whitney test). TTX-sensitive and TTX-resistant fractions were calculated as described in the Methods section.

Figure 9:
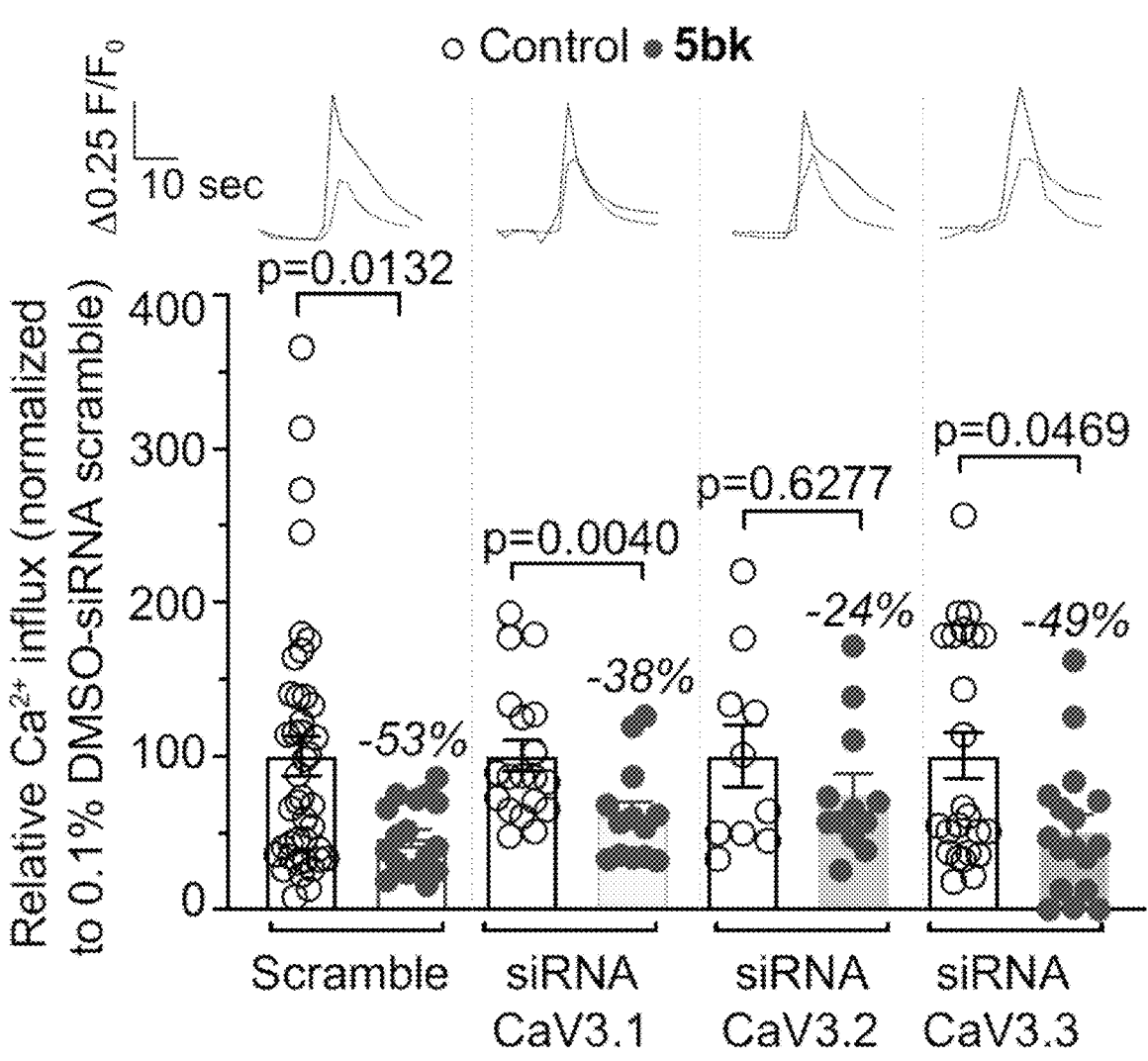

FIG. 9: Downregulation of CaV3.2 blocks 5bk-mediated inhibition of depolarization-evoked $Ca_2$ influx through T-type $Ca^{2+}$ channels. Dorsal root ganglion neurons were transfected during plating with a GFP construct and a scramble siRNA or with siRNAs against CaV3.1, CaV3.2 or CaV3.3. The bar graph shows normalized peak calcium response averages ±S.E.M. of DRG sensory neurons treated as indicated. Responses were normalized to that of DMSO (vehicle) in the siRNA scramble condition. Representative time courses of the change in 340 nm/380 nm ratio for the response of representative neurons imaged in a preparation treated with 0.01% DMSO or 5bk are shown above the bar graphs. These experiments were done in a blinded fashion. P values of comparisons between treatments (n=10-42 cells per condition) are as indicated; see statistical analysis described in Table 1.

FIG. 10A-I: Constellation pharmacology-based characterization of neuronal populations in DRG sensory neurons treated with 5bk. (A) Representative traces of sensory neurons treated overnight with 0.01% DMSO (vehicle) or (B) 20 μM concentration of 5bk responding to constellation pharmacology triggers (menthol (400 nM), histamine (50 μM), ATP (10 μM), AITC (200 μM), acetylcholine (1 mM), capsaicin (100 nM) and KCl (90 mM)) during $Ca^{2+}$ imaging. Each trace represents an individual neuron; a typical experimental trial records the responses of >300 neurons concurrently. (C) Number of overall functional DRG sensory neuronal classes as a result of treatment with DMSO or 5bk (20 μM). (D) Percentage of DRG sensory neurons that responded to indicated number of triggers. (E) Percentage of sensory neurons responding to major classes and (F) indicated subclasses of constellation triggers. (G) Average peak $Ca^{2+}$ response post-indicated treatment for DRG neurons following stimulation by major classes of constellation triggers. (H) Area under the curve is shown for calcium response in sensory neurons post-indicated treatment, after stimulation by major classes of constellation triggers. Area under the curve was calculated with Graphpad Prism software using the trapezoid rule. (I) Average peak KCl-evoked response of sensory neurons post-indicated treatment. P values of comparisons between treatments are as indicated; see statistical analysis described in Table 1. Abbreviations for constellation triggers are as follows: ACh=acetylcholine; AITC=allyl isothiocyanate; ATP=adenosine triphosphate; Hist=histamine; Ment=menthol; Cap=capsaicin; KCl=potassium chloride. Data was collected from a total of 5 independent experiments with an overall sample of 2002 for control conditions and 2902 for 5bk (20 μM).

Figure 11:
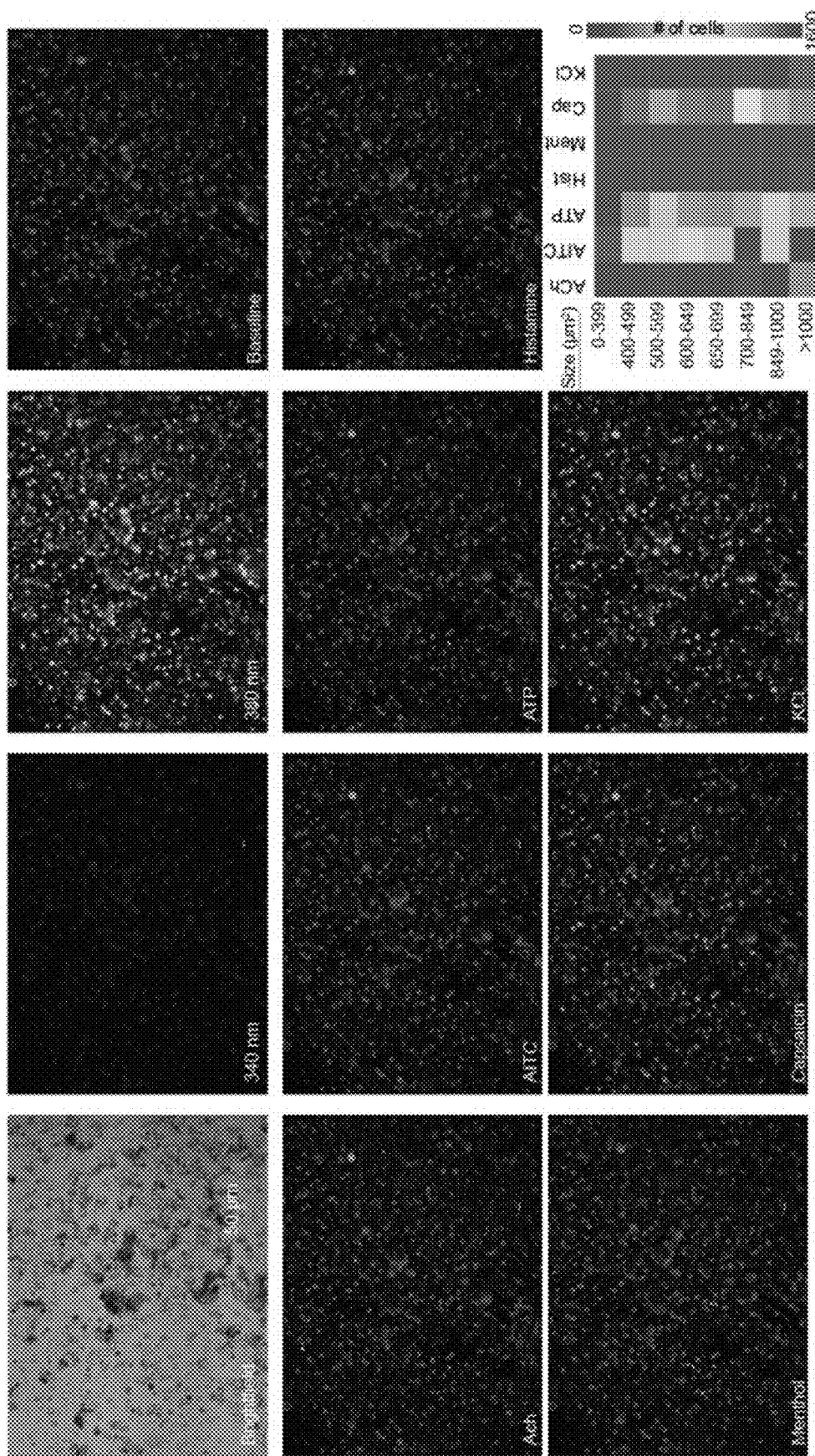

FIG. 11: Representative images of vehicle-treated DRG neurons post-challenge with constellation pharmacology triggers. Differential interference contrast (DIC) and pseudocolored fluorescent images of DRG neurons treated with vehicle, visualized for Fura2-AM before and after stimulations with each of the constellation triggers: menthol (400 nM), histamine (50 μM), ATP (10 μM), AITC (200 μM), acetylcholine (1 mM), capsaicin (100 nM) and KCl (90 mM)) during $Ca^{2+}$ imaging. Scale bar is 50 μm. Size heat map reports number of DRG neurons of indicated size (measured by neuronal area) responding to constellation triggers.

Figure 12:
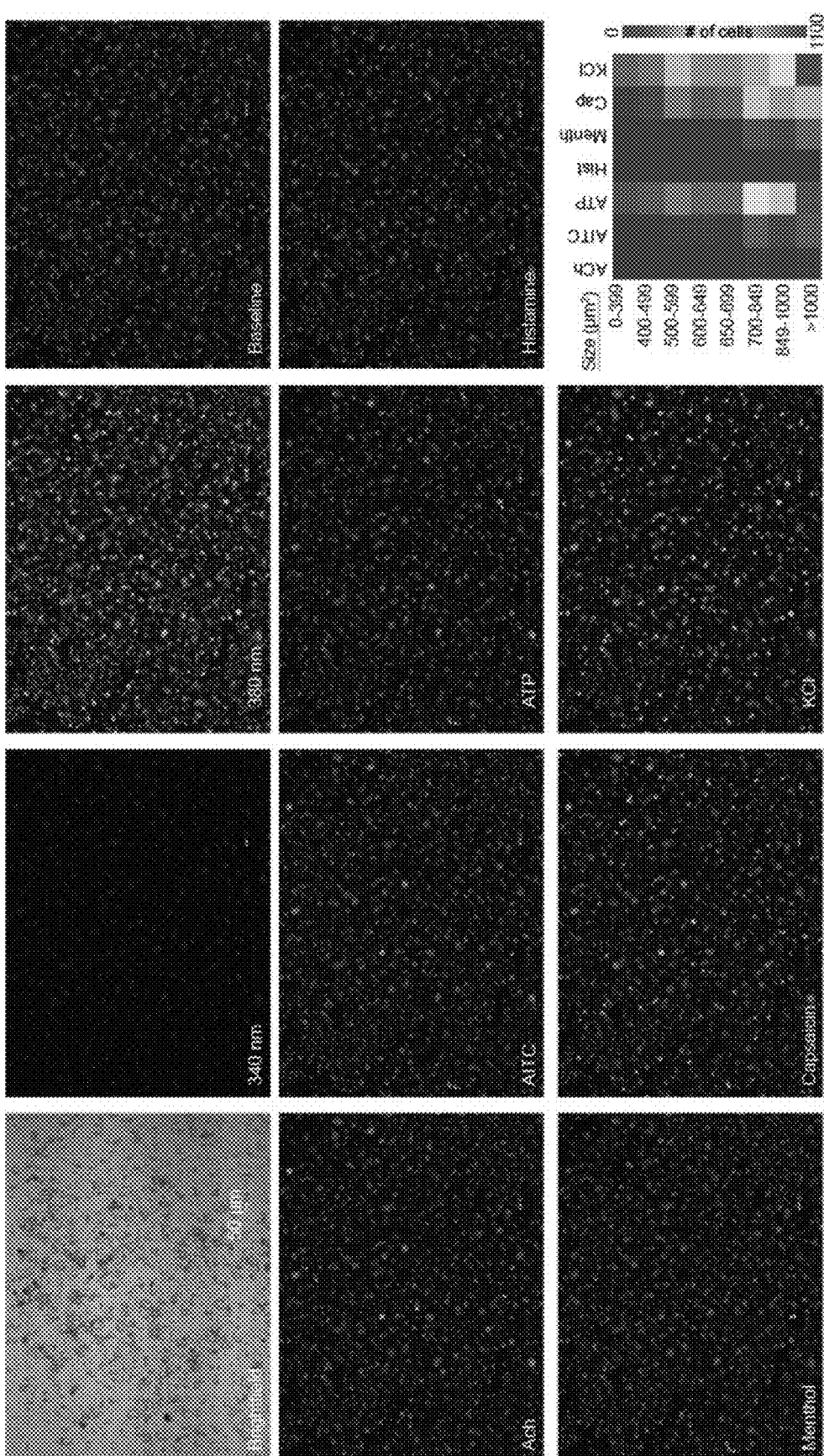
Figure 20A:
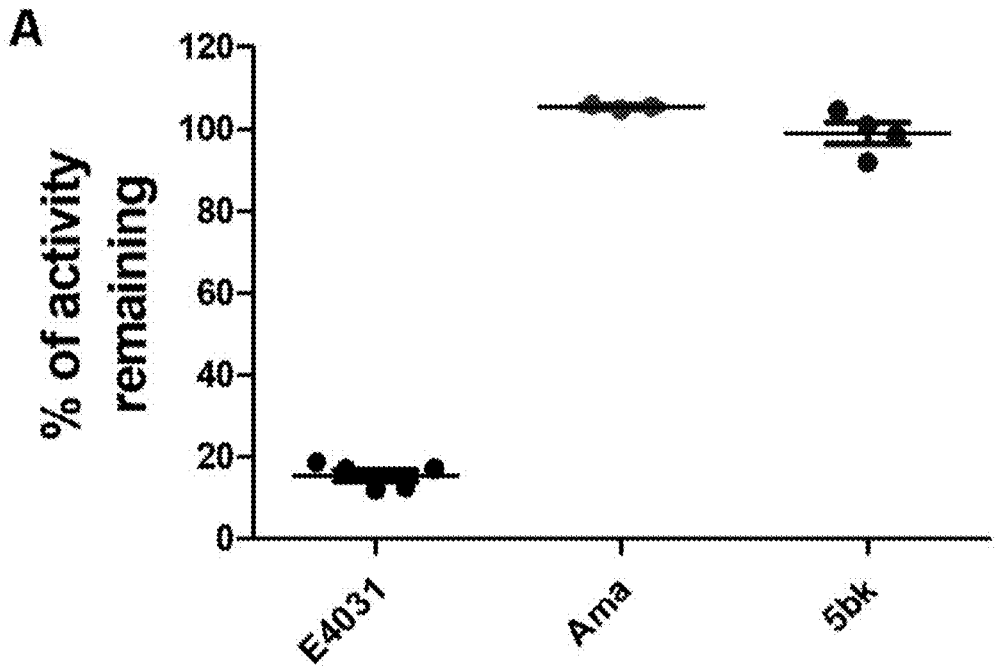
Figure 20B:
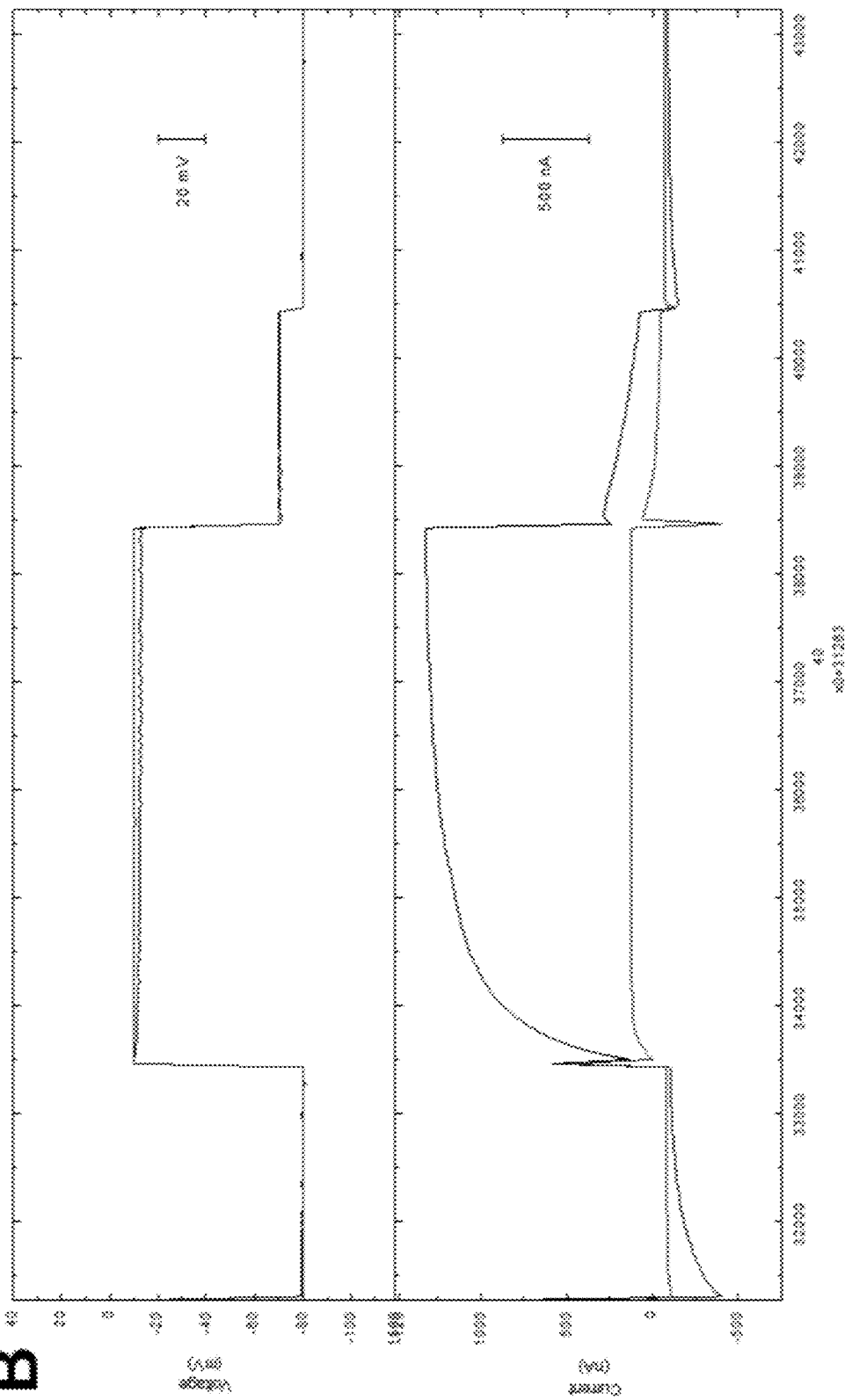
Figure 20C:
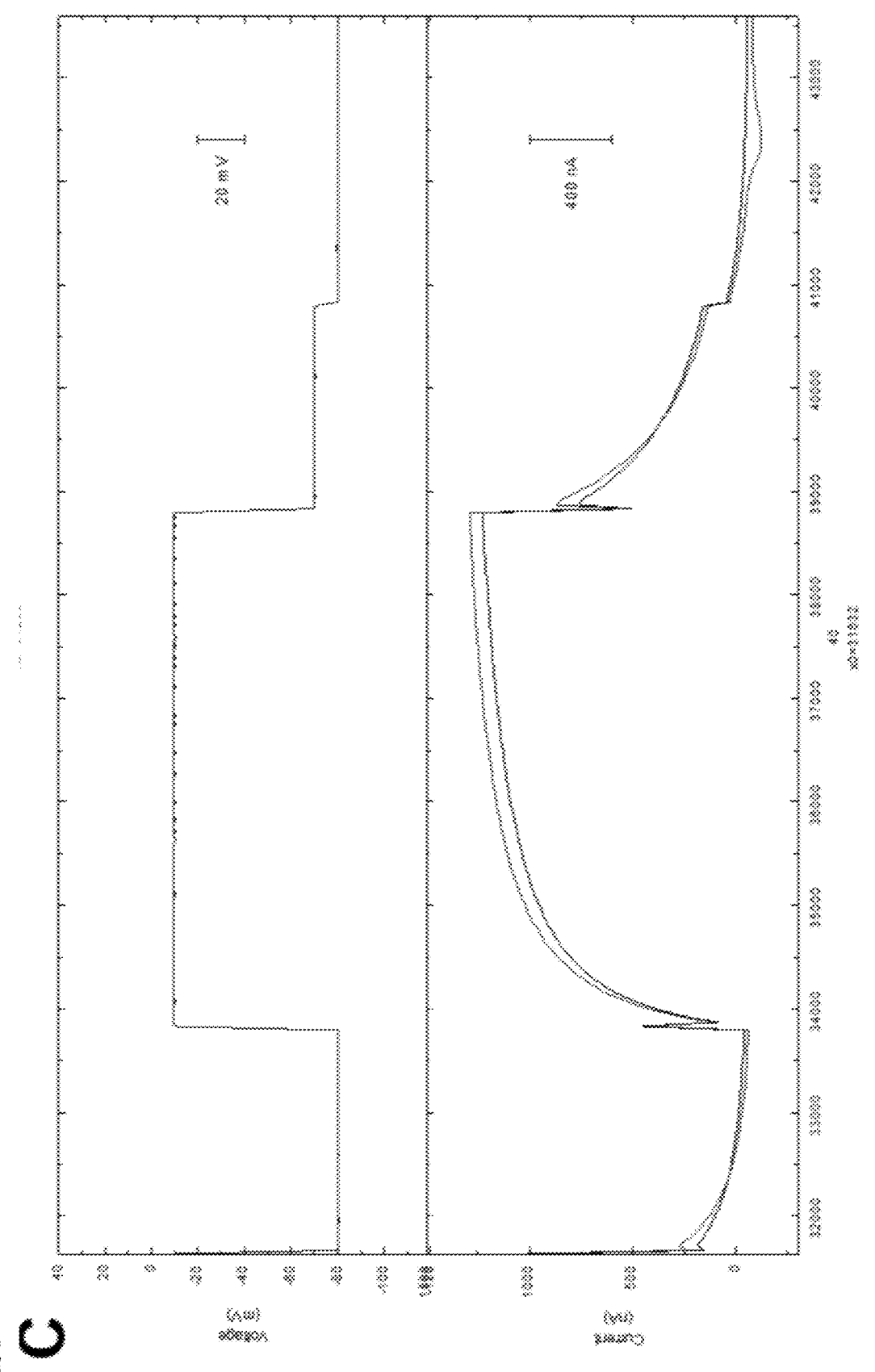
Figure 20D:
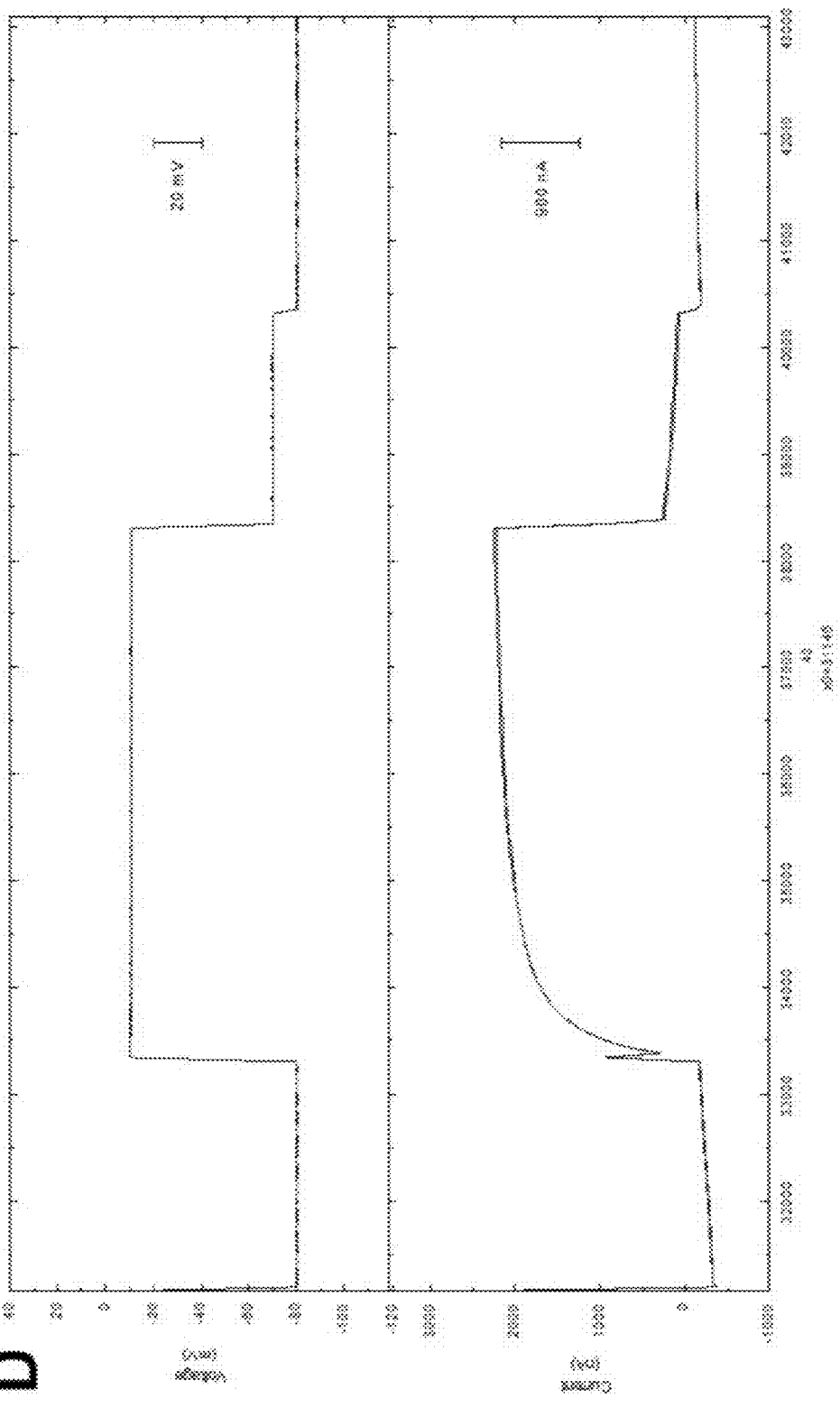

FIG. 12: Representative images of 5bk-treated DRG neurons post-challenge with constellation pharmacology triggers. Differential interference contrast (DIC) and pseudocolored fluorescent images of DRG neurons treated with 5bk (20 μM), visualized for Fura2-AM before and after stimulations with each of the constellation triggers: menthol (400 nM), histamine (50 μM), ATP (10 μM), AITC (200 μM), acetylcholine (1 mM), capsaicin (100 nM) and KCl (90 mM)) during $Ca^{2+}$ imaging. Scale bar is 50 μm. Size heat map reports number of DRG neurons of indicated size (measured by neuronal area) responding to constellation triggers.

FIG. 13A-C: 5bk does not bind to the opioid receptors. Competition radioligand binding was performed in CHO cells expressing the human mu/delta/kappa opioid receptors (MOR, DOR, or KOR, respectively) (see Methods for details). 5bk or a positive control compound was competed against $^3$H-diprenorphine in all 3 cell lines. Curves reported as the mean±SEM of the mean value from each individual experiment in n=3 independent experiments. The Ki also reported as the mean±SEM of the individual value from each of n=3 independent experiments. 5bk did not produce competition binding up to 10 μM in any cell line. (A) MOR: Naloxone Ki=43.3±1.9 nM. (B) DOR: Naloxone Ki=48.1±9.1 nM. (C) KOR: U50,488 Ki=12.7±0.6 nM. See statistical analysis described in Table 1.

FIG. 14A-C: 5bk decreases spontaneous excitatory synaptic transmission in substantia gelatinosa neurons. (A) Representative traces recorded from control (0.1% DMSO) and 5bk (25 μM)-treated groups. (B) Spontaneous excitatory post synaptic current (EPSC) amplitudes as a result of treatment with DMSO or 5bk. (C) Spontaneous EPSC frequency as a result of treatment with DMSO or 5bk. P values of comparisons between treatments (n=17-18 per condition) are as indicated; see statistical analysis described in Table 1.

Figure 15:
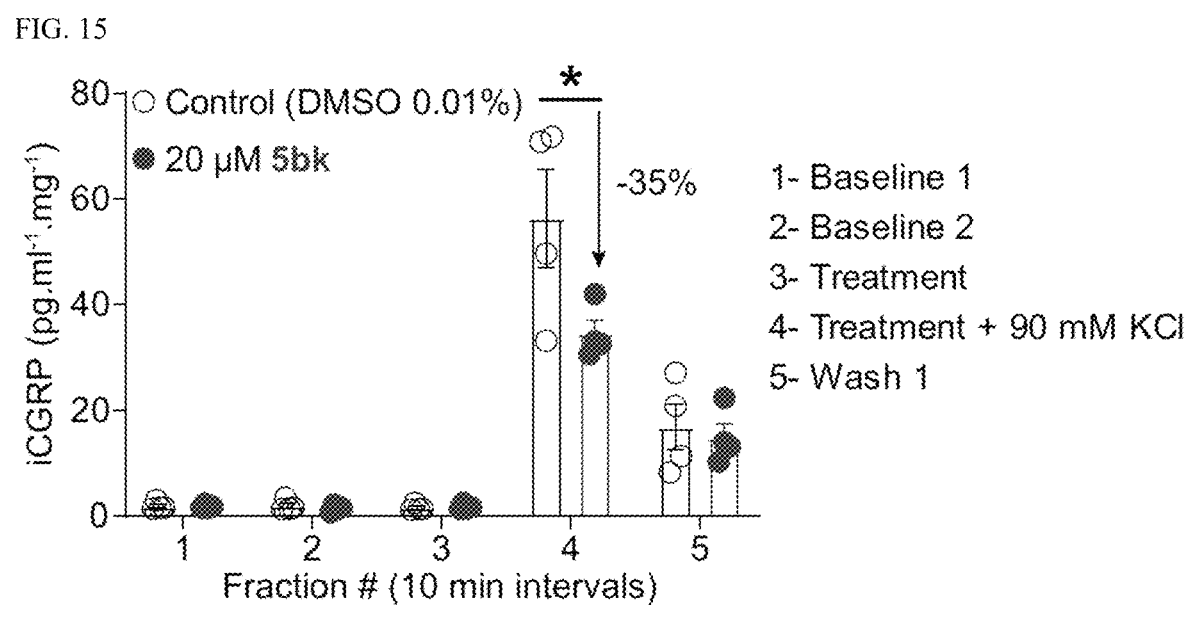

FIG. 15: *5bk* decreases evoked CGRP release. Spinal cords from adult rats (n=4 per condition) were used to assess potassium chloride (KCl, 90 mM)-induced calcitonin gene related peptide (CGRP) release from nerve terminals. KCl increased CGRP release in control rat spinal cords, which was significantly higher than in cords from 5bk-treated rats (* p<0.05 vs. control; two-way ANOVA post hoc Sidak's test). P values of comparisons between treatments are as indicated; see statistical analysis described in Table 1.

FIG. 16A-I: GP120, paclitaxel, and spinal nerve ligation induced nociceptive behaviors are reduced upon treatment with 5bk. (A) Rats received spinal nerve ligation (SNL) injury with allodynia measurement on the left hind paw. Paw withdrawal thresholds were significantly decreased 7 days after surgery. 5bk (2 μg/5 μL) or vehicle (saline) were injected into the intrathecal space and PWTs measured. Paw withdrawal thresholds were significantly reversed at the indicated times after injection of 5bk (n=6; *p<0.05; two-way ANOVA with a Student-Neuman-Kuels post hoc test). (B) Data from D are transformed and presented as mean±s.e.m. percentage of maximal anti-allodynia (see Methods). (C) Area under the curve (AUC), using the trapezoid method, for PWT. Statistical significance is indicated by asterisks (*p<0.05, one-way analysis of variance with Tukey's post hoc analysis) in comparison to vehicle-treated rats. (D) Paw withdrawal threshold (PWTs) of adult rats (n=7) was measured 15 days after 3 intrathecal injections of glycoprotein-120. Rats were treated with saline (vehicle) or 5bk (2 μg/5 μL, intrathecal) as indicated. Asterisks indicate statistical significance compared with animals treated with saline (*p<0.05; 2-way ANOVA with a Dunnet's hoc test). (E) Data from A are transformed and presented as mean±s.e.m. percentage of maximal anti-allodynia (see Methods). (F) Area under the curve was derived as indicated before using Graphpad prism. Statistical significance is indicated by asterisks (*p<0.05, Mann-Whitney) in comparison to vehicle-treated rats. (G) Paw withdrawal threshold of adult rats (n=7) was measured 15 days after 4 intraperitoneal injections of paclitaxel. Rats were treated with saline (vehicle) or 5bk (2 μg/5 μL, intrathecal) as indicated. Data from G are transformed and presented as mean s.e.m. percentage of maximal anti-allodynia (see Methods). Asterisks indicate statistical significance compared with tissue treated with saline (*p<0.05; 2-way ANOVA with a Dunnet's post hoc test). (I) Area under the curve was derived again as indicated before using Graphpad prism. Statistical significance is indicated by asterisks (*p<0.05, Mann-Whitney) in comparison to vehicle-treated rats. Exact p values of comparisons between treatments are described in Table 1.

FIG. 17A-B: Treatment with 5bk does not induce motor deficits or alter anxiety levels. (A) Rats (n=6) were subjected to the rotarod performance test as previously described in the Methods in order to test for motor deficits. Vehicle and 5bk-treated animals remained on the rotarod for an average of 172±7.3 and 170±9.6 seconds (cutoff 180 seconds), respectively, when tested over the course of 300 minutes. No significant motor deficits were noted in comparison to vehicle-treated animals. (B) Rats (n=7) were subjected to the elevated plus maze (EPM) test as detailed (see methods); the anxiety index, integrates measurement of times and entries of the animals into the open and closed arms of the EPM, and is shown both pre- and post (1 hour) injection of either 0.01% DMSO (vehicle) or 5bk (2 μg/5 μL, intrathecal) as indicated. See statistical analysis described in Table 1.

FIG. 18A-C: Docking of 5bk and Z944 on the Cav3.2 structure. (A) Ribbon diagram of CaV3.2 channel modeled on the CaV3.1 cryoEM structure (PDB ID 6kzp [94]) using Phyre2 [39]. Aligned inhibitor Z944 from CaV3.1 structure shown in gray and docked 5bk in green sticks representation. (B) Surface representation of ligand binding pocket showing overlap of the Z944 binding mode and 5bk docked pose. (C) Interactions within 4 A of 5bk with polar and nearest ring contacts indicated by dashes. 5bk was prepared with LigPrep and docked with Glide (Schrodinger Release 2019-4) [24] in Xtra Precision mode (docking score: −6.7).

FIG. 19A-B: (A) 2-D similarity of 5bk (left) and Z944 (right) with common pharmacophore features color-coded in red and blue, respectively. (B) 3-D overlay of energy-minimized conformers of 5bk and Z944.

FIG. 20A-D: hERG channel was expressed in oocytes and the current was recorded with and without 100 μM of the indicated compounds. (A) Summary data of % hERG current remaining with the various compounds. E4031, a known hERG channel blocker, was used as a positive control (see, Vandenberg J I, et al., Physiol Rev 2012; 92(3):1393-1478). Amantadine was used as a negative control. Representative traces from oocytes treated with vehicle (0.01% DMSO, black trace) or E4031 (B, red trace), Ama (C, red trace), or 5bk (D, red trace).

Figure 21A:
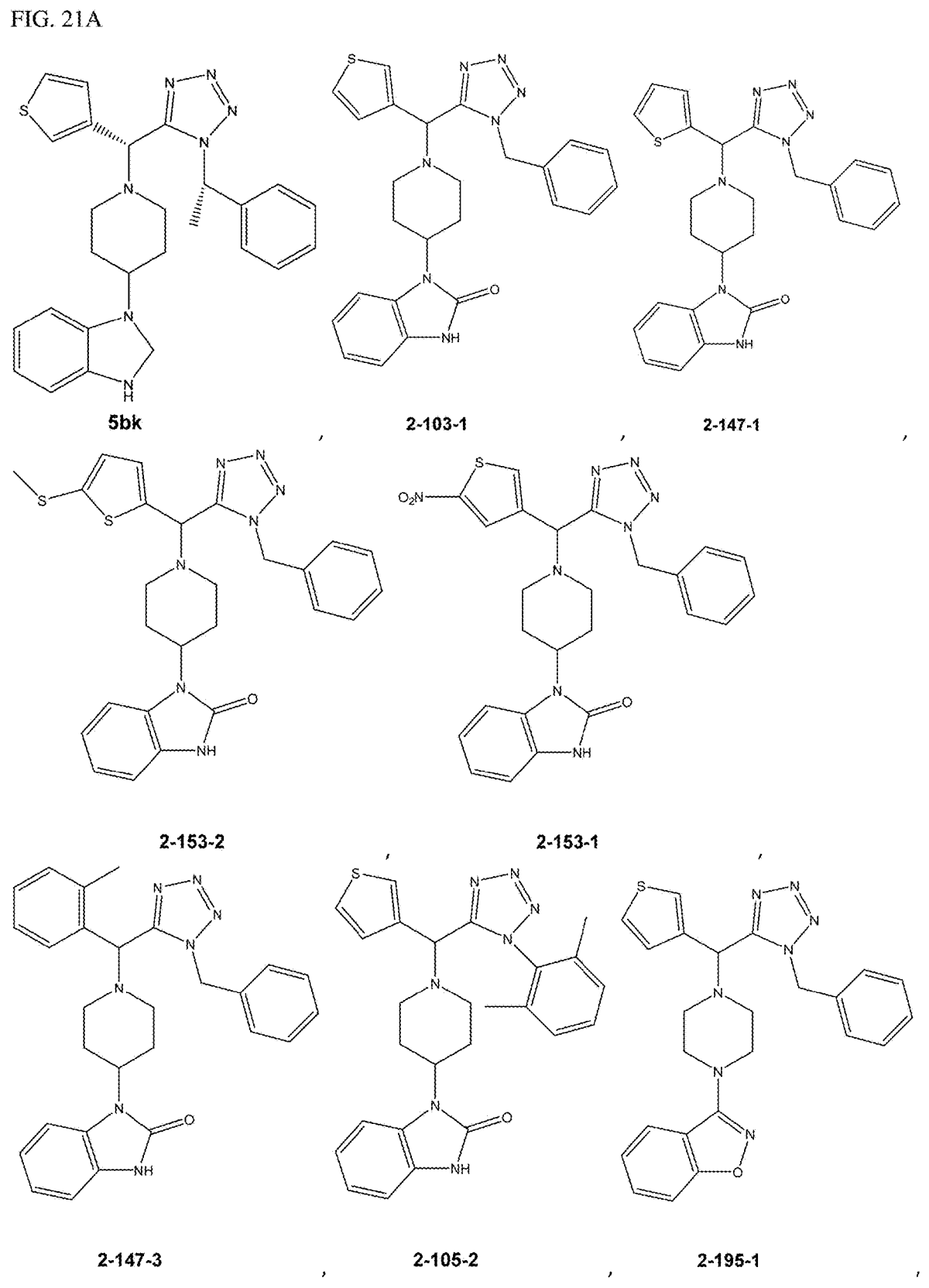
Figure 21A:
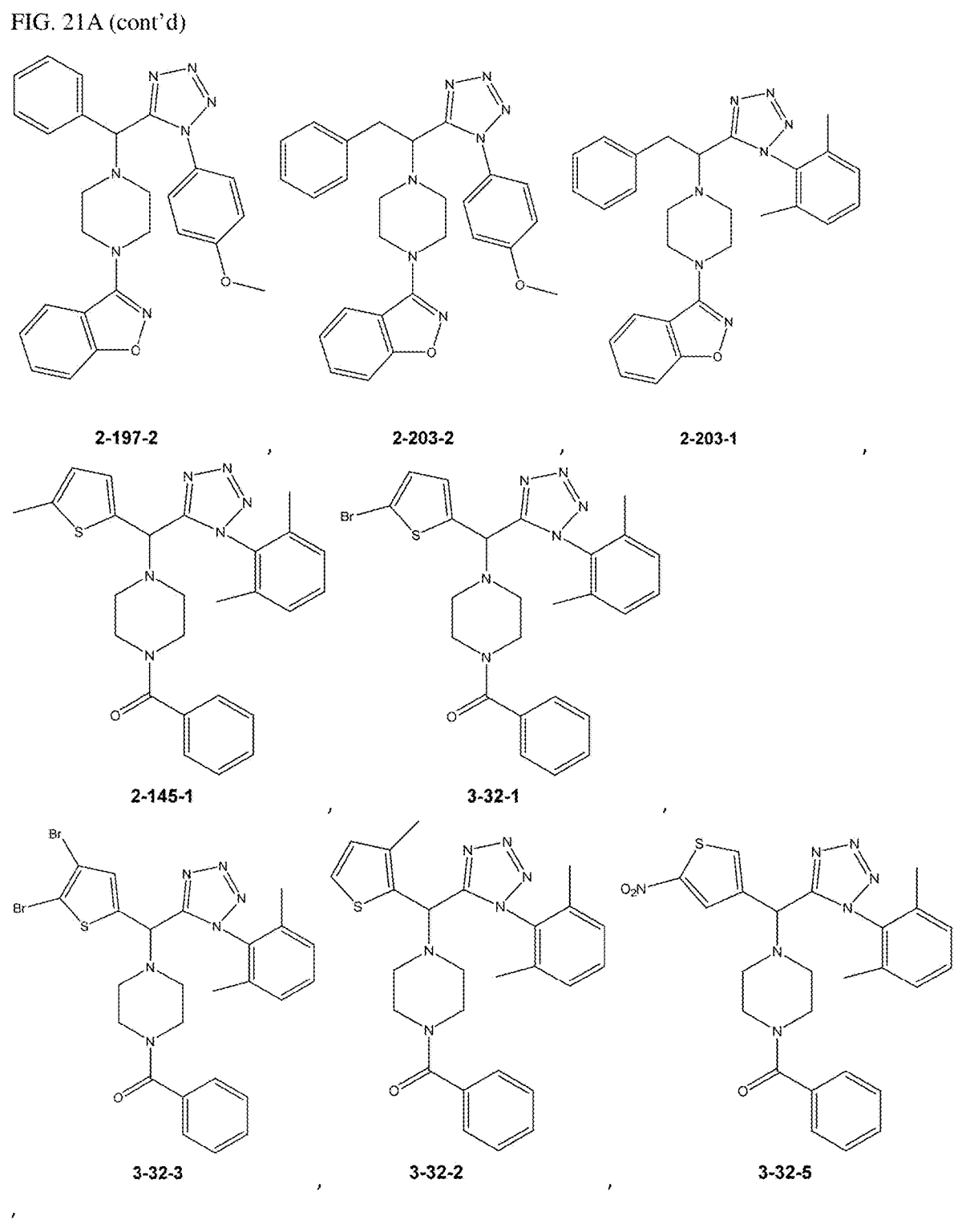
Figure 21A:
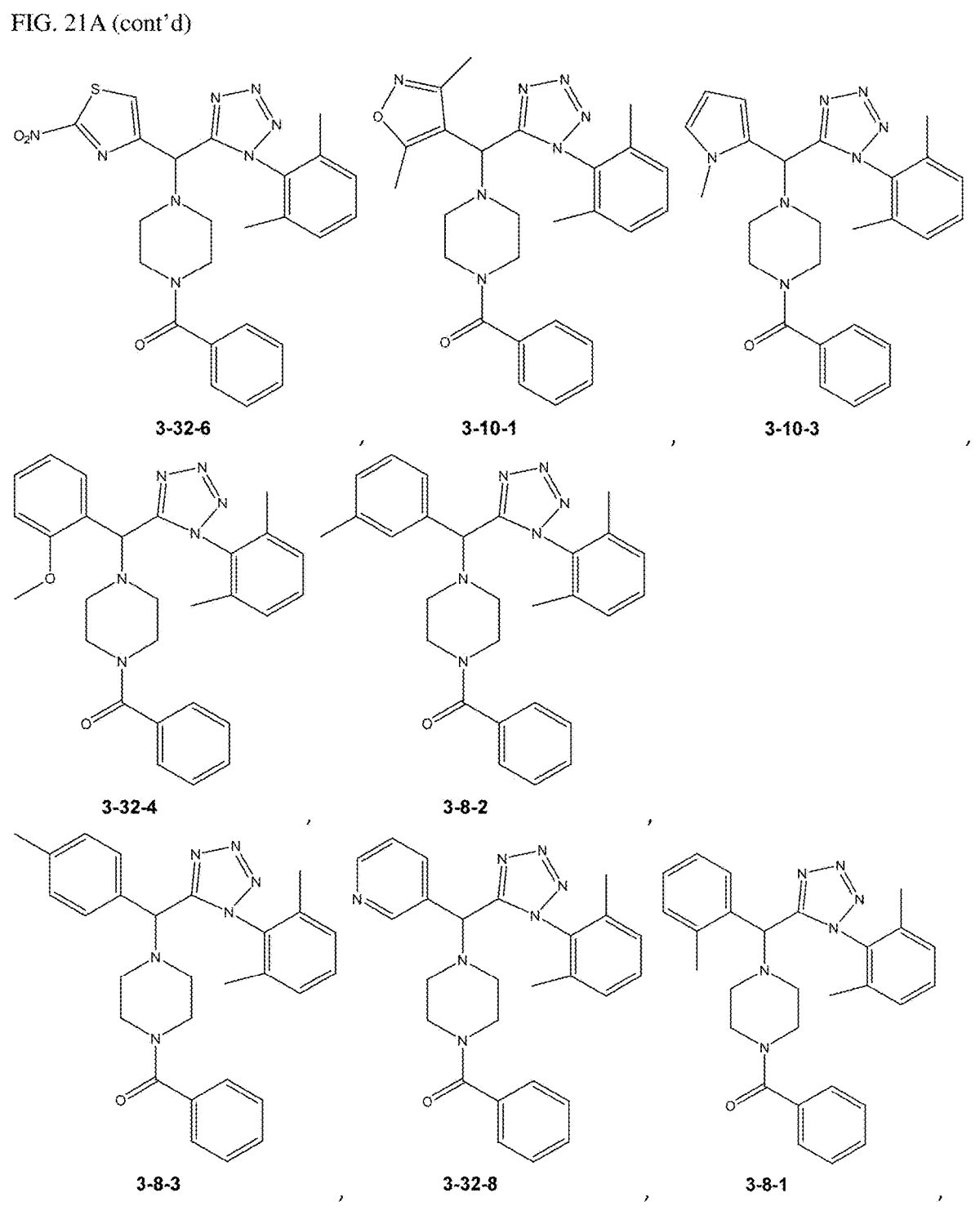
Figure 21A:
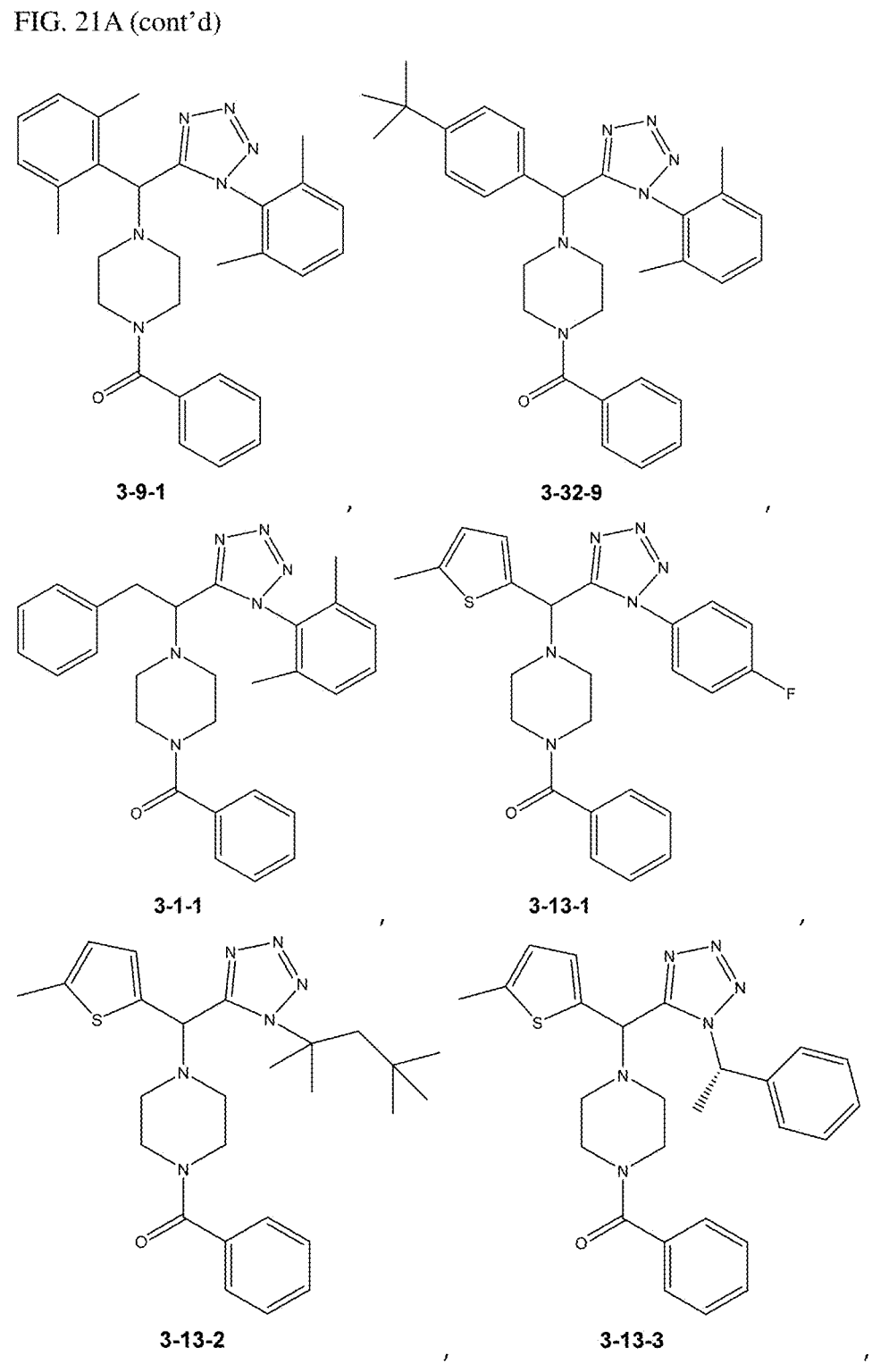
Figure 21A:
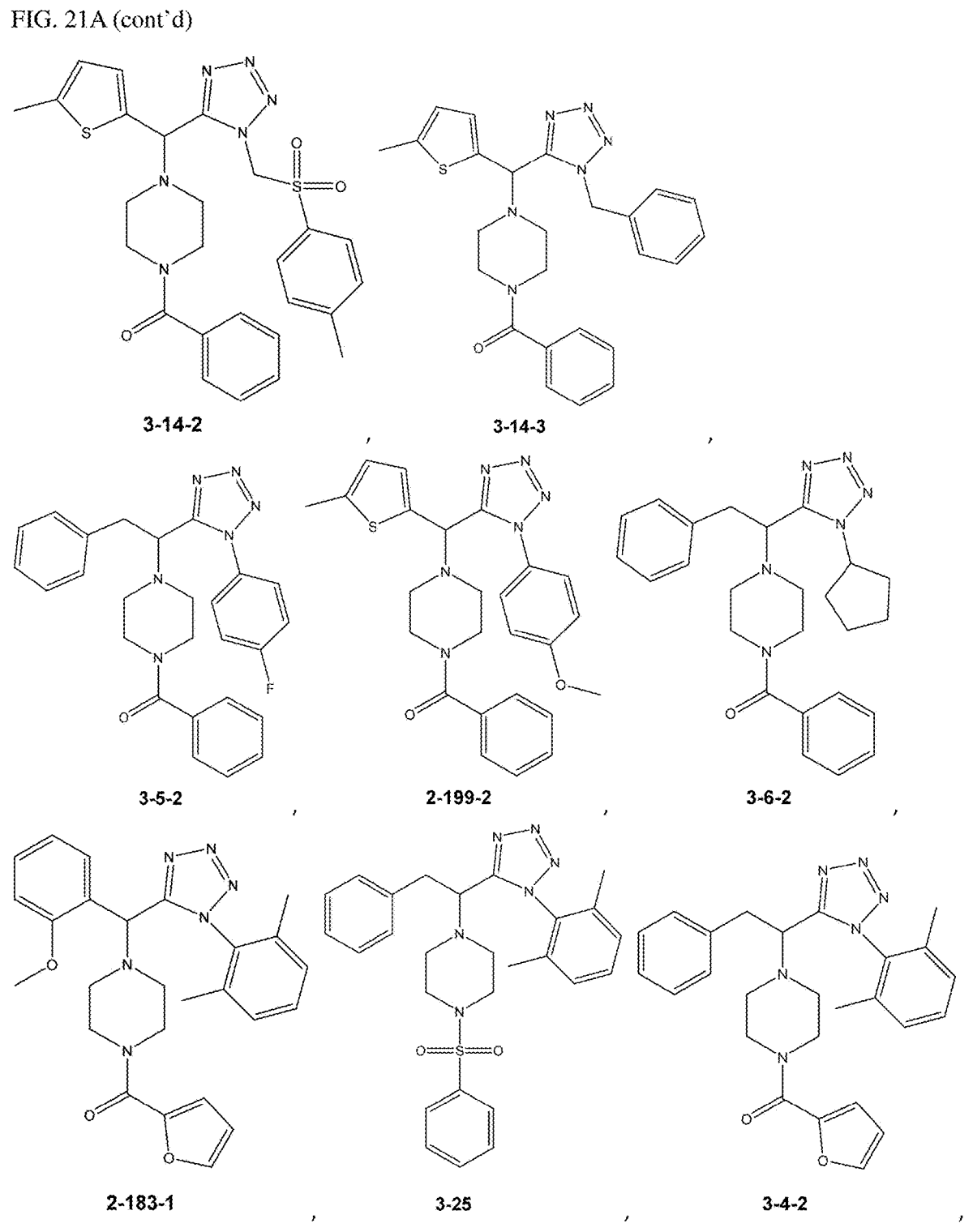
Figure 21A:
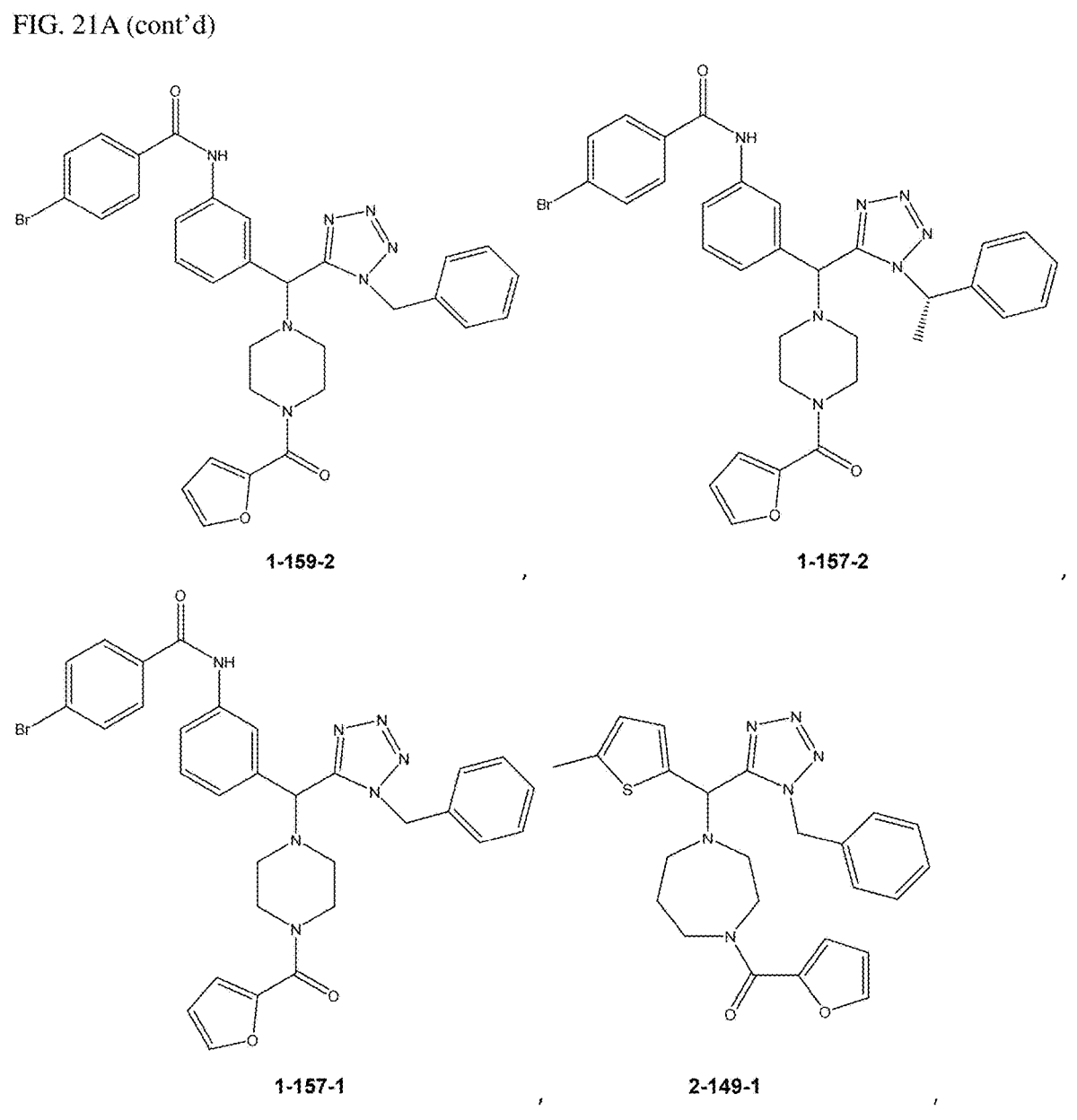
Figure 21A:
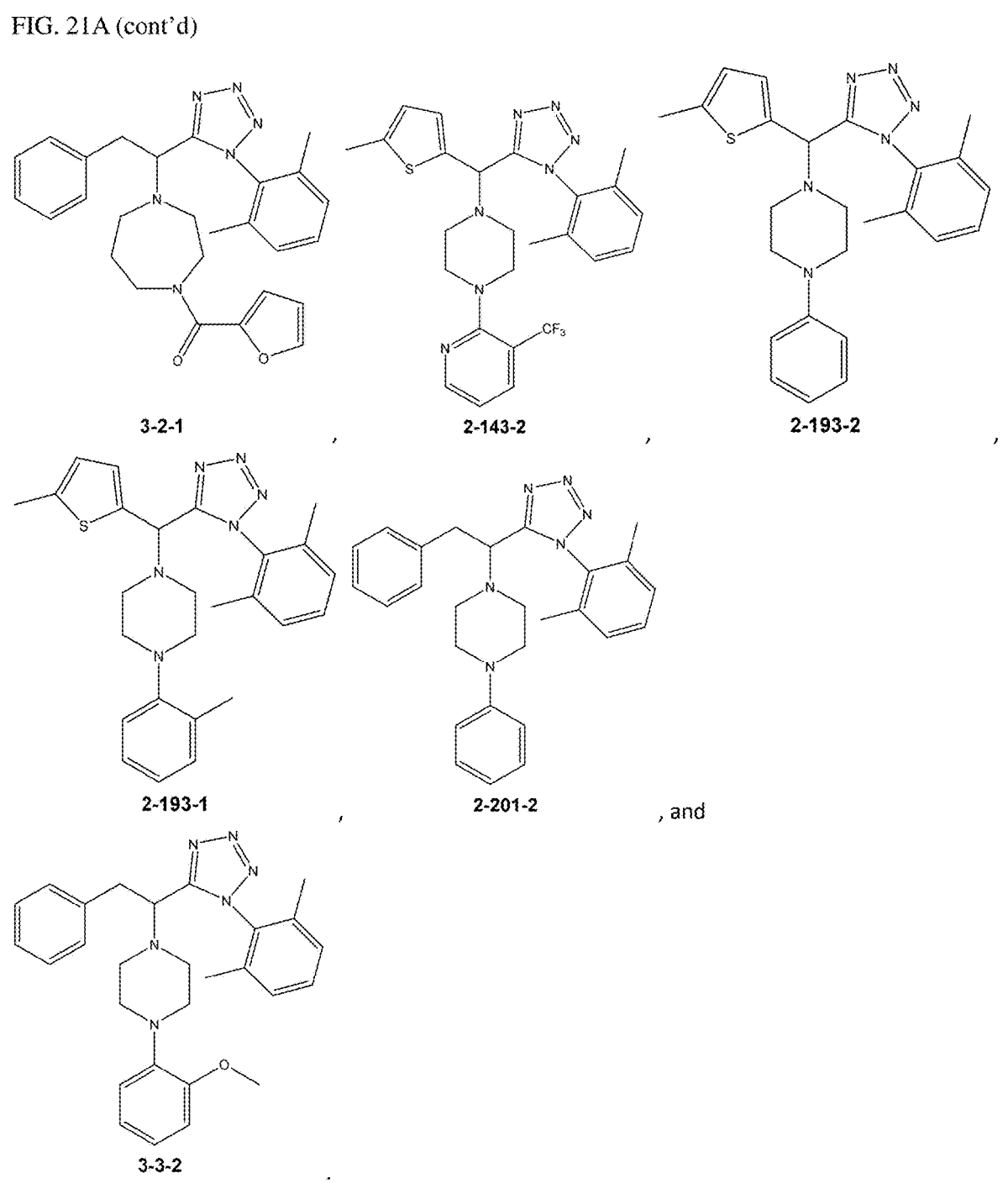
Figures 21B, 21C:
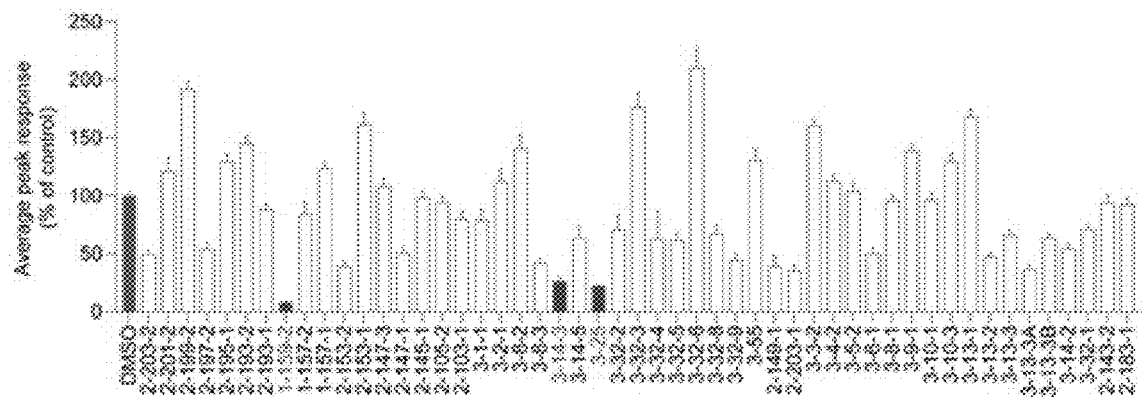
Figure 21D:
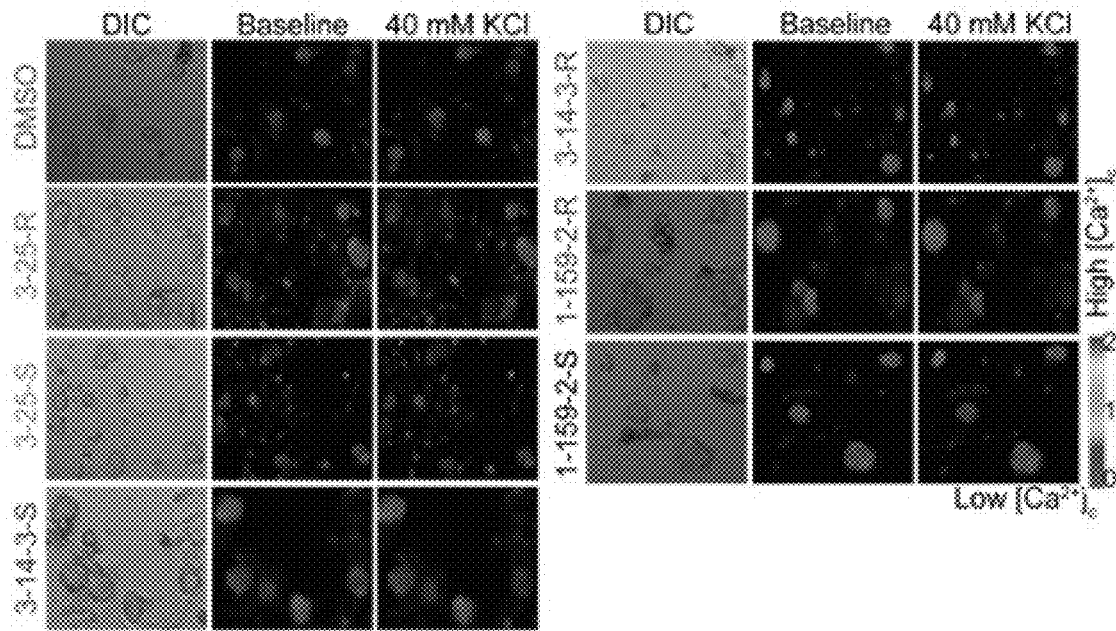
Figure 21E:
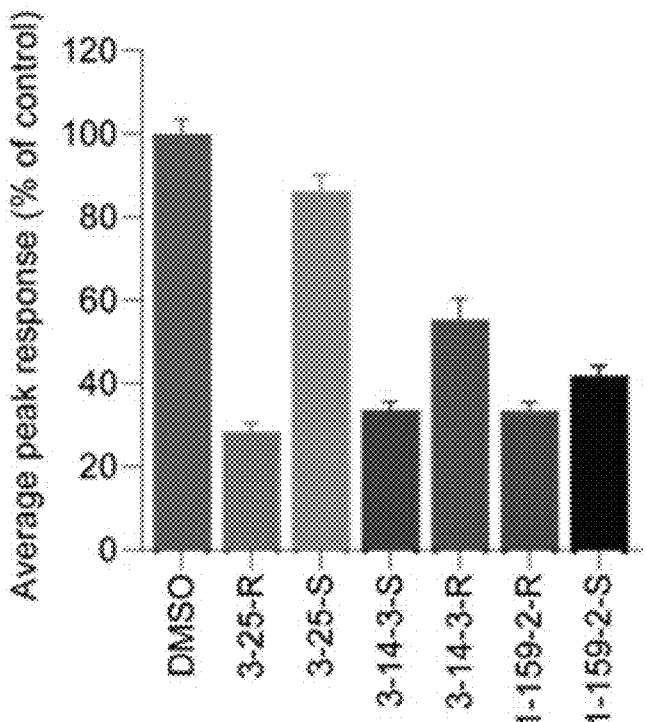

FIGS. 21A-E show compound screenings using depolarization-induced $Ca^{2+}$ influx in DRG neurons to identify various modulators of low voltage-activated $Ca^{2+}$ channels. FIG. 21A shows a focused tetrazole compound library used for the screening in the depolarization-induced $Ca^{2+}$ influx assay in DRG neurons. FIG. 21B shows normalized average peak $Ca^{2+}$ response of DRG sensory neurons incubated overnight with 10 μM of the indicated compounds in response to 40 mM KCl (n=46-1042 cells). FIG. 21C shows chemical structures of the screening hits. The absolute stereochemistries of the enantiomers were assigned based on the relevant elution times in chiral HPLC. FIG. 21D shows differential interference contrast (DIC) and pseudocolored fluorescent images visualized for Fura2-AM in DRG neurons. Neurons were sequentially stimulated with 40-mM KCl for 15 seconds after an initial 1-minute baseline measurement, and response was measured for 3 minutes after each challenge. In the fluorescence scale, high intracellular $[Ca^{2+}]$ is indicated in red. FIG. 21E shows the average peak response to 40 mM KCl of DRG neurons incubated overnight with 10 μM of the indicated compounds (n=330-1099 neurons). Responses were normalized to that of the DMSO group. Data indicate mean±SEM.

FIGS. 22A-D show data for calcium currents reduced by compounds 3-25-R and 3-14-3-S in DRG neurons. FIG. 22A shows representative calcium current traces recorded from small—to medium-sized DRGs incubated overnight with 10 μM 3-25-R and 3-14-3-S as indicated in the figure. Currents were evoked by 200-ms pulse between −70 and +60 mV. FIG. 22B shows double Boltzmann fits for current density-voltage curve. FIG. 22C is a summary of bar graph showing peak calcium current densities (pA/pF). FIG. 22D shows Boltzmann fits for voltage-dependent activation and inactivation as shown. N=12-17 cells; error bars indicate mean±SEM; p values as indicated; One-way ANOVA with the Tukey post hoc test.

FIGS. 23A-C show 3-14-3C1 inhibiting T-type calcium channels in heterologous cells. FIGS. 23A-24B show representative calcium current traces before (gray) and after application of 50 μM 3-25-R (orange) and 3-14-3-S (purple). FIG. 23C show concentration-response curves of 3-14-3-S in cells expressing CaV3.1 ($IC_{50}$=23.02 μM), CaV3.2 ($IC_{50}$=35.58 μM) and CaV3.3 ($IC_{50}$=26.27 μM). Left: CaV3.1, middle: CaV3.2, and right: CaV3.3. N=3-8 cells; error bars indicate mean±SEM.

FIGS. 24A-E show raw behavior data of the effects of a single administration (0.4 μg/μl, i.t.) of 3-14-3-S in ALGO-Gram™. FIG. 24A shows raw behavior for acute and tonic pain area. In healthy rats, nociceptive threshold (g) and latency (sec) were determined using the paw pressure test and the tail flick test. The cut off was 680 g and 10 sec respectively. For the acetic acid test and formalin test, the number of abdominal cramps and paw licking time (sec)

were measured. FIG. 24B shows raw behavior for neuropathic pain area. In the Bennett model of peripheral mononeuropathy, paw pressure test was employed to assess nociceptive threshold (g; cut off: 680 g). For oxaliplatin-induced neuropathy, paw immersion test was used to measure the reaction time (sec). FIG. 24C shows raw behavior for inflammatory pain area. In carrageenan-induced mechanical hyperalgesia, paw pressure test was applied to measure nociceptive threshold (g; cut off: 680 g). For the kaolin-induced arthritis model, gait score was reported. FIG. 24D shows raw behavior for post-operative pain area. For the Brennan model of incisional pain, paw withdrawal threshold was measured with electronic Von Frey test. FIG. 24E shows raw behavior for visceral pain area. Trinitrobenzene sulfonic acid (TNBS) induced chronic colonic hypersensitivity and colonic distension threshold was assessed (mmHg; cut off: 75 mmHg).

FIGS. 25A-C show 3-14-3-S docking. FIG. 25A is a ribbon diagram of human CaV3.1 structure with central cavity shown as gray surface (PDB ID: 6kzp [40]) viewed down fenestrations II-III to IV-I. FIG. 25B is a top view of CaV3.1 surface (cutaway view) showing the central cavity and three open fenestrations. Bound Z944 and lipid shown in black and gray CPK, docked 3-14-3-S shown in purple CPK. FIG. 25C is a close up view of top docked pose and contacts within 4 Å. Residues in red are not conserved in CaV1.x or CaV2.x isoforms. Asterisks denote residues residing in fenestration II-III. The Glide docking score was −7.2 kcal/mol.

DEFINITIONS

As used herein, the terms "treat", "treating", or "treatment" refer to both therapeutic treatment and prophylactic or preventative measures, with the objective of preventing, reducing, slowing down (lessen), inhibiting, or eliminating an undesired physiological change, symptom, or disorder, such as the development or spread of pain. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with the composition comprising the calcium channel modulator of the invention may include reduction of pain. "Treatment" can also mean prolonging survival as compared to expected survival if not receiving treatment. Those in need of treatment include those already with a condition or disorder as well as those prone to have a condition or disorder or those in which a condition or disorder is to be prevented or onset delayed. Optionally, the subject or patient may be identified (e.g., diagnosed) as one suffering from the disease or condition (e.g., pain) prior to administration of the modulator of the invention.

A "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disease or condition being treated and the severity of the disease or condition; the specific composition employed; the age, body weight, general health, sex and diet of the patient; the time of administration; the route of administration; the rate of excretion of the specific compound employed; the duration of the treatment; drugs used in combination or coincidental with the specific modulator employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adults and newborn subjects, as well as fetuses, whether male or female, are intended to be included. A "patient" is a subject afflicted with a disease, disorder, or condition, (e.g., pain). The term "patient" includes human and veterinary subjects.

The terms "administering" and "administration" refer to methods of providing a pharmaceutical composition to a subject. Such methods are well known to those skilled in the art. Pharmaceutical compositions can be administered in a number of ways depending on whether local or systemic treatment is desired, and on the area to be treated. Administration include, but is not limited to, administering the compositions topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, intrathecally, extracorporeally, transdermally, or the like.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient (e.g., the calcium channel modulator) and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution may be about 5 to about 8, such as from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more desirable depending upon, for instance, the route of administration and concentration of composition being administered. Other compounds can be administered according to standard procedures used by those skilled in the art.

Pharmaceutical compositions can include additional carriers, as well as thickeners, diluents, buffers, preservatives, surface active agents and the like in addition to the compounds disclosed herein. Pharmaceutical those can also include one or more additional active ingredients such as antimicrobial agents, anti-inflammatory agents, anesthetics, and the like.

For example, pharmaceutical compositions for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions for topical administration include but are not limited to, ointments, lotions, creams, gels, drops, suppositories, sprays, liquids and powders. Conventional pharmaceutical carriers, aqueous, powder or oily bases, thickeners and the like may be necessary or desirable. Pharmaceutical compositions for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

DETAILED DESCRIPTION OF THE INVENTION

The voltage-gated calcium (CaV3.1-3.3) channels constitute the T-type subfamily, whose dysfunctions are associated with epilepsy, psychiatric disorders, and chronic pain. The unique properties of low voltage-activation, faster inactivation, and slower deactivation of these channels support their role in modulation of cellular excitability and low-threshold firing. Thus, selective T-type calcium channel antagonists are highly sought after.

Experiments conducted during the course of developing embodiments for the present invention explored Ugi-azide multicomponent reaction (MCR) products to identify a selective antagonist of the T-type calcium channel. Of the 46 compounds tested, an analog of benzimidazolonepiperidine—5bk (1-{1-R)-{1-[(1S)-1-phenylethyl]-1H-1,2,3,4-tetrazol-5-yl}(thiophen-3-yl)methyl]piperidin-4-yl}-2,3-dihydro-TH-1,3-benzodiazol-2-one), inhibited depolarization-induced calcium influx in rat sensory neurons. Blockage of T-type calcium channels by 5bk was further confirmed in wholecell patch clamp assays in dorsal root ganglion (DRG) neurons, where pharmacological isolation of T-type currents led to a concentration-dependent inhibition with a low micromolar $IC_{50}$. Genetic knockdown revealed CaV3.2 to be the isoform inhibited by 5bk. 5bk inhibited spontaneous excitatory post synaptic currents and depolarization-evoked release of calcitonin gene-related peptide (CGRP) from lumbar spinal cord slices. Notably, 5bk did not target human mu, delta, or kappa opioid receptors. 5bk reversed mechanical allodynia in rat models of HIV-associated peripheral sensory neuropathy and chemotherapy-induced peripheral neuropathy (CIPN) and spinal nerve ligation (SNL) induced neuropathy, without effects on locomotor activity or anxiety.

Thus, 5bk represents a novel compound in the fight to develop non-addictive pain therapeutics.

As such, the present invention addresses the need for effective therapies for pain related to pan-T-type activity (e.g., CaV3.1, 3.2 and 3.3 activity) or specifically CaV3.2 activity by providing potent and selective inhibitors of pan-T-type activity (e.g., CaV3.1, 3.2 and 3.3 activity) or specifically CaV3.2 activity.

In additional experiments, natural small molecules and Ugi-azide four-component reaction products were screened to target T-type calcium channels for pain relief In a previous study, an analog of benzimidazolonepiperidine, 5bk (1-{1-[(R)-{1-[(1S)-1-phenylethyl]-1H-1,2,3,4-tetrazol-5-yl}(thiophen-3-yl)methyl]piperidin-4-yl}-2,3-dihydro-1H-1,3-benzodiazol-2-one), was found to decrease $Ca^{2+}$ influx and reverse mechanical allodynia in rodent models of HIV-associated neuropathy, chemotherapy-induced peripheral neuropathy, and spinal nerve ligation-induced neuropathy (Cai, S., Tuohy, P., Ma, C., Kitamura, N., Gomez, K., Zhou, Y., Ran, D., Bellampalli, S. S., Yu, J., Luo, S., Dorame, A., Yen Ngan Pham, N., Molnar, G., Streicher, J. M., Patek, M., Perez-Miller, S., Moutal, A., Wang, J., and Khanna, R. (2020) A modulator of the low-voltage-activated T-type calcium channel that reverses HIV glycoprotein 120-, paclitaxel-, and spinal nerve ligation-induced peripheral neuropathies, Pain 161, 2551-2570) (herein referred to as "Cai et al."). Such experiments further determined that the compound 3-14-3-S (S)-(4-((1-benzyl-1H-tetrazol-5-yl)(5-methylthiophen-2-yl)methyl)piperazin-1-yl)(furan-2-yl)methanone was found to have the potential to inhibit KCl- Induced $Ca^{2+}$ influx in dorsal root ganglia neurons. Furthermore, 3-14-3-S diminished $Ca^{2+}$ current density in rat sensory neurons and blocked transiently expressed CaV3.1, CaV3.2 and CaV3.3 channels with a similar $IC_{50}$. Consistent with inhibition of voltage-gated calcium channels, intrathecal delivery of 3-14-3-S mediated relief of tonic, neuropathic and inflammatory pain. Lastly, both 3-14-3 enantiomers were shown through in silico docking to bind to the CaV3.1 structure. These results suggest that multi-targeting T-type $Ca^{2+}$ channel isoforms may yield a more efficacious strategy for non-opioid pain management.

Accordingly, the present invention is in the field of medicinal chemistry. In particular, the invention relates to a new class of small-molecules having a piperazine or piperidine structure which function as either inhibitors of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx) or specific inhibitors of CaV3.2 voltage gated calcium channel activity, and their use as therapeutics for the treatment and/or prevention of pan-T-type calcium channel related pain (e.g., CaV3.1 related pain) (e.g., CaV3.2 related pain) (e.g., CaV3.3 related pain) (e.g., HIV-associated peripheral sensory neuropathy, chemotherapy-induced peripheral neuropathy (CIPN), spinal nerve ligation (SNL) induced neuropathy) (e.g., tonic, neuropathic, and/or inflammatory pain) and related conditions.

Certain piperazine or piperidine (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

including pharmaceutically acceptable salts, solvates, and/or prodrugs thereof.

Formula I is not limited to a particular chemical moiety for X, R1, R2, and R3. In some embodiments, the particular chemical moiety for X, R1, R2, and R3 independently include any chemical moiety that permits the resulting compound to inhibit pan-T-type voltage gated calcium channel activity (e.g., CaV3.1 voltage gated calcium channel activity) (e.g., CaV3.2 voltage gated calcium channel activity) (e.g., CaV3.3 voltage gated calcium channel activity). In some embodiments, the particular chemical moiety for X, R1, R2, and R3 independently include any chemical moiety that permits the resulting compound to specifically inhibit CaV3.2 voltage gated calcium channel activity. In some embodiments, the particular chemical moiety for X, R1, R2, and R3 independently include any chemical moiety that permits the resulting compound to inhibit depolarization-induced calcium influx related to pan-T-type voltage gated calcium channel activity. In some embodiments, the particular chemical moiety for X, R1, R2, and R3 independently include any chemical moiety that permits the resulting compound to inhibit depolarization-induced calcium influx related to CaV3.2 voltage gated calcium channel activity. In some embodiments, the particular chemical moiety for X, R1, R2, and R3 independently include any chemical moiety that permits the resulting compound to inhibit, prevent and/or ameliorate neuropathy pain related to pan-T-type activity. In some embodiments, the particular chemical moiety for X, R1, R2, and R3 independently include any chemical moiety that permits the resulting compound to inhibit, prevent and/or ameliorate neuropathy pain related to CaV3.2 activity. In some embodiments, the particular chemical moiety for X, R1, R2, and R3 independently include any chemical moiety that permits the resulting compound to inhibit, prevent and/or ameliorate pain related to pan-T-type activity. In some embodiments, the particular chemical moiety for X, R1, R2, and R3 independently include any chemical moiety that permits the resulting compound to inhibit, prevent and/or ameliorate pain related to CaV3.2 activity. In some embodiments, the particular chemical moiety for X, R1, R2, and R3 independently include any chemical moiety that permits the resulting compound to inhibit, prevent and/or ameliorate pain related to HIV-associated peripheral sensory neuropathy. In some embodiments, the particular chemical moiety for X, R1, R2, and R3 independently include any chemical moiety that permits the resulting compound to inhibit, prevent and/or ameliorate pain related to chemotherapy-induced peripheral neuropathy (CIPN). In some embodiments, the particular chemical moiety for X, R1, R2, and R3 independently include any chemical moiety that permits the resulting compound to inhibit, prevent and/or ameliorate tonic, neuropathic, and/or inflammatory pain. In some embodiments, the particular chemical moiety for X, R1, R2, and R3 independently include any chemical moiety that permits the resulting compound to inhibit, prevent and/or ameliorate pain related to spinal nerve ligation (SNL) induced neuropathy. In some embodiments, the particular chemical moiety for X, R1, R2, and R3 independently include any chemical moiety that permits the resulting compound to inhibit spontaneous excitatory post-synaptic currents via actions presynaptically. In some embodiments, the particular chemical moiety for X, R1, R2, and R3 independently include any chemical moiety that permits the resulting compound to inhibit release of the pronociceptive neurotransmitter calcitonin gene related peptide (CGRP).

In some embodiments, X is C thereby rendering the compound a piperidine based compound.

In some embodiments, X is N thereby rendering the compound a piperazine based compound.

In some embodiments, R1 is selected from

In some embodiments, R1 is hydrogen.

In some embodiments, R2 is selected from

-continued

-continued

In some embodiments, R3 is hydrogen.

In some embodiments, the compound is recited in FIG. 1B and FIG. 21A.

In some embodiments, the compound recited in FIG. 1B is a specific inhibitor of CaV3.2 voltage gated calcium channel activity.

In some embodiments, the compound recited in FIG. 21A is an inhibitor of pan-T-type calcium channel activity (e.g., CaV3.1 voltage gated calcium channel activity) (e.g., CaV3.2 voltage gated calcium channel activity) (e.g., CaV3.3 voltage gated calcium channel activity) (e.g., depolarization-induced calcium influx).

In some aspects, the present invention features a calcium channel modulator that is a derivative of 5bk below:

In some embodiments, R2 is hydrogen.

In some embodiments, R3 is selected from

According to some embodiments, the modulator is according to any one of the following compounds:

53

54

1-159-2

1-159-2-S 1-159-2-R 3-14-3

3-14-3-R 3-14-3-S 3-25

In some embodiments, the modulator can be the S- or R-enantiomer of said compounds, as shown below:

-continued 3-25-S 3-25-R

In some preferred embodiments, the modulator is 3-14-3-S:

3-14-3-S

Without wishing to limit the invention to a particular theory or mechanism, 3-14-3-S may be effective for inhibiting depolarization-induced $Ca^{2+}$ influx through T-type $Ca^{2+}$ channels. Also, 3-14-3-S may be effective for decreasing $Ca^{2+}$ current density and T-type $Ca^{2+}$ currents. In some embodiments, 3-14-3-S is effective for treating and preventing pain.

The invention further provides processes for preparing any of the compounds of the present invention.

The pan-T-type inhibitors and specific CaV3.2 inhibitors described herein can be considered as potential therapeutics for the treatment, prevention, and/or amelioration of conditions characterized with pain related pan-T-type activity or specific CaV3.2 activity (e.g., pain related to general neuropathy; pain related to diabetes related neuropathy; pain related to HIV-associated peripheral sensory neuropathy; inhibiting, preventing and/or ameliorating pain related to chemotherapy-induced peripheral neuropathy (CIPN); inhibiting, preventing and/or ameliorating pain related to spinal nerve ligation (SNL) induced neuropathy; inhibiting, preventing and/or ameliorating tonic, neuropathic, and/or inflammatory pain).

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, conditions related to aberrant pan-T-activity or specifically CaV3.2 activity, pain related to pan-T- voltage gated calcium channel activity or specifically CaV3.2 voltage gated calcium channel activity, pain related to HIV-associated peripheral sensory neuropathy, pain related to chemotherapy-induced peripheral neuropathy (CIPN); pain related to spinal nerve ligation (SNL) induced neuropathy, neuropathy related to pan-T-activity or specifically CaV3.2 activity, and diabetic neuropathy related to pan-T-activity or specifically CaV3.2 activity.

Some embodiments of the present invention provide methods for administering an effective amount of a compound of the invention and at least one additional therapeutic agent (including, but not limited to, any agent useful in treating pain related to pan-T-activity or specifically CaV3.2 activity).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl- cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

According to some embodiments, the present invention features a composition for use in blocking a calcium channel. The calcium channel may be a T-type calcium channel. In preferred embodiments, the composition may comprise one or more of the calcium channel modulators described herein. In some embodiments, the modulator can block CaV3.1, CaV3.2 and/or CaV3.3 channels.

According to other embodiments, the present invention features a method of blocking a calcium channel. The calcium channel may be a T-type calcium channel. In some embodiments, the method may comprise exposing the calcium channel to a calcium channel modulator. In some embodiments, the modulator can block CaV3.1, CaV3.2 and/or CaV3.3 channels. Non-limiting examples of the modulator include the calcium channel modulators described herein.

According to some embodiments, the present invention features a composition for use in treating or preventing pain, such as tonic, neuropathic, and/or inflammatory pain. In preferred embodiments, the composition may comprise one or more of the calcium channel modulators described herein, in a pharmaceutically acceptable carrier.

According to other embodiments, the present invention features a method of treating or preventing pain in a subject in need of such treatment. The method may comprise administering to the subject a therapeutically effective amount of one or more of the calcium channel modulators described herein. In some embodiments, the subject is a mammal, such as a human.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Examples

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention. As used herein, personal pronouns such as "our", "we", "I", etc. refer to the inventors of the present invention.

The following abbreviations are relevant for the following examples: A549, adenocarcinomic human alveolar basal epithelial cells, AITC, Allyl isothiocyanate; CaV3, voltage-gated calcium channel subfamily 3; CC50, cytotoxic concentration; CGRP, calcitonin gene-related peptide; CHO, Chinese Hamster Ovary; CIPN, chemotherapy-induced peripheral neuropathy; DOR, delta opioid receptor DRG, dorsal root ganglia; EPM, elevated plus maze; hERG, human Ether-a-go-go-Related gene, codes for Kv11.1 channel; HIV gp120, human immunodeficiency virus envelope glycoprotein; KOR, kappa opioid receptor; KCl, potassium chloride; LVA, low voltage-activated; MOR, mu opioid receptor; MCR, multicomponent reactions; MDCK, Madin-Darby Canine Kidney cells; sEPSCs, spontaneous excitatory post-synaptic currents; HVA, high-voltage-activated; IB4, isolectin B4; CCI, chronic constriction injury; SNI, spared nerve injury, PSNL, partial sciatic nerve ligation; 5bk, 1-{1-[(R)-{1-[(1S)-1-phenylethyl]-1,2,3,4-tetrazol-5-yl} (thiophen-3-yl)methyl]piperidin-4-yl}-3H-1,3-benzodiazol-2-one; Z944, {N}-[[1-[2-(-{tert}-butylamino)-2-oxida-nylidene-ethyl]piperidin-4-yl]methyl]-3-chloranyl-5-fluoranyl-benzamide.

Example I

Chemical Synthesis

Figures 2A, 2B:
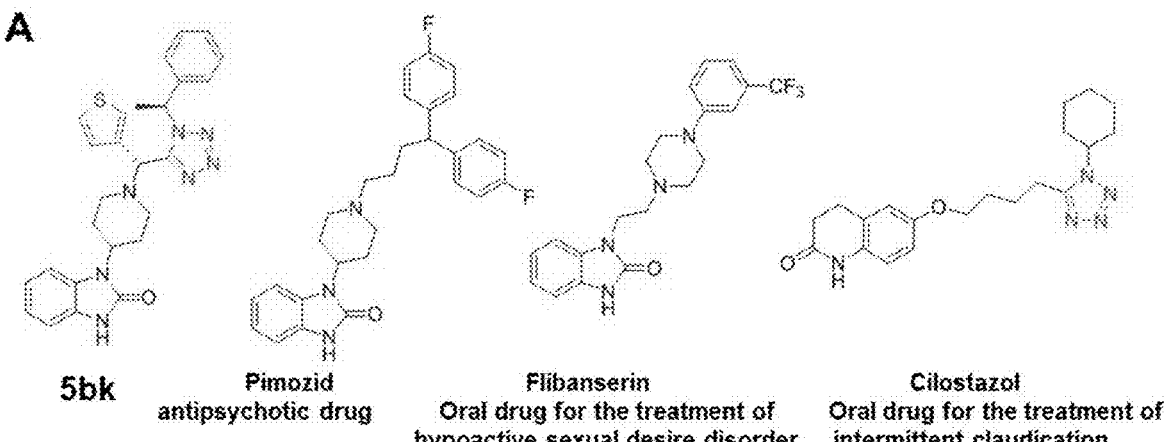
FIG. 2A-B: (A) List of FDA-approved oral drugs that share similar structural features with 5bk (B) Calculated ADME properties by Glide QikProp.

All compounds were synthesized using the Ugi-azide four-component reaction methodology as shown in FIG. 1A. Chemical structures for the compounds tested in the $Ca^{2+}$ flux assay are shown in FIG. 1B. Inspection of the chemical structure of 5bk (FIG. 3) did not reveal any significant metabolic and toxic liabilities, [72] as similar structural components from 5bk are also found in a number of FDA-approved oral drugs (FIG. 2).

5bk was not cytotoxic to either Madin-Darby Canine Kidney (MDCK) cells or adenocarcinomic human alveolar basal epithelial (A549) cells (cytotoxic concentration, CC50>100 μM).

Identification of Antagonists of Low Voltage Activated (LVA) T-Type Calcium Channels.

Using Fura 2-AM based ratiometric calcium-imaging assay as we have established before [23; 53; 54; 88], we screened an in-house diversity library of compounds (at 20 μM) for their inhibition of Ca2+ influx via low (triggered with 40 mM KCl) and high (triggered with 90 mM KCl) voltage activated calcium channels in primary rat dorsal root ganglion (DRG) neurons. The goal was to identify hits that inhibit LVA calcium channels but not high-voltage activated calcium channels. In the first set, one compound, 5aa, inhibited ~45% of the $Ca^{2+}$ influx when DRGs were depo-larized with 40 mM KCl and ~60% when depolarized with 90 mM KCl (FIG. 3A, B). As no compound in the initial round was selective for low voltage-activated calcium chan-nels, we selected 5aa for further optimization with the primary goal of achieving preferential activity towards LVA channels.

Encouraged by discovery of this initial hit, we subse-quently synthesized a focused library of 45 analogs of 5aa by varying the amine, aldehyde, and isocyanide components using the established Ugi-azide four-component reaction condition. The structures of the compounds are shown in FIG. 1B. Compounds 5ab, 5ak, 5al, 5ao, 5aq, 5at, 5aw, 5ax, 5ay, 5ba, 5be, 5bh, 5bi, 5 bp, 5bq, 5br, 5bs, and 5bt were synthesized and tested as a diastereomer mixtures.

Compounds 5bk and 5bl were tested as pure diastereom-ers and their absolute stereochemistry were confirmed by X-ray crystallography [93]. Three of the 46 compounds, 5ay 5bk, and 5bt inhibited >75% of $Ca^{2+}$ influx when DRGs were depolarized with 40 mM KCl, of which 2 of these compounds 5ay and 5bt showed >50% inhibition when also triggered with 90 mM KCl (FIG. 3A, B). One compound, 5bk (FIG. 3C) appeared selective in inhibiting KCl-evoked $Ca^{2+}$ influx with 88.5±2.6% inhibition (n=78) relative to the negative control (0.01% DMSO) when stimulated with 40 mM KCl and an ~33.9±4.0% inhibition (n=78) of evoked $Ca^{2+}$ influx when stimulated with 90 mM KCl. The inhibi-tion was observed only after at least 30 minutes of applica-tion of 5bk and achieved a maximum with overnight treat-ment (FIG. 3D). The corresponding diastereomer, 5bl, did not show significant inhibition of $Ca^{2+}$ flux with <25% signal reduction when DRGs were depolarized with either 40 mM or 90 mM KCl. Notably, compounds 5bk and 5bl were previously tested for their inhibition of the influenza virus polymerase PA-PB1 protein-protein interactions, and only compound 5bl was found to be active [93]. These results suggest compound 5bk interacts with T-type $Ca^{2+}$ channels in a stereospecific manner. Overall, compound 5bk is the most potent and selective antagonist against the T-type $Ca^{2+}$ channel among all the compounds tested.

We further analyzed the features of 5bk antagonism, finding a concentration-dependent inhibition of LVA cur-rents with an $IC_{50}$ of 4.2±0.6 μM (FIG. 3E). The inhibition was time-dependent with increasing block observed with longer incubation periods (FIG. 3D). 5bk also did not inhibit hERG channel at 10 μM in two-electrode voltage clamp assay, which has important implications for therapeutic safety (SUPP*3).

5bk Inhibits T-Type $Ca^{2+}$ Channels in Sensory Neurons

One of the most potent hit compounds from the primary calcium imaging screening was 5bk (FIG. 3), which showed nearly ~90% inhibition of $Ca^{2+}$ channel influx at 20 μM when DRGs were depolarized with 40 mM KCl. As the inhibition of calcium influx elicited by 5bk appeared to be more pronounced with 40 mM KCl versus 90 mM KCl (FIG. 3), we chose to test if T-type calcium channels were being preferentially targeted by this compound. In DRG sensory neurons, the a subunits of Cav3.2 and Cav3.3 represent the majority of T-type $Ca^{2+}$ channels [92]. Therefore, we used electrophysiology protocols described before [14] to record T-type currents. From a holding potential of −90 mV, we used 200-ms depolarization steps to change the membrane potential from −70 to +60 mV (10 mV increments) to evoke prototypical T-type calcium currents (FIG. 5A). After treatment with 0.01% DMSO (vehicle, n=16) or 5bk (2 μM, n=16), we recorded low voltage-activated calcium currents (FIG. 5A) from DRG neurons with an average diameter between 20-30 μm. We measured current voltage (I-V) relationships (FIG. 5B) and observed that treatment with 5bk reduced T-type calcium current amplitudes between −20 mV and +10 mV test potentials (FIG. 5B). At peak current density (~10 mV), there was ~42.2% reduction in current in 5bk-treated cells compared with vehicle-treated controls (FIG. 5C). Treatment with 5bk did not alter the channel gating properties as we measured a similar half-maximal activation (V0.5) of T-type calcium channels in both conditions (FIG. 5D). The kinetics of macroscopic current inactivation (FIG. 5E) were unchanged at all membrane potentials tested (~40 mV, FIG. 5F). The time-dependent activation (10 to 90% rise time) of T-type currents was not affected by treatment with 5bk (FIG. 5G-H). We next tested whether 5bk could control the voltage-dependent kinetics of channel inactivation (FIG. 5I) and found this property to also not be affected by treatment with 5bk. Deactivating tail currents calculated using the single exponential function: $y=A1 \times e(-x/\tau 1)+y0$, where A1 is the amplitude, $\tau 1$ is the decay constant, and y0 is the offset. The resulting $\tau$ values (FIG. 5J), showed no differences irrespective of the treatment condition. Finally, because upon long membrane hyperpolarizations in DRG neurons T-type calcium channels can recover from inactivation, we tested if this biophysical parameter could be affected by treatment with 5bk. This property has important consequences on the firing properties of sensory neurons expressing T-type calcium channels. Thus, we tested the recovery from inactivation using a double pulse protocol with a variable interpulse duration at −90 mV (FIG. 5K) after a 500-ms-long inactivating pulse (Vh=−90 mV; Vt=−30 mV). T-type currents recovered fully, independently of the treatment condition (FIG. 5K). Taken together, our results show that 5bk specifically blocks T-type calcium channels in DRG neurons.

Given the lack of effect of 5bk on the kinetic and voltage-dependent properties of T-type calcium currents, it is possible that 5bk downregulates functional T-type channels by acting on second messenger pathways. To test this possibility, we applied 5bk acutely during recordings. The results (FIG. 4), showed no inhibition of T-type currents, consistent with our data obtained from calcium imaging (FIG. 3D). Consequently, biophysical properties (i.e. voltage-activation, inactivation, recovery from inactivation) of these LVA channels were also unaffected by 5bk (FIG. 4).

To further explore selectivity of 5bk for Cav3 over other HVA channel types, we examined how other channels were affected by 5bk (FIG. 6). 5bk, applied overnight, had no effect on pharmacologically isolated L-type (CaV1.x) (FIG. 6C, D), P/Q-type (CaV2.1) (FIG. 6H, I), N-type (CaV2.2) (FIG. 6M, N), or R-type (CaV2.3) (FIG. 6R, S) nor did it affect the $V_{1/2}$ of activation or inactivation (FIG. 6E, J, O, T and FIG. 7). Finally, we also observed no effects of 5bk on tetrodotoxin-sensitive or -resistant voltage-gated sodium currents (FIG. 8).

5bk Inhibits CaV3.2 T-Type $Ca^{2+}$ Channels

To test if 5bk preferentially targets a specific T-type $Ca^{2+}$ channel subunit we used a knockdown strategy (using short interfering RNA (siRNA)) to eliminate either CaV3.1, CaV3.2 or CaV3.3 in DRG sensory neurons (FIG. 9). DRG neurons were electroporated with the indicated siRNA (or a scrambled negative control) in combination with a GFP expressing plasmid (to identify transfected cells). The cells were cultured for 24 hours before adding 20 μM of 5bk overnight (or 0.1% DMSO as control) and then tested using 40 mM KCl as a trigger (FIG. 9). In scramble siRNA-transfected cells, 5bk inhibited 40 mM KCl evoked Ca2+ influx by ~53% (FIG. 9). In neurons with a knock down of CaV3.2, 5bk failed to inhibit the 40 mM KCl evoked $Ca^{2+}$ influx. In contrast, after the knockdown of either CaV3.1 or CaV3.3, significant inhibition of calcium influx was still noted upon depolarization with 40 mM KCl (FIG. 9). Thus, we conclude that 5bk may preferentially inhibits CaV3.2 $Ca^{2+}$ channel subunits. A limitation of this approach is that the low expression of CaV3.1 or CaV3.3 in native DRG neurons may mask a potential inhibitory action of 5bk.

5bk's Effects on Subpopulations of DRG Neurons

The data presented thus far demonstrates the potential for 5bk to inhibit $Ca^{2+}$ influx via T-type Ca2+ channel. However, which cell-specific neuronal classes are implicated in 5bk's mechanism of action has not yet been addressed. In order to investigate this, we used the previously described constellation pharmacology protocol[75; 76] to explore cell-specific functionality as a result of key signaling proteins that define precise cell types. The constellation pharmacology assay poses 6 consecutive challenges, each 6 minutes apart, to compare $Ca^{2+}$ influx due to activity of $Ca^{2+}$-associated membrane proteins: Ca2+ permeable ligand-gated ion channels, metabotropic receptors and voltage-gated $Ca^{2+}$ channels. Following these 6 stimulations, KCl-evoked response due to membrane depolarization is used to assess viability of neurons; neurons not responsive to KCl are excluded from analysis.

Figure 10:
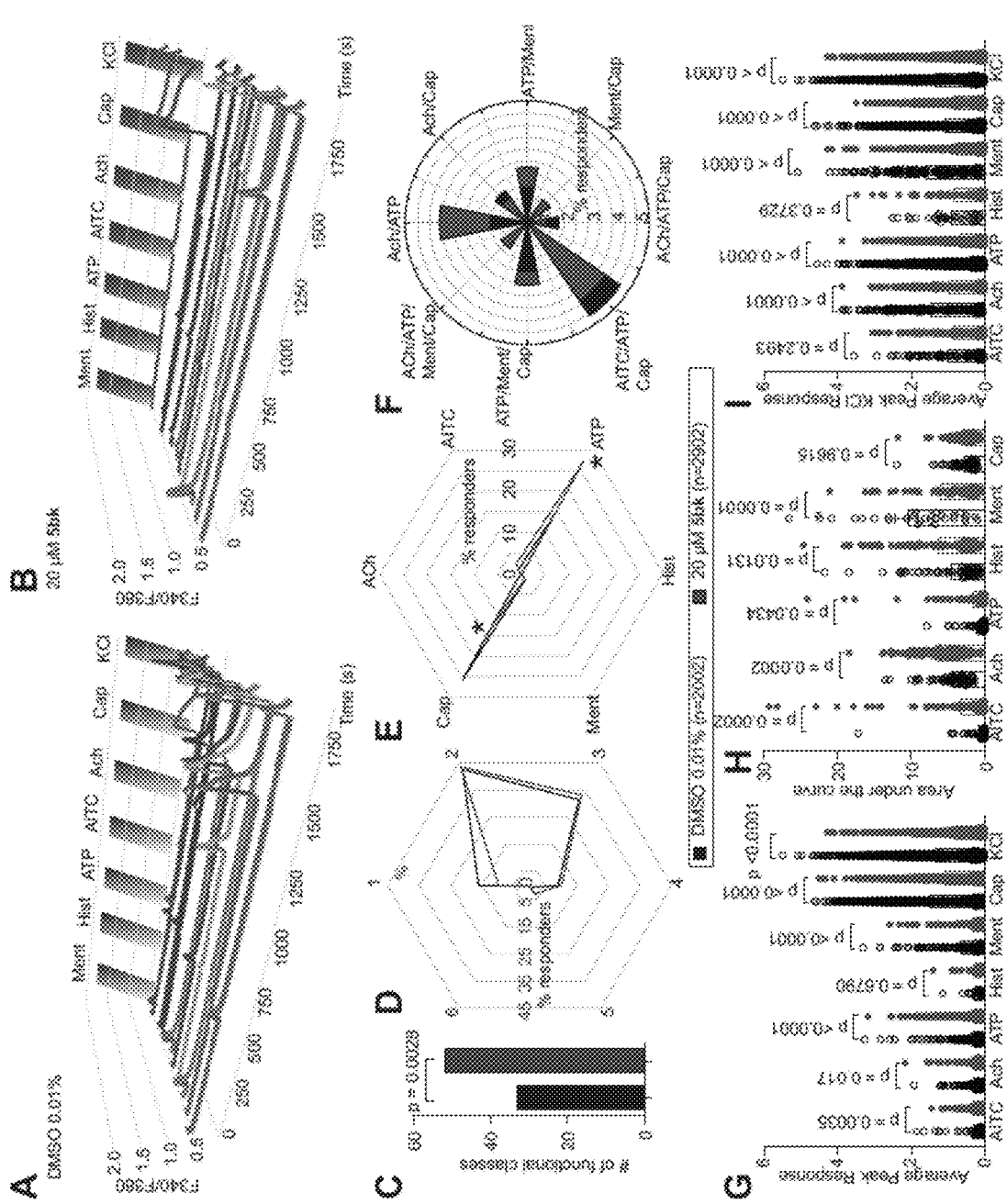

The versatility in neuronal responsivity is demonstrated by exemplary traces of rat DRG sensory neurons treated with control (0.1% DMSO) or a 20 μM concentration of 5bk as specified (FIGS. 10A, B). Representative images of DMSO and 5bk-treated neurons (FIG. 11, FIG. 12), show examples of calcium responses before and after challenge with each of the constellation triggers: menthol (400 nM), histamine (50 μM), ATP (10 μM), AITC (200 μM), acetylcholine (1 mM), capsaicin (100 nM) and KCl (90 mM)) during the constellation pharmacology protocol. Inhibition of $Ca^{2+}$ influx due to KCl stimulus was again inhibited as a result of treatment with 5bk; this is consistent with our previous data (FIG. 3). Sensory neurons were incubated overnight with the specified treatment, 0.01% DMSO (n=2002) or 5bk (n=2902) and imaged the following day with the constellation pharmacology protocol. Data was collected from 5 independent experiments, and individual neuronal responses to each constellation trigger were analyzed. Neurons with responses under 10% of baseline fluorescence were excluded from the analyses.

We began with exploring the effect of 5bk on the overall functionality of sensory neurons. This was analyzed in terms of functional cell subclasses present in the population of neurons treated with 5bk in comparison to the control population. Notably, more functional subclasses were present in the population of neurons treated with 5bk in comparison to those treated with vehicle control (FIG. 10C). However, response of neurons to the number of stimulatory challenges, independent of which specific agonists triggered response, was not altered by 5bk treatment (FIG. 10D). Furthermore, we inquired whether 5bk affected the sensitivity of DRGs to the different constellation triggers, by analyzing the percent of cells responding to a specific constellation trigger, independently of any other constellation triggers these neurons may have responded to: we noted an increased sensitivity to ATP stimulation and decreased sensitivity to capsaicin following treatment with 5bk (FIG. 10E). Similarly, following treatment with 5bk, there were more responders in functional cell subclasses including ATP as an agonist, and less responders in those including capsaicin as an agonist (FIG. 10F).

In a more targeted inquiry, we also investigated the effect of 5bk on the extent of $Ca^{2+}$ influx following specific stimulation by each constellation trigger. Thus, we analyzed peak $Ca^{2+}$ responses (FIG. 10G) and area under the curve (AUC) of these responses (FIG. 10H) in sensory neurons as a result of the specified treatment. Interestingly, while 5bk significantly altered peak $Ca^{2+}$ responses to menthol, and capsaicin stimulation, only stimulation with capsaicin altered the AUC of $Ca^{2+}$ response: the AUC was decreased.

We then asked if KCl-evoked $Ca^{2+}$ response as a result of 5bk would be altered in a functional class specific manner (FIG. 10I). To test this, we assessed average peak $Ca^{2+}$ response due to KCl challenge in sensory neurons that specifically responded to a particular constellation trigger, independent of any other constellation triggers that they might have responded to. Treatment with 5bk significantly decreased KCl-evoked $Ca^{2+}$ response in sensory neurons that responded to an ATP and menthol stimulus; however, DRGs that responded to ACh, AITC, Histamine, and capsaicin did not have significantly altered KCl-evoked response due to 5bk treatment (FIG. 10I).

These results reveal the full actionable mechanisms of $Ca^{2+}$ inhibition by 5bk and suggest its potential efficacy as an anti-nociceptive agent.

5bk does not Bind to the Orthosteric Site of the Opioid Receptors

To assess if 5bk could work by off-target binding to the opioid receptors, we performed competition radioligand binding at all 3 opioid receptors in vitro. We competed 5bk and a positive control compound (naloxone for MOR and DOR, U50,488 for KOR) vs. a fixed concentration of $^{3}$H-diprenorphine in Chinese Hamster Ovary (CHO) cells expressing the human μ (MOR), δ (DOR), or κ (KOR) opioid receptor. We found that 5bk did not bind to any opioid receptor up to a 10 Mm concentration (FIG. 13A-C). In contrast, the positive control compounds bound to all 3 targets with expected affinity (FIG. 13A-C). These results strongly suggest that 5bk is not engaging the opioid receptors, and that potential anti-nociception would thus not be as a result of opioid receptor association.

5bk Inhibits Spontaneous Excitatory Post-Synaptic Currents Via Presynaptic Actions Since T-type calcium channels contribute to action potential firing and neurotransmitter release [10], we performed electrophysiological recordings in substantia gelatinosa neurons in the superficial layers (within laminae I-II) of the spinal dorsal horn to measure whether 5bk could inhibit spontaneous excitatory post-synaptic currents (sEPSCs). There was no significant decrease in spontaneous EPSC amplitude (post-synaptic effect) (FIG. 14A, B) of neurons treated with 0.10% DMSO or 5bk (20 μM). However, 5bk treatment decreased sEPSC frequency (DMSO, 1.96±0.21 Hz; 5bk, 1.26±0.17 Hz, P<0.05) (FIG. 14C), suggesting a presynaptic suppression of neurotransmitter release by 5bk.

5bk Inhibits Calcitonin Gene Related Peptide (CGRP) Release in Spinal Cord Slices Calcium entry via T-type $Ca^{2+}$ channels contributes to the release of neurotransmitters, including CGRP, in the spinal dorsal horn.[63; 71; 79] Emergent evidence overall suggests that CGRP facilitates nociceptive transmission and contributes to development and maintenance of a sensitized, hyper-responsive state not only of the primary afferent sensory neurons but also of second-order pain transmission neurons within the CNS. This CGRP activity is thus thought to contribute to central sensitization as well. CGRP concentrations in spinal cords was measured directly via ELISA kits as described by us previously.[7] We observed that 5bk inhibits KCl-evoked CGRP release from spinal cords, suggesting 5bk could be anti-nociceptive in vivo (FIG. 15).

Appraisal of 5bk in Three Models of Neuropathy in Rat

We used the spinal nerve ligation (SNL) model of neuropathic pain to evaluate the potential of 5bk to reverse nociception. SNL injury efficiently reduced paw withdrawal thresholds (PWTs) (mechanical allodynia, FIG. 16A) 7 days post injury. Spinal administration of 5bk significantly increased PWTs (FIG. 16A) for 2 hours during the course of the experiment. Transformation of the behavior data into percent anti-allodynia demonstrated a significant reversal of allodynia in rats injected with 5bk (FIG. 16B). AUC analysis confirmed the reversal of mechanical allodynia (FIG. 16C) compared to vehicle-treated injured animals.

Of the many complications associated with both HIV and chemotherapy, a common symptom is HIV induced sensory neuropathy and chemotherapy-induced peripheral neuropathy (CIPN) respectively [48]. Since voltage-gated $Ca^{2+}$ channels have previously been found to contribute to neuropathic pain [57], we explored the potential utility of 5bk in reversing the nociceptive effects induced by injections of the HIV envelope glycoprotein (gp120) or the chemotherapeutic drug paclitaxel. To test this, we first induced mechanical allodynia via 3 intrathecal injections of gp120, which has been shown to induce mechanical allodynia in animals[51; 91]; a subsequent reversal of mechanical allodynia by intrathecal injection of 5bk (2 μg/5 μL) was seen at approximately 60 minutes post-gp120 injection and lasted for 4 hours (FIG. 16D). The same was true for the transformed data plotted as % anti-allodynia which was significantly reversed in rats injected with 5bk (FIG. 16E). This reversal of mechanical allodynia was also substantiated with a corresponding increase in area under the curve (FIG. 16F) associated with intrathecal administration of 5bk.

Next, we assessed the effectiveness of intrathecally injected 5bk (2 μg/5 μL) in ameliorating mechanical allodynia induced by a total of 4 paclitaxel injections (2 mg/kg, intraperitoneal). Again, 5bk resulted in a reversal of mechanical allodynia at two hours post-injection and lasting for at least two hours with a commensurate increase in area under the curve in comparison to saline-injected animals (FIG. 16G-I). Together, these results demonstrate that 5bk is Antinociceptive in Rodent Models of Neuropathic Pain.

5bk does not alter motor function or anxiety levels in treated animals Since 5bk appears to be a promising anti-nociceptive agent in terms of neuropathic pain models, we next asked if the compound had any effects on motor function or anxiety in naïve animals. To test for motor deficits, we subjected rats to a rotarod performance test. Compared to vehicle-treated rats, there was no significant change in motor function in animals treated with intrathecal 5bk. Vehicle-treated animals remained on the rotarod for an average of $172\pm7.3$ seconds (cutoff time 180 seconds per test) over a time course of 300 minutes; 5bk-treated animals remained on the rotarod for an average of $170\pm9.6$ seconds over a time-course of 300 minutes (FIG. 17A). From these results, we conclude that 5bk does not induce motor deficits.

To test if anxiety levels are affected by 5bk, we subjected naive rats to the elevated plus maze (EPM) test. The measured anxiety index integrates both measurement of times and entries of the animals into the open and closed arms of the EPM. Index values closer to 1 indicate higher anxiety levels. Results indicate that there was no significant change in anxiety index between animals treated with 5bk (2 µg/5 µL, i.t.) and those treated with the vehicle (FIG. 17B), and thus we conclude that 5bk is an antinociceptive agent that does not cause dysfunction in motor or anxiety-related measures.

DISCUSSION

The present work used Ugi-azide MCR products to identify a selective antagonist of the T-type $Ca^{2+}$ channel CaV3.2. Of the 46 compounds tested, 5bk—a benzimidazolonepiperidine analog, interacted with the T-type $Ca^{2+}$ channels in a stereospecific manner, specifically blocked T-type calcium channels in a concentration and time-dependent manner and preferentially inhibited the CaV3.2 isoform. 5bk inhibited spinal neurotransmission which resulted in a decrease in CGRP release from the spinal cord. Finally, 5bk had an anti-nociceptive effect in rodent models of neuropathic pain (FIG. 16) without inducing adverse side effects (FIG. 17). Taken together our findings indicate that the preferential inhibition of CaV3.2 channels results in a selective and safe antinociceptive effect.

During the biochemical characterization of 5bk, we came across a paper by Zhao et al. reporting the cryo-EM structure of the human apo CaV3.1 channel bound to the selective blocker Z944 [94]. We generated homology models of both CaV3.2 and CaV3.3 using the Phyre2 server. Structurally, the models are identical to CaV3.1 and we used the homology model structure of CaV3.2 to dock 5bk (FIG. 18). Closer inspection of 5bk and Z944 ({N}-[[1-[2-(-{tert}-butylamino)-2-oxidanylidene-ethyl]piperidin-4-yl]methyl]-3-chloranyl-5-fluoranylbenzamide) T-type $Ca^{2+}$ channel blockers revealed similar pharmacophore features (FIG. 18, FIG. 19) presumably responsible for productive binding of both antagonists. Due to the extremely high sequence similarity in CaV3.1-3.3 in and around the binding cavity, we cannot conclude as to the exact residues that may confer selectivity of this compound. Notably, decoration of the common piperidine core would suggest a similar molecular shape within the channel cavity with functional groups pointing to the same areas (FIG. 19). Indeed, the 3-D overlay confirms the topological match of aligned scaffolds with carbonyl groups at the southern part of each molecule presented as a shared pharmacophore feature (FIG. 18B, FIG. 19).

Similarly, the top carboxamide in Z944 overlaps with nitrogens in the tetrazole ring of 5bk, mimicking the amide bond of the former molecule. Phenyl and t-butyl groups from the corresponding molecules point in the same direction. However, the 3-thiophenyl group is not present in Z944, suggesting a hydrophobic pocket in that area that was explored during our lead compound optimization.

The presence of two chiral centers on 5bk gives rise to four possible enantiomers as two pairs of diastereomers. To simplify the structure elucidation of the bioactive stereoisomer, we utilized enantiomerically pure (1S)-methylbenzyl isocyanide as a reagent and separated resulting diastereomers by silica gel flash column chromatography. From the X-ray crystal structure, we found out that the relative configuration of the bioactive diastereomer is (1R, 2S) where the first descriptor refers to the chiral carbon bearing the 3-thiophenyl substituent. SAR obtained from analogs within the library of Ugi-azide MCR products suggests the possibility of replacing 4-aminopiperidine with a druglike N-acyl- or N-arylpiperazine scaffold. Moreover, SAR expansion in the thiophenyl area is expected to improve both potency and selectivity.

T-type $Ca^{2+}$ channels were generally considered to regulate neuronal excitability at peripheral terminals of nociceptors, while high-voltage-activated (HVA) N- and P/Q- type $Ca^{2+}$ channels regulate neurotransmitter release such as glutamate and substance P in the spinal cord [61]. The majority of studies examining T-type $Ca^{2+}$ channels in the spinal cord have used less specific blockers such as ethosuximide [49], mibefradil [47] TTA-A2 and TTA-P2 [35] to determine the function of the channels. However, there is evidence indicating that CaV3.2 channels regulate low threshold exocytosis in cell cultures [85] and spontaneous release of glutamate in the spinal cord dorsal horn [35]. Unlike HVA $Ca^{2+}$ channels, where several members of the vesicle release machinery interact with a synprint (synaptic protein interaction site) [62; 66], T-type $Ca^{2+}$ channels lack the consensus synprint site, therefore, the neurotransmitter release machine interacts with the C-terminal domain of the CaV3.2 channels for neurotransmitter release [84]. In the present study we show that selective blockade of the CaV3.2 channels plays an important role in the excitatory synaptic transmission since 5bk inhibited the frequency but not the amplitude of sEPSCs (FIG. 14). A decrease in frequency suggests that 5bk inhibits glutamatergic excitatory inputs by a presynaptic mechanism. It is well accepted that alterations in the frequency of EPSCs with any agent targeting an ion channel indicates that this particular channel plays a presynaptic role, while changes in amplitude suggest a postsynaptic role of the channel. This is consistent with a previous report in which Jacus and colleagues demonstrated that CaV3.2 channels are the subtype of T-type $Ca^{2+}$ channels responsible for presynaptic modulation of spontaneous synaptic transmission in lamina I and II [35]. Moreover, CaV3.2 channels appear not to participate in inhibitory synaptic transmission [35].

DRG neurons have been shown to differentially express T-type $Ca^{2+}$ channels [64] with medium size neurons expressing the highest levels of CaV3.2 followed by the small size neurons [67]. T-type $Ca^{2+}$ currents are present in ~66 and ~42% of medium and small neurons, belonging to lightly myelinated A6 and unmyelinated C fibers, respectively [4]. Small C-type fiber nociceptors can be subdivided according to the expression of histological markers [68; 73]. One group are the peptidergic fibers that express proinflammatory peptides such as CGRP and substance P and project to the most superficial layers of the spinal cord dorsal horn, lamina I and the outer lamina II. A second group, the nonpeptidergic fibers, can be identified by the presence of binding sites for the isolectin B4 (IB4) and do not express substance P nor CGRP. These C fibers project to inner lamina II of the spinal cord dorsal horn [68]. Among these fibers, CaV3.2 expresses preferentially in the CGRP neurons and to a lesser extent in IB4 positive fibers [35]. Importantly, our findings show that that 5bk inhibited depolarization evoked CGRP release in spinal cord (FIG. 15), a known excitatory neurotransmitter that facilitates nociceptive transmission and contributes to central sensitization [68]. These results suggest a mechanism for the anti-nociceptive effect of 5bk (FIG. 16).

CaV3.2 channel expression and activity is increased in DRG neurons and in the spinal cord dorsal horn in neuropathic pain, such as in the L5 spinal nerve cut [74], L5/L6 SNL [29], chronic constriction injury (CCI)[36], diabetic neuropathy [37; 50], paclitaxel-induced peripheral neuropathy [44], spared nerve injury (SNI)[38], chronic compression of DRGs [86], and partial sciatic nerve ligation (PSNL) [20] rodent models. Although changes in the open probability of CaV3.2 cannot be ruled out, the most straightforward explanation for a change in current density, as we showed in our results (FIG. 5), is that 5bk decreases the cell surface or the protein expression of CaV3.2 channels. It is known that phosphorylation [5], glycosylation [83] and ubiquitylation [26] are two important post-translational regulation mechanisms that positively regulate surface expression of these channels.

It is also noteworthy that in neuropathic pain, there is a redistribution of the α2δ-1 HIVA Ca2+ channels auxiliary subunit [2] and CaV3.2 channels [29] to the DRG of injured nerves. DRGs have been shown to be an ectopic activity generation sites that play an important role in the development and maintenance of neuropathic pain [45]. Similar to TRPV1 [25] and NaV1.8 channels [28], CaV3.2 channels are redistributed to uninjured nerves in neuropathic pain models. This contributes to spontaneous activity and suggests an important role in pain hypersensitivity [12; 46]. In our present study, we have demonstrated that selective blockade of CaV3.2 channels with 5bk reversed neuropathic pain (FIG. 16), which is consistent with previous reports of CaV3.2 silencing in DRGs of rats with CCI [4] and paclitaxel-induced peripheral neuropathy [38]. Interestingly, similar to mice lacking CaV3.2 [15], intrathecal administration of 5bk had no alterations in motor function or anxiety (FIG. 17). However, a limitation here is that since 5bk was administered intrathecally, it is possible that not enough of the compound may have reached the brain to engage CaV3.2 channels therein.

Finally, recent evidence from experiments involving recombinant T-channels indicate that the βγ subunit of G protein coupled receptors selectively inhibits the function of CaV3.2 channels by interacting with the intracellular loop connecting domains II and III and by decreasing single channel open probability [16]. Our findings suggested that 5bk did not target G-protein coupled opioid receptor signaling (FIG. 13). Thus, inhibition of Ca2+ influx by 5bk likely does not involve opioid receptors. Moreover, contrary to our previously identified CaV3.2 inhibitor betulinic acid [3], 5bk did not affect any of the high voltage-activated calcium channels including N-type (CaV2.2) (FIG. 6), hERG channel activity (FIG. 20), or sodium channel activity FIG. 8), which helps to confirm drug selectivity. In conclusion, the findings recited herein describe the identification of a new class of inhibitors of CaV3.2 T-type Ca2+ channels, which are promising candidates for efficacious, non-opioid pain therapeutics.

Example II

This example describes the compound synthesis and characterization.

Chemistry

Chemicals were ordered from commercial sources and were used without further purification. Synthesis procedures for reactions described in Scheme 1 were shown below. All final compounds were purified by flash column chromatography. 1H and 13C NMR spectra were recorded on a Bruker-400 NMR spectrometer. Chemical shifts are reported in parts per million referenced with respect to residual solvent (CD3OD) 3.31 ppm, (DMSO-d6) 2.50 ppm, and (CDCl3) 7.24 ppm or from internal standard tetramethylsilane (TMS) 0.00 ppm. The following abbreviations were used in reporting spectra: s, singlet; d, doublet; t, triplet; q, quartet; m, multiplet; dd, doublet of doublets; ddd, doublet of doublet of doublets. All reactions were carried out under N2 atmosphere unless otherwise stated. HPLC-grade solvents were used for all reactions. Flash column chromatography was performed using silica gel (230-400 mesh, Merck).

Low-resolution mass spectra were obtained using an ESI technique on a 3200 Q Trap LC/MS/MS system (Applied Biosystems). The purity was assessed by using a Shimadzu LC-MS with a Waters XTerra MS C-18 column (part no. 186000538), 50 mm×2.1 mm, at a flow rate of 0.3 mL/min; λ=250 and 220 nm; mobile phase A, 0.1% formic acid in H2O, and mobile phase B', 0.1% formic in 60% 2-propanol, 30% CH3CN, and 9.9% H2O. All compounds submitted for mechanistic studies were confirmed to be >95.0% purity by LC-MS traces.

Synthesis Procedures.

General Procedure for the Synthesis of Tetrazole.

Aldehyde (1 mmol) and amine (1 mmol) were added to methanol (5 ml). The solution was stirred at room temperature for 10 mins. Then TMS-N3 (1 mmol) and isocyanide (1 mmol) were added sequentially. The mixture was stirred at room temperature overnight. Solvent was removed by rotatory evaporation and the crude product was purified by flash column chromatography (20-100% ethyl acetate/hexane) to give the final product.

1-{[1-(2,6-dimethylphenyl)-1H-1,2,3,4-tetrazol-5-yl](5-methylthiophen-2-yl)methyl}-4-(furan-2-carbonyl)piperazine. (5aa). Yield: 90.6%. 1H NMR (400 MHz, CDCl3) δ 7.51-7.33 (m, 2H), 7.29-7.20 (m, 1H), 7.20-7.09 (m, 1H), 6.94 (dd, J=3.4, 0.9 Hz, 1H), 6.66 (d, J=3.5 Hz, 1H), 6.56 (dt, J=3.6, 1.2 Hz, 1H), 6.44 (dd, J=3.4, 1.8 Hz, 1H), 4.70 (s, 1H), 3.88-3.60 (m, 4H), 2.85-2.62 (m, 2H), 2.58-2.45 (m, 2H), 2.43 (s, 3H), 2.05 (s, 3H), 1.53 (s, 3H). 13C NMR (101 MHz, CDCl3) δ 158.92, 154.74, 147.71, 143.72, 142.24, 136.41, 135.63, 132.82, 131.48, 131.18, 129.07, 128.96, 128.92, 124.78, 116.54, 111.29, 58.95, 50.27, 17.70, 16.95, 15.36.

C24H26N6O2S, EI-MS: m/z (M+H+): 463.6 (calculated), 463.6 (found).

1-(furan-2-carbonyl)-4-[(5-methylthiophen-2-yl)({1-[(1S)-1-phenylethyl]-1H-1,2,3,4-tetrazol-5-yl})methyl]piperazine. (5ab). Yield: 71.9%. 1H NMR (400 MHz, CDCl3) δ 7.46-7.38 (m, 1H), 7.38-7.27 (m, 3H), 7.24-7.12 (m, 2H), 6.92 (dd, J=3.5, 0.8 Hz, 0.5H), 6.88 (dd, J=3.5, 0.9 Hz, 0.5H), 6.64 (d, J=3.5 Hz, 0.5H), 6.60 (dd, J=3.2, 0.8 Hz, 1H), 6.54-6.49 (m, 0.5H), 6.45-6.36 (m, 1H), 6.08 (q, J=7.1 Hz, 0.5H), 5.54 (q, J=7.0 Hz, 0.5H), 5.11 (s, 0.5H), 5.06 (s, 0.5H), 3.77-3.44 (m, 4H), 2.67-2.53 (m, 1H), 2.53-2.40 (m, 4H), 2.40-2.23 (m, 2H), 2.02-1.89 (m, 3H). 13C NMR (101 MHz, CDCl3) δ 158.94, 158.88, 153.52, 153.32, 147.80, 147.77, 143.76, 143.67, 142.05, 141.78, 139.73, 139.23, 132.92, 132.90, 129.26, 129.16, 129.04, 128.77, 128.67, 128.61, 126.33, 126.10, 124.90, 124.79, 116.64, 116.43, 111.35, 111.27, 60.35, 59.35, 59.11, 58.84, 50.53, 49.66, 22.79, 15.42, 15.37. C24H26N6O2S, EI-MS: m/z (M+H+): 463.6 (calculated), 463.6 (found).

1-[(1-benzyl-1H-1,2,3,4-tetrazol-5-yl)(5-methylthiophen-2-yl)methyl]-4-(furan-2-carbonyl)piperazine. (5ac). Yield: 74.9%. 1H NMR (400 MHz, CDCl3) δ 7.42 (dd, J=1.8, 0.9 Hz, 1H), 7.39-7.28 (m, 3H), 7.20-7.09 (m, 2H), 6.93 (dd, J=3.5, 0.8 Hz, 1H), 6.64 (d, J=3.5 Hz, 1H), 6.58 (dt, J=3.5, 1.1 Hz, 1H), 6.43 (dd, J=3.5, 1.7 Hz, 1H), 5.74 (d, J=15.4 Hz, 1H), 5.48 (d, J=15.4 Hz, 1H), 5.07 (s, 1H), 3.76-3.58 (m, 4H), 2.67-2.51 (m, 2H), 2.43 (s, 3H), 2.44-2.32 (m, 2H). 13C NMR (101 MHz, CDCl3) δ 158.97, 153.78, 147.82, 143.77, 142.04, 133.42, 132.58, 129.30, 129.07, 128.91, 127.52, 124.93, 116.66, 111.38, 59.72, 51.55, 50.09, 15.43. C23H24N6O2S, EI-MS: m/z (M+H+): 449.5 (calculated), 449.5 (found).

1-[(1-cyclohexyl-1H-1,2,3,4-tetrazol-5-yl)(5-methylthiophen-2-yl)methyl]-4-(furan-2carbonyl)piperazine. (5ad). Yield: 85.1%. 1H NMR (400 MHz, CDCl3) δ 7.43 (dd, J=1.8, 0.9 Hz, 1H), 6.96 (dd, J=3.5, 0.9 Hz, 1H), 6.77 (d, J=3.5 Hz, 1H), 6.60 (dq, J=3.4, 1.1 Hz, 1H), 6.44 (dd, J=3.5, 1.8 Hz, 1H), 5.26 (s, 1H), 4.57-4.39 (m, 1H), 3.96-3.59 (m, 4H), 2.78-2.66
(m, 2H), 2.62-2.47 (m, 2H), 2.45 (s, 3H), 2.13-1.85 (m, 6H), 1.85-1.64 (m, 2H), 1.48-1.30 (m, 2H). 13C NMR (101 MHz, CDCl3) δ 159.08, 152.64, 147.84, 143.80, 141.89, 133.91, 128.65, 124.97, 116.75, 111.41, 60.23, 58.55, 50.63, 33.15, 33.10, 25.56, 25.50, 24.91, 15.46.

C22H28N6O2S, EI-MS: m/z (M+H+): 441.6 (calculated), 441.6 (found).

1-(furan-2-carbonyl)-4-({1-[(4-methylbenzenesulfonyl)methyl]-1H-1,2,3,4-tetrazol-5-yl}(5-methylthiophen-2-yl)methyl)piperazine. (5ae). Yield: 80.9%. 1H NMR (400 MHz, CDCl3) δ 7.58-7.46 (m, 2H), 7.43 (dd, J=1.8, 0.9 Hz, 1H), 7.36-7.28 (m, 2H), 6.95 (dd, J=3.5, 0.9 Hz, 1H), 6.84 (d, J=3.5 Hz, 1H), 6.72-6.60 (m, 1H), 6.43 (dd, J=3.5, 1.8 Hz, 1H), 6.15 (d, J=14.4 Hz, 1H), 5.73 (s, 1H), 5.55 (d, J=14.4 Hz, 1H), 4.00-3.66 (m, 4H), 2.75-2.55 (m, 4H), 2.47 (s, 3H), 2.44 (s, 3H). 13C NMR (101 MHz, CDCl3) δ 158.95, 154.97, 147.74, 147.05, 143.80, 142.27, 132.28, 130.56, 130.20, 129.81, 128.95, 124.99, 116.73, 111.37, 65.89, 59.41, 49.56, 21.90, 15.40. C24H26N6O4S2, EI-MS: m/z (M+H+): 527.6 (calculated), 527.4 (found).

1-(furan-2-carbonyl)-4-[(5-methylthiophen-2-yl)(1-pentyl-1H-1,2,3,4-tetrazol-5-yl)methyl]piperazine. (5af). Yield: 62.3%. 1H NMR (400 MHz, CDCl3) δ 7.43 (dd, J=1.8, 0.9 Hz, 1H), 6.96 (dd, J=3.5, 0.9 Hz, 1H), 6.78 (d, J=3.5 Hz, 1H), 6.61 (dq, J=3.4, 1.1 Hz, 1H), 6.44 (dd, J=3.5, 1.8 Hz, 1H), 5.28 (s, 1H), 4.44-4.26 (m, 2H), 3.95-3.68 (m, 4H), 2.88-2.72
(m, 2H), 2.65-2.49 (m, 2H), 2.44 (s, 3H), 1.93-1.76 (m, 2H), 1.40-1.22 (m, 4H), 0.87 (t, J=6.9 Hz, 3H). 13C NMR (101 MHz, CDCl3) δ 159.00, 153.19, 147.76, 143.83, 142.19, 128.97, 125.04, 116.79, 111.42, 59.74, 50.36, 48.01, 29.32, 28.67, 22.18, 15.44, 13.90. C21H28N6O2S, EI-MS: m/z (M+H+): 429.6 (calculated), 429.5 (found).

1-(furan-2-carbonyl)-4-[(5-methylthiophen-2-yl)[1-(naphthalen-2-yl)-1H-1,2,3,4-tetrazol-5-yl]methyl]piperazine. (5ag). Yield: 74.5%. 1H NMR (400 MHz, CDCl3) δ 8.03 (dt, J=8.6, 0.7 Hz, 1H), 8.01-7.91 (m, 2H), 7.91-7.82 (m, 1H), 7.71-7.59 (m, 2H), 7.50 (dd, J=8.7, 2.2 Hz, 1H), 7.43 (dd, J=1.8, 0.9 Hz, 1H), 6.95 (dd, J=3.4, 0.9 Hz, 1H), 6.79 (d, J=3.5 Hz, 1H), 6.63 (dq, J=3.3, 1.0 Hz, 1H), 6.44 (dd, J=3.5, 1.8 Hz, 1H), 5.26 (s, 1H), 3.92-3.64 (m, 4H), 2.94-2.69 (m, 2H), 2.65-2.50 (m, 2H), 2.47 (s, 3H). 13C NMR (101 MHz, CDCl3) δ 159.01, 147.77, 143.79, 133.74, 132.86, 130.82, 130.37, 128.50, 128.33, 128.18, 128.02, 125.02, 124.68, 122.37, 116.69, 111.38, 58.67, 49.67, 15.48. C26H24N6O2S, EI-MS: m/z (M+H+): 485.6 (calculated), 485.6 (found).

1-[(1-tert-butyl-1H-1,2,3,4-tetrazol-5-yl)(5-methylthiophen-2-yl)methyl]-4-(furan-2-carbonyl)piperazine. (5ah). Yield: 79.3%. 1H NMR (400 MHz, CDCl3) δ 7.42 (dd, J=1.8, 0.9 Hz, 1H), 6.94 (dd, J=3.4, 0.9 Hz, 1H), 6.65 (d, J=3.5 Hz, 1H), 6.57 (dq, J=3.4, 1.1 Hz, 1H), 6.43 (dd, J=3.5, 1.8 Hz, 1H), 5.57 (s, 1H), 3.91-3.63 (m, 4H), 3.01-2.81 (m, 2H), 2.66-2.52 (m, 2H), 2.44 (s, 3H), 1.73 (s, 9H). 13C NMR (101 MHz, CDCl3) δ 159.02, 153.29, 147.85, 143.74, 142.21, 129.12, 124.75, 116.57, 111.34, 61.78, 60.10, 49.89, 30.26, 15.44.

C20H26N6O2S, EI-MS: m/z (M+H+): 415.5 (calculated), 415.3 (found).

1-(furan-2-carbonyl)-4-{[1-(4-methoxyphenyl)-1H-1,2,3,4-tetrazol-5-yl](5-methylthiophen-2-yl)methyl}piperazine. (5ai). Yield: 79.5%. 1H NMR (400 MHz, CDCl3) δ 7.42 (dd, J=1.8, 0.9 Hz, 1H), 7.34-7.27 (m, 2H), 7.08-6.99 (m, 2H), 6.94 (dd, J=3.5, 0.9 Hz, 1H), 6.76-6.68 (m, 1H), 6.63-6.55 (m, 1H), 6.43 (dd, J=3.5, 1.8 Hz, 1H), 5.14 (s, 1H), 3.88 (s, 3H), 3.84-3.66 (m, 4H), 2.92-2.71 (m, 2H), 2.56-2.47 (m, 2H), 2.45 (s, 3H). 13C NMR (101 MHz, CDCl3) δ 161.36, 159.01, 153.45, 147.81, 143.78, 128.94, 126.95, 126.07, 124.96, 116.64, 115.10, 111.37, 58.60, 55.84, 49.73, 15.46. C23H24N6O3S, EI-MS: m/z (M+H+): 465.5 (calculated), 465.4 (found).

1-{[1-(2,6-dimethylphenyl)-1H-1,2,3,4-tetrazol-5-yl](5-methylfuran-2-yl)methyl}-4-(furan-2-carbonyl)piperazine. (5aj). Yield: 85.3%. 1H NMR (400 MHz, CDCl3) δ 7.43 (dd, J=1.8, 0.9 Hz, 1H), 7.37 (t, J=7.6 Hz, 1H), 7.25-7.21 (m, 1H), 7.18-7.13 (m, 1H), 6.93 (dd, J=3.5, 0.9 Hz, 1H), 6.43 (dd, J=3.5, 1.8 Hz, 1H), 6.33 (dt, J=3.2, 0.5 Hz, 1H), 5.92-5.87 (m, 1H), 3.81-3.67 (m, 4H), 2.90-2.77 (m, 2H), 2.52-2.38 (m, 2H), 2.22 (s, 3H), 2.04 (s, 3H), 1.64 (s, 3H). 13C NMR (101 MHz, CDCl3) δ 159.02, 153.55, 153.32, 147.80, 145.02, 143.79, 136.13, 136.00, 131.69, 131.17, 128.96, 116.63, 112.98, 111.36, 106.74, 56.79, 50.28, 17.77, 17.10, 13.74. C24H26N6O3, EI-MS: m/z (M+H+): 447.5 (calculated), 447.5 (found).

1-(furan-2-carbonyl)-4-{[5-(methylsulfanyl)thiophen-2-yl]({1-[(1S)-1-phenylethyl]-1H-1,2,3,4-tetrazol-5-yl})methyl}piperazine. (5ak). Yield: 79.6%. 1H NMR (400 MHz, CDCl3) δ 7.47-7.40 (m, 1H), 7.40-7.25 (m, 3H), 7.25-7.11 (m, 2H), 6.95 (dd, J=3.5, 0.8 Hz, 0.5H), 6.93-6.84 (m, 1H), 6.80 (d, J=3.7 Hz, 0.5H), 6.73 (d, J=3.6 Hz, 0.5H), 6.62 (d, J=3.7 Hz, 0.5H), 6.49-6.36 (m, 1H), 6.04 (q, J=7.0 Hz, 0.5H), 5.64 (q, J=7.0 Hz, 0.5H), 5.15 (s, 0.5H), 5.13 (s, 0.5H), 3.85-3.65 (m, 2H), 3.65-3.42 (m, 2H), 2.68-2.56 (m, 1H), 2.49 (s, 1.5H), 2.47 (s, 1.5H), 2.53-2.32 (m, 3H), 2.12-1.95 (m, 3H). 13C NMR (101 MHz, CDCl3) δ 158.93, 158.85, 152.98, 152.81, 147.69, 147.67, 143.80, 143.71, 139.94, 139.64, 139.60, 139.08, 137.03, 137.01, 129.69, 129.46, 129.26, 129.23, 129.22, 128.91, 128.78, 126.22, 126.07, 116.73, 116.53, 111.37, 111.29, 60.08, 59.28, 59.18, 58.94, 50.34, 49.56, 22.84, 22.69, 21.65, 21.50.

C24H26N6O2S2, EI-MS: m/z (M+H+): 495.6 (calculated), 495.8 (found).

1-(furan-2-carbonyl)-4-({1-[(1S)-1-phenylethyl]-1H-1,2,3,4-tetrazol-5-yl}(thiophen-2-yl)methyl)piperazine. (5al). Yield: 78.4%. 1H NMR (400 MHz, CDCl3) δ 7.48-7.39 (m, 1H), 7.39-7.24 (m, 4H), 7.24-7.12 (m, 2H), 7.02-6.90 (m, 1.5H), 6.90-6.84 (m, 1H), 6.84-6.77 (m, 0.5H), 6.49-6.35 (m, 1H), 6.10 (q, J=7.0 Hz, 0.5H), 5.68 (q, J=7.0 Hz, 0.5H), 5.28 (s, 1H), 3.82-3.63 (m, 2H), 3.63-3.35 (m, 2H), 2.71-2.52 (m, 1H), 2.52-2.29 (m, 3H), 2.01-1.89 (m, 3H). 13C NMR (101 MHz, CDCl3) δ 158.75, 158.66, 153.25, 153.04, 147.51, 147.50, 143.66, 143.57, 139.63, 138.94, 135.32, 135.16, 129.04, 128.99, 128.77, 128.59, 128.53, 127.02, 126.79, 126.61, 126.54, 126.14, 125.96, 116.40, 116.21, 111.18, 111.10, 59.56, 58.89, 58.69, 58.66, 50.19, 49.33, 22.67, 22.50. C23H24N6O2S, EI-MS: m/z (M+H+): 449.5 (calculated), 449.6 (found).

1-{[1-(2,6-dimethylphenyl)-1H-1,2,3,4-tetrazol-5-yl] (thiophen-2-yl)methyl}-4-(furan-2 carbonyl)piperazine. (5am). Yield: 86.4%. 1H NMR (400 MHz, CDCl3) δ 7.42 (dd, J=1.8, 0.9 Hz, 1H), 7.39 (t, J=7.6 Hz, 1H), 7.34-7.28 (m, 1H), 7.28-7.21 (m, 1H), 7.17-7.09 (m, 1H), 6.98-6.88 (m, 3H), 6.43 (dd, J=3.5, 1.8 Hz, 1H), 4.81 (s, 1H), 3.94-3.64 (m, 4H), 2.90-2.66 (m, 2H), 2.57-2.42 (m, 2H), 2.05 (s, 3H), 1.48 (s, 3H). 13C NMR (101 MHz, CDCl3) δ 158.98, 154.69, 147.82, 143.80, 136.48, 135.75, 135.37, 131.50, 131.32, 129.28, 129.08, 129.06, 127.59, 126.93, 116.70, 111.40, 58.74, 50.38, 17.83, 16.96. C23H24N6O2S, m/z (M+H+): 449.5 (calculated), 449.5 (found).

1-{[1-(2,6-dimethylphenyl)-1H-1,2,3,4-tetrazol-5-yl] (thiophen-3-yl)methyl}-4-(furan-2-carbonyl)piperazine. (5an). Yield: 81.6%. 1H NMR (400 MHz, CDCl3) δ 7.42 (dd, J=1.8, 0.9 Hz, 1H), 7.38 (t, J=7.6 Hz, 1H), 7.30-7.20 (m, 2H), 7.15-7.02 (m, 3H), 6.95 (dd, J=3.5, 0.9 Hz, 1H), 6.44 (dd, J=3.5, 1.8 Hz, 1H), 4.59 (s, 1H), 3.91-3.66 (m, 4H), 2.81-2.56 (m, 2H), 2.56-2.36 (m, 2H), 2.03 (s, 3H), 1.36 (s, 3H). 13C NMR (101 MHz, CDCl3) δ 158.97, 147.84, 143.80, 136.62, 135.53, 131.55, 131.25, 129.06, 129.00, 128.13, 126.89, 116.71, 111.41, 59.43, 50.84, 17.80, 16.75. C23H24N6O2S, EI-MS: m/z (M+H+): 449.5 (calculated), 449.5 (found).

1-(furan-2-carbonyl)-4-[phenyl({1-[(1S)-1-phenylethyl]-1H-1,2,3,4-tetrazol-5-yl})methyl]piperazine. (5ao). Yield: 68.9%. 1H NMR (400 MHz, CDCl3) δ 7.47-7.38 (m, 1H), 7.38-7.27 (m, 6H), 7.27-7.18 (m, 2H), 7.17-7.05 (m, 2H), 6.96-6.84 (m, 1H), 6.47-6.35 (m, 1H), 5.93 (q, J=7.0 Hz, 0.5H), 5.47 (q, J=7.1 Hz, 0.5H), 4.92 (s, 0.5H), 4.79 (s, 0.5H), 3.82-3.50 (m, 4H), 2.69-2.55 (m, 0.5H), 2.49-2.26 (m, 3.5H), 1.96-1.81 (m, 3H). 13C NMR (101 MHz, CDCl3) δ 158.82, 158.74, 154.00, 153.62, 147.64, 143.67, 143.59, 139.47, 138.82, 133.71, 133.60, 129.16, 128.97, 128.92, 128.87, 128.66, 128.62, 128.60, 128.50, 126.30, 125.95, 116.43, 116.27, 111.22, 111.16, 64.55, 64.44, 58.59, 58.52, 53.49, 50.87, 50.37, 22.45, 22.43. C25H26N6O2, EI-MS: m/z (M+H+): 443.5 (calculated), 443.6 (found).

1-{[1-(2,6-dimethylphenyl)-1H-1,2,3,4-tetrazol-5-yl](2-methylphenyl)methyl}-4-(furan-2-carbonyl)piperazine. (5ap). Yield: 76.3%. 1H NMR (400 MHz, CDCl3) δ 7.42 (dd, J=1.8, 0.9 Hz, 1H), 7.40-7.29 (m, 2H), 7.26-7.19 (m, 1H), 7.17-7.04 (m, 2H), 7.04-6.98 (m, 2H), 6.96 (dd, J=3.4, 0.9 Hz, 1H), 6.44 (dd, J=3.5, 1.8 Hz, 1H), 4.64 (s, 1H), 3.86 (s, 4H), 2.77-2.64 (m, 2H), 2.62-2.50 (m, 2H), 2.00 (s, 3H), 1.68 (s, 3H), 0.97 (s, 3H). 13C NMR (101 MHz, CDCl3) δ 158.96, 156.13, 147.86, 143.78, 137.37, 137.32, 134.93, 131.48, 131.26, 130.76, 130.14, 129.11, 128.83, 126.86, 116.65, 111.38, 60.73, 51.29, 18.72, 17.69, 16.19.

C26H28N6O2, EI-MS: m/z (M+H+): 457.6 (calculated), 457.6 (found).

1-(furan-2-carbonyl)-4-({1-[(1S)-1-phenylethyl]-1H-1,2,3,4-tetrazol-5-yl}(thian-4-yl)methyl)piperazine. (5aq). Yield: 62.8%. 1H NMR (400 MHz, CDCl3) δ 7.48-7.24 (m, 5H), 7.23-7.12 (m, 1H), 6.95 (dd, J=3.5, 0.9 Hz, 0.5H), 6.86 (dd, J=3.4, 0.9 Hz, 0.5H), 6.50-6.35 (m, 1H), 5.63-5.45 (m, 1H), 4.00-3.35 (m, 5H), 2.76-2.33 (m, 7H), 2.33-1.98 (m, 6H), 1.50-1.22 (m, 2H), 0.90-0.76 (m, 0.5H), 0.40-0.17 (m, 0.5H). 13C NMR (101 MHz, CDCl3) δ 159.01, 158.94, 152.38, 151.30, 147.70, 143.81, 143.67, 139.65, 139.61, 129.39, 129.36, 129.09, 128.99, 126.37, 126.18, 116.79, 116.40, 111.41, 111.27, 63.43, 63.06, 59.03, 58.75, 38.85, 37.99, 31.90, 31.41, 31.07, 28.48, 28.34, 28.27, 28.06, 23.68, 22.95.

C24H30N6O2S, EI-MS: m/z (M+H+): 467.6 (calculated), 467.6 (found).

1-{[1-(2,6-dimethylphenyl)-1H-1,2,3,4-tetrazol-5-yl] (phenyl)methyl}-4-(furan-2-carbonyl)piperazine. (5ar). Yield: 90.3%. 1H NMR (400 MHz, CDCl3) δ 7.42 (dd, J=1.8, 0.9 Hz, 1H), 7.37 (t, J=7.6 Hz, 1H), 7.31-7.18 (m, 4H), 7.17-7.10 (m, 2H), 7.09-7.02 (m, 1H), 6.95 (dd, J=3.5, 0.9 Hz, 1H), 6.43 (dd, J=3.5, 1.8 Hz, 1H), 4.38-4.24 (m, 1H), 4.01-3.67 (m, 4H), 2.70-2.45 (m, 4H), 2.02 (s, 3H), 1.09 (s, 3H). 13C NMR (101 MHz, CDCl3) δ 158.95, 147.87, 143.78, 136.94, 135.03, 131.48, 131.25, 129.54, 129.24, 129.07, 128.94, 128.90, 116.68, 111.40, 65.35, 51.52, 17.76, 16.60. C25H26N6O2, EI-MS: m/z (M+H+): 443.5 (calculated), 443.6 (found).

1-{1-[1-(2,6-dimethylphenyl)-1H-1,2,3,4-tetrazol-5-yl]-2-phenylethyl}-4-(furan-2-carbonyl)piperazine. (5as). Yield: 83.9%. 1H NMR (400 MHz, CDCl3) δ 7.46 (dd, J=1.8, 0.9 Hz, 1H), 7.31 (t, J=7.6 Hz, 1H), 7.22-7.06 (m, 6H), 7.06-6.94 (m, 2H), 6.47 (dd, J=3.5, 1.8 Hz, 1H), 3.90-3.56 (m, 5H), 3.54-3.39 (m, 1H), 3.13 (dd, J=12.6, 3.2 Hz, 1H), 3.07-2.91 (m, 2H), 2.62-2.45 (m, 2H), 2.07 (s, 3H), 0.97 (s, 3H). 13C NMR (101 MHz, CDCl3) δ 159.18, 154.40, 147.85, 143.82, 137.57, 136.77, 135.74, 131.59, 130.93, 129.71, 128.76, 128.62, 128.60, 126.83, 116.73, 111.43, 61.90, 48.85, 31.36, 17.91, 15.76. C26H28N6O2, EI-MS: m/z (M+H+): 457.6 (calculated), 457.6 (found).

1-(furan-2-carbonyl)-4-(2-phenyl-1-{1-[(1S)-1-phenyl-ethyl]-1H-1,2,3,4-tetrazol-5-yl}ethyl)piperazine. (5at). Yield: 70.9%. 1H NMR (400 MHz, CDCl3) δ 7.48-7.41 (m, 1H), 7.35-7.14 (m, 5H), 7.12-6.95 (m, 4H), 6.93-6.83 (m, 2H), 6.51-6.37 (m, 1H), 5.69 (q, J=7.0 Hz, 0.5H), 4.89 (q, J=7.0 Hz, 0.5H), 4.09-3.95 (m, 1H), 3.84-3.64 (m, 2H), 3.56-3.42 (m, 2H), 3.41-3.30 (m, 1H), 3.26-3.11 (m, 1H), 2.77-2.68 (m, 1H), 2.66-2.57 (m, 1H), 2.54-2.29 (m, 2H), 1.94 (d, J=7.0 Hz, 1.5H), 1.65 (d, J=7.0 Hz, 1.5H). 13C NMR (101 MHz, CDCl3) δ 159.11, 158.96, 153.62, 152.95, 147.81, 143.85, 143.73, 139.92, 139.20, 137.36, 137.28, 129.32, 129.22, 129.14, 129.07, 128.86, 128.62, 128.52, 128.49, 127.06, 126.54, 126.12, 125.86, 116.78, 116.53, 111.44, 111.34, 61.69, 61.05, 58.44, 58.31, 35.78, 33.07, 22.56, 22.17.

C26H28N6O2. EI-MS: m/z (M+H+): 457.6 (calculated), 457.6 (found).

1-[1-(1-benzyl-1H-1,2,3,4-tetrazol-5-yl)-2-phenylethyl]-4-(furan-2-carbonyl)piperazine. (5au). Yield: 87.3%. 1H NMR (400 MHz, CDCl3) δ 7.50-7.40 (m, 1H), 7.36-7.21 (m, 3H), 7.21-7.09 (m, 3H), 7.04-6.88 (m, 5H), 6.51-6.40 (m, 1H), 5.38 (d, J=15.5 Hz, 1H), 5.00 (d, J=15.5 Hz, 1H), 4.03 (dd, J=10.6, 3.9 Hz, 1H), 3.76-3.48 (m, 4H), 3.37 (dd, J=13.0, 10.6 Hz, 1H), 3.20 (dd, J=13.0, 3.9 Hz, 1H), 2.69-2.42 (m, 4H). 13C NMR (101 MHz, CDCl3) δ 159.06, 153.70, 147.85, 143.81, 137.30, 133.55, 129.26, 129.22, 128.86, 128.79, 127.31, 126.92, 116.71, 111.42, 61.40, 50.80, 49.20, 34.46. C25H26N6O2, EI-MS: m/z (M+H+): 443.5 (calculated), 443.6 (found).

1-(furan-2-carbonyl)-4-(1-{1-[(4-methylbenzenesulfo-nyl)methyl]-1H-1,2,3,4-tetrazol-5-yl}-2-phenylethyl)pip-erazine. (5av). Yield: 74.8%. 1H NMR (400 MHz, CDCl3) δ 7.46 (dd, J=1.8, 0.9 Hz, 1H), 7.34-7.13 (m, 9H), 6.98 (dd, J=3.5, 0.9 Hz, 1H), 6.46 (dd, J=3.5, 1.8 Hz, 1H), 5.75 (d, J=14.4 Hz, 1H), 5.36 (d, J=14.4 Hz, 1H), 4.80 (dd, J=9.6, 4.7 Hz, 1H), 3.93-3.60 (m, 4H), 3.52-3.38 (m, 1H), 3.38-3.23 (m, 1H), 2.90-2.64 (m, 4H), 2.39 (s, 3H). 13C NMR (101 MHz, CDCl3) δ 159.02, 155.08, 147.72, 146.81, 143.83, 137.38, 131.73, 130.39, 129.61, 128.72, 128.67, 126.89, 116.72, 111.39, 65.48, 60.58, 49.05, 32.77, 21.82. C26H28N6O4S.

EIMS: m/z (M+H+): 521.6 (calculated), 521.6 (found).

1-(furan-2-carbonyl)-4-(2-phenyl-1-{1-[(1S)-1-phenyl-ethyl]-1H-1,2,3,4-tetrazol-5-yl}ethyl)piperazine. (5aw). Yield: 70.8%. 1H NMR (400 MHz, CDCl3) δ 7.53-7.37 (m, 1H), 7.35-7.14 (m, 5H), 7.14-6.96 (m, 4H), 6.96-6.78 (m, 2H), 6.54-6.38 (m, 1H), 5.68 (q, J=7.1 Hz, 0.5H), 4.88 (q, J=7.0 Hz, 0.5H), 4.11-3.93 (m, 1H), 3.88-3.60 (m, 2H), 3.60-3.41 (m, 2H), 3.41-3.28 (m, 1H), 3.28-3.07 (m, 1H), 2.84-2.67 (m, 1H), 2.67-2.56 (m, 1H), 2.57-2.28 (m, 2H), 1.94 (d, J=7.1 Hz, 1.5H), 1.64 (d, J=7.0 Hz, 1.5H). 13C NMR (101 MHz, CDCl3) δ 159.13, 158.98, 153.63, 152.96, 147.82, 143.86, 143.75, 139.93, 139.21, 137.37, 137.29, 129.33, 129.24, 129.16, 129.08, 128.88, 128.64, 128.54, 128.51, 127.08, 126.55, 126.13, 125.87, 116.81, 116.56, 114.36, 111.46, 111.36, 61.72, 61.07, 58.46, 58.34, 49.13, 35.82, 33.08, 22.58, 22.18. C26H28N6O2, EI-MS: m/z (M+H+): 457.6 (calculated), 457.6 (found).

1-[(5-methylthiophen-2-yl)({1-[(1S)-1-phenylethyl]-1H-1,2,3,4-tetrazol-5-yl}))methyl]-4-(pyridin-2-yl)piperazine. (5ax). Yield: 87.9%. 1H NMR (400 MHz, CDCl3) δ 8.21-8.06 (m, 1H), 7.49-7.37 (m, 1H), 7.37-7.13 (m, 5H), 6.68 (dd, J=3.6, 1.3 Hz, 1H), 6.65-6.46 (m, 3H), 6.18 (q, J=7.1 Hz, 0.5H), 5.66 (q, J=7.0 Hz, 0.5H), 5.13 (s, 0.5H), 5.10 (s, 0.5H), 3.52-3.26 (m, 4H), 2.67-2.58 (m, 1H), 2.56-2.48 (m, 1H), 2.49-2.30 (m, 5H), 2.05-1.91 (m, 3H). 13C NMR (101 MHz, CDCl3) δ 159.24, 159.22, 153.70, 153.47, 147.95, 147.90, 141.79, 141.51, 139.60, 139.37, 137.53, 137.47, 133.53, 133.05, 129.15, 129.12, 128.91, 128.66, 128.61, 128.43, 126.44, 126.27, 124.81, 124.69, 113.54, 113.32, 107.12, 107.00, 60.65, 59.73, 59.06, 58.73, 50.23, 49.65, 45.08, 44.99, 22.84, 22.77, 15.40, 15.37. C24H27N7S, EI-MS: m/z (M+H+): 446.6 (calculated), 446.8 (found).

1-[(5-methylthiophen-2-yl)({1-[(1S)-1-phenylethyl]-1H-1,2,3,4-tetrazol-5-yl})methyl]-4-[3-(trifluoromethyl)pyri-din-2-yl]piperazine. (5ay). Yield: 74.6%. 1H NMR (400 MHz, CDCl3) δ 8.49-8.32 (m, 1H), 7.90-7.74 (m, 1H), 7.43-7.22 (m, 5H), 7.04-6.88 (m, 1H), 6.77-6.67 (m, 1H), 6.64-6.53 (m, 1H), 6.22 (q, J=7.1 Hz, 0.5H), 5.74 (q, J=7.0 Hz, 0.5H), 5.14 (s, 0.5H), 5.12 (s, 0.5H), 3.33-3.11 (m, 4H), 2.73-2.54 (m, 2H), 2.54-2.39 (m, 5H), 2.11-1.94 (m, 3H). 13C NMR (101 MHz, CDCl3) δ 159.39, 159.22, 153.81, 153.53, 151.08, 150.98, 141.78, 141.50, 139.57, 139.45, 137.34, 137.29, 134.14, 133.20, 129.15, 128.87, 128.66, 128.64, 128.29, 126.51, 126.37, 124.82, 124.70, 117.08, 116.72, 116.60, 116.46, 60.68, 59.92, 59.09, 58.73, 50.48, 50.46, 50.31, 50.11, 22.89, 22.78, 15.43, 15.41. C25H26F3N7S, EI-MS: m/z (M+H+): 514.6 (calculated), 514.6 (found).

1-benzoyl-4-[(1-benzyl-1H-1,2,3,4-tetrazol-5-yl)(5-methylthiophen-2-yl)methyl]piperazine. (5az). Yield: 80.4%. 1H NMR (400 MHz, CDCl3) δ 7.47-7.28 (m, 8H), 7.20-7.03 (m, 2H), 6.69-6.49 (m, 2H), 5.73 (d, J=15.4 Hz, 1H), 5.45 (d, J=15.4 Hz, 1H), 5.07 (s, 1H), 3.87-3.03 (m, 4H), 2.68-2.48 (m, 2H), 2.45 (s, 3H), 2.43-2.17 (m, 2H). 13C NMR (101 MHz, CDCl3) δ 170.29, 153.71, 142.06, 135.55, 133.40, 132.80, 129.86, 129.30, 129.08, 128.83, 128.54, 127.52, 127.15, 124.94, 59.65, 51.52, 49.96, 15.45. C25H26N6OS, EI-MS: m/z (M+H+): 459.6 (calculated), 459.4 (found).

1-benzoyl-4-[(5-methylthiophen-2-yl)({1-[(1S)-1-pheny-lethyl]-1H-1,2,3,4-tetrazol-5-yl})methyl]piperazine. (5ba). Yield: 81.7%. 1H NMR (400 MHz, CDCl3) δ 7.48-7.23 (m, 8H), 7.22-7.11 (m, 2H), 6.67-6.59 (m, 1H), 6.59-6.56 (m, 0.5H), 6.54-6.48 (m, 0.5H), 6.06 (q, J=7.0 Hz, 0.5H), 5.53 (q, J=7.0 Hz, 0.5H), 5.13 (s, 0.5H), 5.07 (s, 0.5H), 3.80-3.45 (m, 2H), 3.42-3.05 (m, 2H), 2.66-2.44 (m, 2H), 2.45 (s, 1.5H), 2.42 (s, 1.5H), 2.43-2.17 (m, 2H), 2.03-1.93 (m, 3H). 13C NMR (101 MHz, CDCl3) δ 170.25, 170.16, 153.46, 153.24, 142.06, 141.77, 139.70, 139.13, 135.56, 135.43, 133.21, 132.97, 129.84, 129.73, 129.26, 129.13, 128.98, 128.76, 128.66, 128.50, 128.44, 127.08, 127.06, 126.31, 126.07, 124.89, 124.77, 60.24, 59.25, 59.06, 58.82, 50.37, 22.73, 22.70, 15.42, 15.36. C26H28N6OS, EI-MS: m/z (M+H+): 473.6 (calculated), 473.6 (found).

1-benzoyl-4-{[1-(2,6-dimethylphenyl)-1H-1,2,3,4-tetra-zol-5-yl](5-methylthiophen-2-yl)methyl}piperazine. (5bb). Yield: 78.3%. 1H NMR (400 MHz, CDCl3) δ 7.45-7.30 (m, 6H), 7.26-7.22 (m, 1H), 7.18-7.08 (m, 1H), 6.74-6.60 (m, 1H), 6.60-6.50 (m, 1H), 4.70 (s, 1H), 3.88-3.58 (m, 2H), 3.58-3.26 (m, 2H), 2.83-2.65 (m, 2H), 2.55-2.31 (m, 2H), 2.42 (s, 3H), 2.04 (s, 3H), 1.53 (s, 3H). 13C NMR (101 MHz, CDCl3) δ 170.32, 154.75, 142.33, 136.56, 135.78, 135.60, 133.02, 131.61, 131.25, 129.87, 129.15, 129.06, 129.01, 128.55, 127.19, 124.88, 58.99, 17.83, 17.09, 15.47. C26H28N6OS, EI-MS: m/z (M+H+): 473.6 (calculated), 473.4 (found).

1-{[1-(2,6-dimethylphenyl)-1H-1,2,3,4-tetrazol-5-yl](5-methylthiophen-2-yl)methyl}-4-(2-methylphenyl)pipera-zine. (5bc). Yield: 85.6%. 1H NMR (400 MHz, CDCl3) δ 7.38 (t, J=7.6 Hz, 1H), 7.30-7.22 (m, 1H), 7.20-7.08 (m, 3H), 7.03-6.89 (m, 2H), 6.69 (d, J=3.5 Hz, 1H), 6.61-6.49 (m, 1H), 4.71 (s, 1H), 3.05-2.73 (m, 6H), 2.68-2.52 (m, 2H), 2.44 (s, 3H), 2.22 (s, 3H), 2.09 (s, 3H), 1.55 (s, 3H). 13C NMR (101 MHz, CDCl3) δ 155.15, 151.33, 142.03, 136.59, 135.97, 133.91, 132.70, 131.82, 131.14, 128.99, 128.97, 128.91, 126.67, 124.76, 123.35, 119.13, 59.37, 51.79, 50.85, 17.97, 17.94, 17.12, 15.51. C26H30N6S, EI-MS: m/z (M+H+): 459.6 (calculated), 459.6 (found).

1-{[1-(2,6-dimethylphenyl)-1H-1,2,3,4-tetrazol-5-yl](5-methylthiophen-2-yl)methyl}-4-(pyridin-2-yl)piperazine. (5bd). Yield: 73.1%. 1H NMR (400 MHz, CDCl3) δ 8.13 (ddd, J=4.9, 2.0, 1.0 Hz, 1H), 7.49-7.33 (m, 2H), 7.25-7.21 (m, 1H), 7.18-7.12 (m, 1H), 6.69 (d, J=3.5 Hz, 1H), 6.62-6.53 (m, 3H), 4.71 (s, 1H), 3.51 (t, J=5.1 Hz, 4H), 2.86-2.66 (m, 2H), 2.63-2.46 (m, 2H), 2.42 (s, 3H), 2.05 (s, 3H), 1.56 (s, 3H). 13C NMR (101 MHz, CDCl3) δ 154.92, 147.64, 142.10, 137.80, 136.45, 135.96, 133.24, 131.71, 131.17, 129.03, 129.01, 128.96, 124.77, 113.41, 107.27, 59.19, 50.02, 45.35, 17.84, 17.12, 15.45. C24H27N7S, EI-MS: m/z (M+H+): 446.6 (calculated), 446.6 (found).

4-bromo-N-[3-({1-[(1S)-1-phenylethyl]-1H-1,2,3,4-tetra-zol-5-yl}[4-(pyridin-2-yl)piperazin-1-yl]methyl)phenyl]benzamide. (5be). Yield: 71.3%. 1H NMR (400 MHz, CDCl3) δ 8.23 (d, J=6.0 Hz, 1H), 8.16-8.02 (m, 1H), 7.83-7.66 (m, 3H), 7.65-7.50 (m, 3H), 7.49-7.34 (m, 1H), 7.34-7.16 (m, 4H), 7.16-7.05 (m, 1.5H), 7.01-6.88 (m, 0.5H), 6.68-6.41 (m, 2H), 6.07 (q, J=7.0 Hz, 0.5H), 5.70 (q, J=6.9 Hz, 0.5H), 4.84 (s, 0.5H), 4.78 (s, 0.5H), 3.54-3.43 (m, 2H), 3.43-3.28 (m, 2H), 2.68-2.53 (m, 1H), 2.52-2.27 (m, 3H), 1.94 (d, J=7.0 Hz, 1.5H), 1.88 (d, J=7.0 Hz, 1.5H). 13C NMR (101 MHz, CDCl3) δ 165.12, 165.01, 159.33, 159.30, 154.34, 153.86, 148.00, 147.97, 139.61, 139.18, 138.72, 138.43, 137.64, 137.60, 135.47, 134.72, 133.68, 133.61, 132.07, 132.04, 129.75, 129.40, 129.28, 129.18, 128.93, 128.91, 128.75, 128.72, 126.84, 126.75, 126.58, 126.21, 125.28, 120.94, 120.88, 120.61, 113.68, 113.60, 107.25, 107.16, 64.97, 64.94, 59.01, 58.82, 50.79, 50.72, 45.21, 45.11, 22.82, 22.72. C32H31BrN8O, EI-MS: m/z (M+H+): 624.6 (calculated), 624.6 (found).

1-{[1-(2,6-dimethylphenyl)-1H-1,2,3,4-tetrazol-5-yl](5-methylthiophen-2-yl)methyl}-4-[3-(trifluoromethyl)pyridin-2-yl]piperazine. (5bf). Yield: 69.3%. 1H NMR (400 MHz, CDCl3) δ 8.40-8.35 (m, 1H), 7.83-7.76 (m, 1H), 7.38 (t, J=7.6 Hz, 1H), 7.27-7.22 (m, 1H), 7.18-7.11 (m, 1H), 6.97-6.89 (m, 1H), 6.74-6.66 (m, 1H), 6.60-6.53 (m, 1H), 4.73 (s, 1H), 3.47-3.08 (m, 4H), 2.91-2.71 (m, 2H), 2.70-2.51 (m, 2H), 2.43 (s, 3H), 2.07 (s, 3H), 1.55 (s, 3H). 13C NMR (101 MHz, CDCl3) δ 159.31, 151.07, 137.37, 137.32, 136.50, 136.03, 131.73, 131.17, 129.03, 128.96, 125.41, 124.82, 116.81, 116.68, 116.37, 59.22, 50.49, 50.32, 17.89, 17.11, 15.49. C25H26F3N7S, EI-MS: m/z (M+H+): 514.6 (calculated), 514.6 (found).

1-(1-{[1-(2,6-dimethylphenyl)-1H-1,2,3,4-tetrazol-5-yl](5-methylthiophen-2-yl)methyl}piperidin-4-yl)-2,3-dihydro-1H-1,3-benzodiazol-2-one. (5bg). Yield: 72.3%. 1H NMR (400 MHz, CDCl3) δ 10.29 (s, 1H), 7.40 (t, J=7.6 Hz, 1H), 7.32-7.27 (m, 1H), 7.21-7.13 (m, 2H), 7.12-7.07 (m, 1H), 7.07-7.00 (m, 2H), 6.77-6.66 (m, 1H), 6.65-6.54 (m, 1H), 4.77 (s, 1H), 4.44-4.17 (m, 1H), 3.35-3.16 (m, 1H), 3.09-2.83 (m, 1H), 2.65-2.32 (m, 6H), 2.32-2.17 (m, 1H), 2.14 (s, 3H), 1.87-1.70 (m, 2H), 1.59 (s, 3H). 13C NMR (101 MHz, CDCl3) δ 155.30, 155.08, 141.94, 136.44, 135.97, 133.57, 131.19, 129.02, 128.21, 124.78, 121.34, 121.11, 109.90, 109.63, 59.01, 51.48, 50.65, 48.84, 29.52, 29.25, 17.89, 17.16, 15.48. C27H29N7OS, EIMS: m/z (M+H+): 500.6 (calculated), 500.4 (found).

1-{1-[(5-bromothiophen-2-yl)({1-[(1S)-1-phenylethyl]-1H-1,2,3,4-tetrazol-5-yl})methyl]piperidin-4-yl}-2,3-dihydro-1H-1,3-benzodiazol-2-one. (5bh). Yield: 70.1%. 1H NMR (400 MHz, CDCl3) δ 10.53 (s, 1H), 7.48-7.27 (m, 5H), 7.21-6.99 (m, 4H), 6.95 (d, J=3.8 Hz, 0.5H), 6.87 (d, J=3.8 Hz, 0.5H), 6.68 (d, J=3.8 Hz, 0.5H), 6.56 (d, J=3.8 Hz, 0.5H), 6.12 (q, J=7.0 Hz, 0.5H), 5.76 (q, J=7.0 Hz, 0.5H), 5.27 (s, 0.5H), 5.21 (s, 1H), 4.33-4.06 (m, 1H), 3.11-2.90 (m, 1H), 2.90-2.78 (m, 0.5H), 2.73-2.62 (m, 0.5H), 2.59-2.21 (m, 3H), 2.21-1.99 (m, 4H), 1.86-1.56 (m, 2H). 13C NMR (101 MHz, CDCl3) δ 155.33, 155.31, 152.84, 152.74, 139.43, 139.21, 137.96, 137.56, 129.43, 129.34, 129.30, 129.28, 129.12, 129.00, 128.97, 128.84, 128.82, 128.72, 128.26, 128.19, 126.69, 126.27, 121.42, 121.31, 121.06, 120.95, 114.13, 113.82, 110.01, 109.90, 109.51, 109.12, 60.01, 59.26, 58.83, 51.00, 50.51, 50.19, 49.04, 48.55, 29.47, 29.20, 29.04, 22.82, 22.70. C26H26BrN7OS, EI-MS: m/z (M+H+): 565.5 (calculated), 565.3 (found).

1-(1-{[5-(methylsulfanyl)thiophen-2-yl]({1-[(1S)-1-phenylethyl]-1H-1,2,3,4-tetrazol-5-yl})methyl}piperidin-4-yl)-2,3-dihydro-1H-1,3-benzodiazol-2-one. (5bi). Yield: 68.2%. 1H NMR (400 MHz, CDCl3) δ 10.31-10.06 (2S, 1H), 7.55-7.22 (m, 5H), 7.22-6.98 (m, 4H), 6.98-6.63 (m, 2H), 6.17 (q, J=7.0 Hz, 0.5H), 5.72 (q, J=7.0 Hz, 0.5H), 5.21 (2S, 1H), 4.32-4.05 (m, 1H), 3.14-2.85 (m, 1H), 2.85-2.69 (m, 1H), 2.60-1.99 (m, 10H), 1.91-1.53 (m, 2H). 13C NMR (101 MHz, CDCl3) δ 155.25, 153.29, 153.17, 139.63, 139.54, 139.33, 139.20, 138.03, 137.83, 129.91, 129.68, 129.50, 129.30, 129.27, 129.19, 129.09, 128.83, 128.80, 128.73, 128.22, 128.15, 126.74, 126.38, 126.32, 121.44, 121.33, 121.11, 121.04, 109.97, 109.86, 109.63, 109.24, 60.40, 59.53, 59.23, 58.81, 51.44, 50.59, 50.48, 49.25, 48.76, 29.54, 29.26, 29.16, 29.12, 22.85, 21.87, 21.72. C27H29N7OS2, EI-MS: m/z (M+H+): 532.7 (calculated), 532.7 (found).

1-{1-[(1-benzyl-1H-1,2,3,4-tetrazol-5-yl)(thiophen-2-yl)methyl]piperidin-4-yl}-2,3-dihydro-1H-1,3-benzodiazol-2- one. (5bj). Yield: 86.3%. 1H NMR (400 MHz, DMSO-d6) δ 10.79 (s, 1H), 7.66-7.51 (m, 1H), 7.49-7.21 (m, 5H), 7.14-6.86 (m, 6H), 6.01-5.71 (m, 3H), 4.08-3.87 (m, 1H), 3.19-3.01 (m, 1H), 2.99-2.80 (m, 1H), 2.43-2.20 (m, 2H), 2.20-2.01 (m, 2H), 1.72-1.44 (m, 2H). 13C NMR (101 MHz, DMSO-d6) δ 153.67, 153.61, 135.98, 134.81, 129.12, 8.40-8.35 (m, 1H), 7.83-7.76 (m, 1H), 7.38 (t, J=7.6 Hz, 1H), 7.27-7.22 (m, 1H), 7.18-7.11 (m, 1H), 6.97-6.89 (m, 1H), 6.74-6.66 (m, 1H), 6.60-6.53 (m, 1H), 4.73 (s, 1H), 3.47-3.08 (m, 4H), 2.91-2.71 (m, 2H), 2.70-2.51 (m, 2H), 2.43 (s, 3H), 2.07 (s, 3H), 1.55 (s, 3H). 13C NMR (101 MHz, CDCl3) δ 159.31, 151.07, 137.37, 137.32, 136.50, 136.03, 131.73, 131.17, 129.03, 128.96, 125.41, 124.82, 116.81, 116.68, 116.37, 59.22, 50.49, 50.32, 17.89, 17.11, 15.49. C25H26F3N7S, EI-MS: m/z (M+H+): 514.6 (calculated), 514.6 (found).

1-(1-{[1-(2,6-dimethylphenyl)-1H-1,2,3,4-tetrazol-5-yl](5-methylthiophen-2-yl)methyl}piperidin-4-yl)-2,3-dihydro-1H-1,3-benzodiazol-2-one. (5bg). Yield: 72.3%. 1H NMR (400 MHz, CDCl3) δ 10.29 (s, 1H), 7.40 (t, J=7.6 Hz, 1H), 7.32-7.27 (m, 1H), 7.21-7.13 (m, 2H), 7.12-7.07 (m, 1H), 7.07-7.00 (m, 2H), 6.77-6.66 (m, 1H), 6.65-6.54 (m, 1H), 4.77 (s, 1H), 4.44-4.17 (m, 1H), 3.35-3.16 (m, 1H), 3.09-2.83 (m, 1H), 2.65-2.32 (m, 6H), 2.32-2.17 (m, 1H), 2.14 (s, 3H), 1.87-1.70 (m, 2H), 1.59 (s, 3H). 13C NMR (101 MHz, CDCl3) δ 155.30, 155.08, 141.94, 136.44, 135.97, 133.57, 131.19, 129.02, 128.21, 124.78, 121.34, 121.11, 109.90, 109.63, 59.01, 51.48, 50.65, 48.84, 29.52, 29.25, 17.89, 17.16, 15.48. C27H29N7OS, EIMS: m/z (M+H+): 500.6 (calculated), 500.4 (found).

1-{1-[(5-bromothiophen-2-yl)({1-[(1S)-1-phenylethyl]-1H-1,2,3,4-tetrazol-5-yl})methyl]piperidin-4-yl}-2,3-dihydro-1H-1,3-benzodiazol-2-one. (5bh). Yield: 70.1%. 1H NMR (400 MHz, CDCl3) δ 10.53 (s, 1H), 7.48-7.27 (m, 5H), 7.21-6.99 (m, 4H), 6.95 (d, J=3.8 Hz, 0.5H), 6.87 (d, J=3.8 Hz, 0.5H), 6.68 (d, J=3.8 Hz, 0.5H), 6.56 (d, J=3.8 Hz, 0.5H), 6.12 (q, J=7.0 Hz, 0.5H), 5.76 (q, J=7.0 Hz, 0.5H), 5.27 (s, 0.5H), 5.21 (s, 1H), 4.33-4.06 (m, 1H), 3.11-2.90 (m, 1H), 2.90-2.78 (m, 0.5H), 2.73-2.62 (m, 0.5H), 2.59-2.21 (m, 3H), 2.21-1.99 (m, 4H), 1.86-1.56 (m, 2H). 13C NMR (101 MHz, CDCl3) δ 155.33, 155.31, 152.84, 152.74, 139.43, 139.21, 137.96, 137.56, 129.43, 129.34, 129.30, 129.28, 129.12, 129.00, 128.97, 128.84, 128.82, 128.72, 128.26, 128.19, 126.69, 126.27, 121.42, 121.31, 121.06, 120.95, 114.13, 113.82, 110.01, 109.90, 109.51, 109.12, 60.01, 59.26, 58.83, 51.00, 50.51, 50.19, 49.04, 48.55, 29.47, 29.20, 29.04, 22.82, 22.70. C26H26BrN7OS, EI-MS: m/z (M+H+): 565.5 (calculated), 565.3 (found).

1-(1-{[5-(methylsulfanyl)thiophen-2-yl]({1-[(1S)-1-phenylethyl]-1H-1,2,3,4-tetrazol-5-yl})methyl}piperidin-4-yl)-2,3-dihydro-1H-1,3-benzodiazol-2-one. (5bi). Yield: 68.2%. 1H NMR (400 MHz, CDCl3) δ 10.31-10.06 (2S, 1H), 7.55-7.22 (m, 5H), 7.22-6.98 (m, 4H), 6.98-6.63 (m, 2H), 6.17 (q, J=7.0 Hz, 0.5H), 5.72 (q, J=7.0 Hz, 0.5H), 5.21 (2S, 1H), 4.32-4.05 (m, 1H), 3.14-2.85 (m, 1H), 2.85-2.69 (m, 1H), 2.60-1.99 (m, 10H), 1.91-1.53 (m, 2H). 13C NMR (101 MHz, CDCl3) δ 155.25, 153.29, 153.17, 139.63, 139.54, 139.33, 139.20, 138.03, 137.83, 129.91, 129.68, 129.50, 129.30, 129.27, 129.19, 129.09, 128.83, 128.80, 128.73, 128.22, 128.15, 126.74, 126.38, 126.32, 121.44, 121.33, 121.11, 121.04, 109.97, 109.86, 109.63, 109.24, 60.40, 59.53, 59.23, 58.81, 51.44, 50.59, 50.48, 49.25, 48.76, 29.54, 29.26, 29.16, 29.12, 22.85, 21.87, 21.72. C27H29N7OS2, EI-MS: m/z (M+H+): 532.7 (calculated), 532.7 (found).

1-{1-[(1-benzyl-1H-1,2,3,4-tetrazol-5-yl)(thiophen-2-yl)methyl]piperidin-4-yl}-2,3-dihydro-1H-1,3-benzodiazol-2- one. (5bj). Yield: 86.3%. 1H NMR (400 MHz, DMSO-d6) δ 10.79 (s, 1H), 7.66-7.51 (m, 1H), 7.49-7.21 (m, 5H), 7.14-6.86 (m, 6H), 6.01-5.71 (m, 3H), 4.08-3.87 (m, 1H), 3.19-3.01 (m, 1H), 2.99-2.80 (m, 1H), 2.43-2.20 (m, 2H), 2.20-2.01 (m, 2H), 1.72-1.44 (m, 2H). 13C NMR (101 MHz, DMSO-d6) δ 153.67, 153.61, 135.98, 134.81, 129.12, 128.75, 128.70, 128.22, 128.19, 127.80, 127.11, 126.30, 120.48, 120.24, 108.74, 108.51, 56.83, 50.27, 49.81, 47.61, 28.76, 28.50. C25H25N7OS, EI-MS: m/z (M+H+): 472.6 (calculated), 472.5 (found).

1-{1-[(R)-{1-[(1S)-1-phenylethyl]-1H-1,2,3,4-tetrazol-5-yl}(thiophen-3-yl)methyl]piperidin-4-yl}-2,3-dihydro-1H-1,3-benzodiazol-2-one. (5bk). Yield: 40.3%. The characterization of this compound was reported before (see, Zhang J, et al, Sci Rep 2018; 8(1):4653). 1-{1-[(S)-{1-[(1S)-1-phenylethyl]-1H-1,2,3,4-tetrazol-5-yl}(thiophen-3-yl)methyl]piperidin-4-yl}-2,3-dihydro-1H-1,3-benzodiazol-2-one. (5bl). Yield: 36.9%. The characterization of this compound was reported before (see, Zhang J, et al, Sci Rep 2018; 8(1):4653).

1-{1-[(1-cyclohexyl-1H-1,2,3,4-tetrazol-5-yl)(thiophen-3-yl)methyl]piperidin-4-yl}-2,3-dihydro-1H-1,3-benzodiazol-2-one. (5bm). Yield: 74.3%. The characterization of this compound was reported before (see, Zhang J, et al, Sci Rep 2018; 8(1):4653). 1-{1-[(1-benzyl-1H-1,2,3,4-tetrazol-5-yl)(phenyl)methyl]piperidin-4-yl}-2,3-dihydro-1H-1,3-benzodiazol-2-one. (5bn).

Yield: 80.5%. 1H NMR (400 MHz, DMSO-d6) δ 10.80 (s, 1H), 7.52-7.42 (m, 2H), 7.42-7.26 (m, 6H), 7.26-7.17 (m, 2H), 7.13-7.03 (m, 1H), 7.03-6.87 (m, 3H), 5.84 (d, J=3.3 Hz, 2H), 5.42 (s, 1H), 4.07-3.92 (m, 1H), 3.02-2.92 (m, 1H), 2.92-2.76 (m, 1H), 2.36-2.17 (m, 3H), 2.15-1.96 (m, 1H), 1.67-1.46 (m, 2H). 13C NMR (101 MHz, DMSO-d6) δ 154.39, 153.64, 134.69, 134.64, 129.20, 129.13, 128.72, 128.26, 128.23, 128.17, 127.72, 120.48, 120.29, 108.74, 108.60, 79.16, 61.98, 50.20, 49.93, 49.88, 49.01, 28.72, 28.56. C27H27N7O, EI-MS: m/z (M+H+): 466.6 (calculated), 466.6 (found).

1-{1-[(1-benzyl-1H-1,2,3,4-tetrazol-5-yl)(2-methylphenyl)methyl]piperidin-4-yl}-2,3-dihydro-1H-1,3-benzodiazol-2-one. (5bo). 1H NMR (400 MHz, CDCl3) δ 10.21 (s, 1H), 7.39-6.98 (m, 13H), 5.78-5.50 (m, 1H), 5.36-5.04 (m, 2H), 4.41-4.19 (m, 1H), 2.99-2.77 (m, 1H), 2.77-2.56 (m, 2H), 2.54-2.29 (m, 5H), 2.29-2.08 (m, 1H), 1.84-1.58 (m, 2H). 13C NMR (101 MHz, CDCl3) δ 155.25, 154.11, 137.74, 133.33, 131.57, 129.16, 128.93, 128.68, 128.21, 127.43, 126.26, 121.36, 121.06, 109.92, 109.43, 60.92, 51.31, 51.16, 50.95, 49.06, 29.49, 19.48.

C28H29N7O, EI-MS: m/z (M+H+): 480.6 (calculated), 480.6 (found).

1-{1-[phenyl({1-[(1S)-1-phenylethyl]-1H-1,2,3,4-tetrazol-5-yl})methyl]piperidin-4-yl}-2,3-dihydro-1H-1,3-benzodiazol-2-one. (5 bp). Yield: 71.3%. 1H NMR (400 MHz, CDCl3) δ 10.27 (s, 0.5H), 10.22 (s, 0.5H), 7.48-6.92 (m, 1H), 6.03 (q, J=7.0 Hz, 0.5H), 5.52 (q, J=7.0 Hz, 0.5H), 4.99 (s, 0.5H), 4.83 (s, 0.5H), 4.36-4.08 (m, 1H), 3.24-3.06 (m, 0.5H), 2.97-2.75 (m, 1H), 2.71-2.62 (m, 0.5H), 2.60-2.21 (m, 3H), 2.21-2.01 (m, 1H), 1.99-1.83 (m, 3H), 1.83-1.60 (m, 2H). 13C NMR (101 MHz, CDCl3) δ 155.32, 154.50, 154.06, 139.55, 139.17, 134.59, 134.34, 129.29, 129.21, 129.17, 129.09, 129.00, 128.97, 128.80, 128.74, 128.67, 128.22, 128.13, 126.60, 126.22, 121.44, 121.34, 121.11, 110.00, 109.87, 109.75, 109.40, 64.86, 64.74, 58.79, 58.60, 51.54, 50.85, 50.75, 50.66, 50.50, 50.16, 29.42, 29.24, 29.05, 22.67, 22.61. C28H29N7O, EI-MS: m/z (M+H+): 480.6 (calculated), 480.4 (found).

1-{1-[(2-methylphenyl)({1-[(1S)-1-phenylethyl]-1H-1,2,3,4-tetrazol-5-yl}))methyl]piperidin-4-yl}-2,3-dihydro-1H-1,3-benzodiazol-2-one. (5bq). Yield: 87.3%. 1H NMR (400 MHz, DMSO d6) δ 10.81 (2S, 1H), 7.45-7.29 (m, 1H), 7.29-7.09 (m, 8H), 7.09-6.85 (m, 4H), 6.19 (q, J=6.8 Hz, 0.5H), 5.91 (q, J=6.8 Hz, 0.5H), 5.53 (s, 0.5H), 5.41 (s, 0.5H), 4.19-3.97 (m, 1H), 3.16-2.99 (m, 0.5H), 2.74-1.99 (m, 8.5H), 1.79 (dd, J=6.9, 2.7 Hz, 3H), 1.72-1.43 (m, 2H). 13C NMR (101 MHz, DMSO-d6) δ 153.64, 153.61, 153.53, 153.28, 139.59, 139.26, 137.43, 137.13, 133.64, 133.61, 131.07, 130.84, 129.14, 129.12, 128.80, 128.62, 128.50, 128.41, 128.28, 128.24, 128.21, 128.14, 127.96, 127.86, 126.34, 126.17, 125.78, 125.58, 120.50, 120.47, 120.30, 108.77, 108.64, 108.52, 59.24, 59.18, 57.23, 50.39, 50.09, 50.02, 48.23, 48.03, 28.88, 28.70, 22.43, 22.08, 19.14, 18.98. C29H31N7O, EI-MS: m/z (M+H+): 494.6 (calculated), 494.6 (found).

1-[1-({1-[(1S)-1-phenylethyl]-1H-1,2,3,4-tetrazol-5-yl}(1,2,3-thiadiazol-4-yl)methyl)piperidin-4-yl]-2,3-dihydro-1H-1,3-benzodiazol-2-one. (5br). Yield: 72.6%. 1H NMR (400 MHz, CDCl3) δ 10.28 (s, 0.7H), 10.25 (s, 0.3H), 9.28 (s, 0.7H), 9.13 (s, 0.3H), 7.56-7.28 (m, 5H), 7.13-6.95 (m, 3.4H), 6.87-6.77 (m, 0.6H), 6.45 (q, J=7.0 Hz, 0.3H), 6.14 (s, 0.7H), 6.04 (q, J=7.0 Hz, 0.7H), 5.86 (s, 0.3H), 4.18-3.95 (m, 1H), 3.25-3.06 (m, 1H), 2.87-2.63 (m, 1H), 2.54-1.65 (m, 9H). 13C NMR (101 MHz, CDCl3) δ 155.23, 155.16, 152.43, 152.38, 139.55, 139.29, 137.99, 137.84, 129.41, 129.22, 129.16, 128.92, 128.76, 128.20, 128.12, 126.57, 126.38, 121.50, 121.39, 121.12, 120.92, 110.00, 109.90, 109.50, 108.97, 59.55, 58.92, 57.82, 56.98, 52.43, 52.06, 50.47, 50.31, 47.58, 46.80, 29.46, 29.39, 29.08, 28.67, 22.99, 22.78. C24H25N9OS, EI-MS: m/z (M+H+): 488.6 (calculated), 488.5 (found).

1-{1-[(2,1,3-benzoxadiazol-5-yl)({1-[(1S)-1-phenylethyl]-1H-1,2,3,4-tetrazol-5-yl})methyl]piperidin-4-yl}-2,3-dihydro-1H-1,3-benzodiazol-2-one. (5bs). Yield: 69.8%. 1H NMR (400 MHz, DMSO-d6) δ 10.80 (2S, 1H), 8.22-8.03 (m, 1H), 8.02-7.82 (m, 1H), 7.70-7.57 (m, 0.5H), 7.52-7.46 (m, 0.5H), 7.47-7.28 (m, 2.5H), 7.27-7.05 (m, 3H), 7.02-6.91 (m, 3.5H), 6.32 (qd, J=7.0, 1.8 Hz, 1H), 5.63 (2S, 1H), 4.22-4.04 (m, 0.5H), 4.03-3.83 (m, 0.5H), 3.17-3.03 (m, 0.5H), 2.98-2.79 (m, 1H), 2.79-2.66 (m, 0.5H), 2.50-2.31 (m, 2H), 2.31-2.16 (m, 1H), 2.16-1.80 (m, 4H), 1.73-1.32 (m, 2H). 13C NMR (101 MHz, DMSO-d6) δ 153.67, 153.57, 152.71, 152.67, 148.70, 148.49, 148.35, 148.27, 140.02, 139.89, 139.81, 139.53, 134.04, 133.25, 129.23, 129.03, 128.80, 128.62, 128.27, 128.20, 128.12, 127.95, 126.43, 126.18, 120.50, 120.33, 120.23, 116.11, 115.79, 115.54, 108.75, 108.60, 108.52, 61.48, 61.24, 57.34, 57.20, 49.84, 49.74, 49.63, 49.26, 48.94, 28.74, 28.49, 22.40, 22.10. C28H27N9O2, EIMS: m/z (M+H+): 522.6 (calculated), 522.6 (found).

1-{1-[(1-benzothiophen-2-yl)({1-[(1S)-1-phenylethyl]-1H-1,2,3,4-tetrazol-5-yl})methyl]piperidin-4-yl}-2,3-dihydro-1H-1,3-benzodiazol-2-one. (5bt). Yield: 72.3%. 1H NMR (400 MHz, CDCl3) δ 10.03 (2S, 1H), 7.54-7.22 (m, 7.5H), 7.22-7.00 (m, 5H), 7.00-6.85 (m, 1.5H), 6.22 (q, J=7.0 Hz, 0.5H), 5.67 (q, J=7.0 Hz, 0.5H), 5.31 (s, 0.5H), 5.27 (s, 0.5H), 4.33-4.10 (m, 1H), 3.14-3.00 (m, 0.5H), 3.00-2.88 (m, 0.5H), 2.88-2.71 (m, 1H), 2.64-2.31 (m, 2H), 2.31-2.12 (m, 1H), 2.12-1.98 (m, 3H), 1.90-1.54 (m, 3H). 13C NMR (101 MHz, CDCl3) δ 155.18, 153.73, 153.54, 139.59, 139.37, 136.35, 136.13, 129.32, 129.25, 129.13, 128.84, 128.81, 128.77, 128.50, 128.19, 128.11, 127.02, 126.84, 126.75, 126.67, 126.45, 126.34, 121.44, 121.33, 121.12, 121.07, 109.94, 109.82, 109.70, 109.28, 60.19, 59.25, 59.19, 58.78, 51.59, 50.63, 50.55, 49.35, 48.77, 29.56, 29.26, 29.15, 22.87, 22.80. C30H29N70S, EIMS: m/z (M+H+): 536.7 (calculated), 536.5 (found).

Example III

This example describes the materials and methods implemented during the experiments described in Examples I and II.

Animals.

Pathogen-free, adult male and female Sprague-Dawley rats (225-250 g; Envigo, Indianapolis, IN) were housed in temperature-controlled (23+3° C.) and light-controlled (12-h light/12-h dark cycle; lights on 07:00-19:00) rooms with standard rodent chow and water available ad libitum. The Institutional Animal Care and Use Committee of the College of Medicine at the University of Arizona approved all experiments. All procedures were conducted in accordance with the Guide for Care and Use of Laboratory Animals published by the National Institutes of Health and the ethical guidelines of the International Association for the Study of Pain. Animals were randomly assigned to treatment or control groups for the behavioral experiments. Animals were initially housed 3 per cage but individually housed after the intrathecal cannulation. All behavioral experiments were performed by experimenters who were blinded to the experimental groups and treatments.

Preparation of Acutely Dissociated Dorsal Root Ganglion Neurons

Dorsal root ganglia from all levels were acutely dissociated using methods as described previously [23]. Rat DRG neurons were isolated from 100 g female Sprague-Dawley rats using previously developed procedures [53]. In brief, removing dorsal skin and muscle and cutting the vertebral bone processes parallel to the dissection stage exposed the DRGs. DRGs were then collected, trimmed at their roots, and enzymatically digested in 3 mL bicarbonate-free, serum-free, sterile DMEM (Cat #11965, Thermo Fisher Scientific, Waltham, MA) solution containing neutral protease (3.125 mg.ml-1, Cat #LS02104; Worthington, Lakewood, NJ) and collagenase type 1 (5 mg/mL, Cat #LS004194, Worthington, Lakewood, NJ) and incubated for 60 minutes at 37° C. under gentle agitation. Dissociated DRG neurons (~1.5×10⁶) were then gently centrifuged to collect cells and washed with DRG media DMEM containing 1% penicillin/streptomycin sulfate from 10,000 μg/mL stock, 30 ng/mL nerve growth factor, and 10% fetal bovine serum before plating onto poly-D-lysine- and laminin-coated glass 12- or 15-mm coverslips.

Calcium Imaging in Acutely Dissociated Dorsal Root Ganglion Neurons

Dorsal root ganglion neurons were loaded for 30 minutes at 37° C. with 3 μM Fura-2AM (Cat #F1221, Thermo Fisher, stock solution prepared at 1 mM in DMSO, 0.02% pluronic acid, Cat #P-3000MP, Thermo Fisher) to follow changes in intracellular calcium([Ca2+]c) in a standard bath solution containing 139 mM NaCl, 3 mM KCl, 0.8 mM MgCl2, 1.8 mM CaCl₂), 10 mM Na HEPES, pH 7.4, 5 mM glucose exactly as previously described [7] Fluorescence imaging was performed with an inverted microscope, NikonEclipseTi-U (Nikon Instruments Inc., Melville, NY), using objective Nikon Fluor 4× and a Photometrics cooled CCD camera CoolSNAPES2 (Roper Scientific, Tucson, AZ) controlled by NIS Elements software (version 4.20, Nikon Instruments). The excitation light was delivered by a Lambda-LS system (Sutter Instruments, Novato, CA). The excitation filters (340±5 and 380±7) were controlled by a Lambda 10 to 2 optical filter change (Sutter Instruments). Fluorescence was recorded through a 505-nm dichroic mirror at 535±25 nm. To minimize photobleaching and phototoxicity, the images were taken every ~10 seconds during the time-course of the experiment using the minimal exposure time that provided acceptable image quality. The changes in [Ca2+]c were monitored by following a ratio of $F_{340}/F_{380}$, calculated after subtracting the background from both channels.

Dorsal Root Ganglia Neuron Transfection.

Collected cells were re-suspended in Nucleofector transfection reagent containing siRNA at 500 nM and 2 μg of the provided GFP plasmid as detailed previously [17]. Cells were then subjected to electroporation protocol 0-003 in an Amaxa Biosystem (Lonza, Basel, Switzerland) and plated onto poly-D-lysine—and laminin-coated glass 12-mm coverslips. Transfection efficiencies were routinely between 20% and 30% with ~10% cell death. Small diameter neurons were selected to target Aδ- and c-fiber nociceptive neurons. For rat DRG culture small cells were considered to be ~<30 μm as determined by an eyepiece micrometer within the objective lens. Successfully transfected cells were identified by GFP fluorescence. The siRNA sequences used were: UAGAUAGCAAAUACUUUGGCCGGGG (SEQ ID NO: 1) (for Cacnalg/CaV3.1; (Cat #RSS355855, Thermofisher)); CAGCCAUCUUCGUGGUGGAGAUGAU (SEQ ID NO: 2) (for Cacnalh/CaV3.2; (Cat #RSS350286, Thermofisher)); CAGCAUCCUUGGGAUGCAUAUCUUU (SEQ ID NO: 3) (for Cacnali/CaV3.3; Cat #RSS367566); and siRNA Negative Control, Med GC was used as a scrambled siRNA control (Cat #12935300). Cells were used 48 hrs after transfection.

Constellation Pharmacology.

These experiments were performed as described previously [53; 76], but with the following modifications. Dorsal root ganglia neurons were loaded at 37° C. with 3 μM Fura-2AM for 30 minutes in Tyrode solution (at ~310 mOsm) containing 119 mM NaCl, 2.5 mM KCl, 2 mM MgCl2, 2 mM CaCl₂), 25 mM HEPES, pH 7.4, and 30 mM glucose. After a 1-minute baseline measurement, Ca2+ influx was stimulated by the addition of the following receptor agonists: 400 nM menthol, 50 μM histamine, 10 μM adenosine triphosphate (ATP), 200 μM allyl isothiocyanate (AITC), 1 mM acetylcholine (Ach), and 100 nM capsaicin diluted in Tyrode solution. At the end of the constellation pharmacology protocol, cell viability was assessed by depolarization-induced Ca2+ influx using and an excitatory KCl solution comprising 32 mM NaCl, 90 mM KCl, 2 mM MgCl₂, 2 mM CaCl₂), 25 mM HEPES, pH 7.4, and 30 mM glucose. After the 1-minute baseline measurement, each trigger was applied for 15 seconds in the order indicated above in 6-minute intervals. After each trigger, bath solution was continuously perfused over the cells to wash off excess of the trigger. This process was automated using the Valve-Bank II perfusion system that controlled the perfusion of the standard bath solution and triggers (Automate Scientific, San Diego, CA). Except for the time course experiments, 5bk was incubated overnight onto DRGs. In all cases, 5bk was also added to the Tyrode solution during the loading with Fura-2AM. Fluorescence imaging was performed under the same conditions noted above for calcium imaging. A cell was defined as a "responder" if its fluorescence ratio of 340 nm/380 nm was greater than 10% of the baseline value calculated using the average fluorescence in the 30 seconds preceding application of the trigger.

Whole-Cell Patch Recordings of $Ca^{2+}$ and $Na^{2+}$ Currents in Acutely Dissociated DRG Neurons.

Recordings were obtained from acutely dissociated DRG neurons as described previously [34; 54]. To isolate calcium currents, $Na^+$ and $K^+$ currents were blocked with 500 nM tetrodotoxin (TTX; Alomone Laboratories) and 30 mM tetraethylammonium chloride (TEA-C1; Sigma). Extracellular recording solution (at ~310 mOsm) consisted of the following (in mM): 110 N-methyl-D-glucamine (NMDG), 10 $BaCl_2$, 30 TEA-C1, 10 HEPES, 10 glucose, pH at 7.4, 0.001 TTX, 0.01 nifedipine. The intracellular recording solution (at ~310 mOsm) consisted of the following (in mM): 150 $CsCl_2$, 10 HEPES, 5 Mg-ATP, 5 BAPTA, pH at 7.4. The protocol for isolating T-type calcium currents was previously described by Choe et al.[14] The extracellular recording solution used to isolate T currents consisted of the following (in millimolar): 2 $CaCl_2$), 152 TEA-Cl, 10 HEPES, pH adjusted to 7.4 with TEA-OH. The intracellular recording solution consisted of (in millimolar): 135 tetramethylammonium hydroxide, 10 EGTA, 40 HEPES, and 2 MgCl2, pH adjusted to 7.2 with hydrofluoric acid. Activation of $I_{C_a-T}$ was measured by using a holding voltage of –90 mV with voltage steps 200 ms in duration applied at 500-ms intervals in 10 mV increments from –70 to +60 mV. Inactivation of $I_{C_a-T}$ was determined by applying a 1500-ms conditioning prepulse (~110 to +20 mV in 10 mV increments) after which the voltage was stepped to –30 mV for 20 ms; a 40-ms interval with a holding voltage of –90 mV separated each acquisition. In the deactivation tau protocol, the neuron was first held at –110 mV, then the voltage jumped to –30 mV for 10 ms followed by a 50-ms conditioning prepulse (~160 to –40 mV in 10 mV increments). A 2-second interval with a holding voltage of –90 mV separated each acquisition. $I_{C_a-T}$ recovery from inactivation were obtained by using our standard double-pulse protocol with variable interpulse duration at –90 mV after a 500-ms-long inactivating pulse (Vh=–90 mV; Vt=–30 mV).

To isolate the contributions of the HVA calcium channel subtypes, we applied all but one of the following subunit-selective blockers (all purchased from Alomone Labs, Jerusalem): Nifedipine (10 µM, L-type); o-agatoxin GIVA (200 nM, P/Q-type) [52]; SNX-482 (200 nM, R-type) [56]; o-conotoxin GVIA (500 nM, N-type) [30] or TTA-P2 (1 µM, T-type)[14] to individually isolate the subtypes.

For recording sodium currents the internal solution consisted of (in mM): 140 CsF, 10 NaCl, 1.1Cs-EGTA, and 15 HEPES (pH 7.3, mOsm/L=290-310) and external solution contained (in mM): 140 NaCl, 30 tetraethylammonium chloride, 10 D-glucose, 3 KCl, 1 $CaCl_2$), 0.5 $CdCl_2$, 1 $MgCl_2$, and 10 HEPES (pH 7.3, mOsm/L=310-315). DRG neurons were interrogated with current-voltage (I-V) and activation/inactivation voltage protocols as previously described [17; 23]. The voltage protocols were as follows: (a) I-V protocol: from a –60 mV holding potential, cells were depolarized in 150-millisecond voltage steps from –70 to +60 mV (5-mV increments) which permitted acquisition of current density values such that we could analyze activation of sodium channels as a function of current vs voltage and infer peak current density (normalized to cell capacitance (in picofarads, pF)), which occurred between ~0 to 10 mV; (b) inactivation protocol: from a –60 mV holding potential, cells were subjected to hyperpolarizing/repolarizing pulses for 1 second between ~120 to 0 mV (+10 mV steps). This increment conditioned various proportions of channels into a state of fast-inactivation—in this case 0-mV test pulse for 200 milliseconds was able to reveal fast inactivation when normalized to maximum sodium current. Because of the differential inactivation kinetics of TTX-resistant and TTX-sensitive channels, the fast inactivation protocol allowed subtraction of electrically isolated TTX-R (current available after –40 mV prepulse) from total current (current available after –120 mV prepulse), as previously described [17]. Pipettes with 1 to 3 MΩ resistance were used for all recordings.

The Boltzmann relation was used to determine the voltage dependence for activation of $I_{Ca}$ and $I_{Na}$ wherein the conductance-voltage curve was fit by the equation $G/G_{max}=1/[1+\exp (V_{0.5}-V_m)/k]$, where G is the conductance $G=I/(V_m-E_{Ca}$ or $E_{Na})$, $G_{max}$ is the maximal conductance obtained from the Boltzmann fit under control conditions, $V_{0.5}$ is the voltage for half-maximal activation, $V_m$ is the membrane potential, and k is a slope factor. $E_{Ca}$ is the reversal potential for $I_{Ca}$; $E_{Na}$ is the reversal potential for $I_{Na}$ and was determined for each individual neuron. The values of $I_{Ca}$ and $I_{Na}$ around the reversal potential were fit with a linear regression line to establish the voltage at which the current was zero. The Boltzmann parameters were determined for each individual neuron and then used to calculate the mean±SEM.

Whole-cell recordings were obtained with a HEKA EPC-10 USB (HEKA Instruments Inc.); data were acquired with a Patchmaster (HEKA) and analyzed with a Fitmaster (HEKA). Capacitive artifacts were fully compensated, and series resistance was compensated by ~70%. Recordings made from cells with greater than a 5-mV shift in series resistance compensation error were excluded from analysis. All experiments were performed at room temperature (~23° C.). Pipettes with 1-3MΩ resistance were used for all recordings.

Calcitonin Gene-Related Peptide Release from Lumbar Slices.

Rats were deeply anesthetized with 5% isofluorane and then decapitated. Two vertebral incisions (cervical and lumbar) were made in order to expose the spinal cord. Pressure was applied to a saline-filled syringe inserted into the lumbar vertebral foramen, and the spinal cord was extracted. Only the lumbar region of the spinal cord was used for the CGRP release assay. Baseline treatments (#1 and #2) involved bathing the spinal cord in Tyrode's solution. The excitatory solution consisting of 90 mM KCl was paired with the treatment for fraction #4. These fractions (10 minutes, 400 µL each) were collected for measurement of CGRP release. Samples were immediately flash frozen and stored in a –20° C. freezer. 5bk (20 µM) or vehicle (0.9% saline) was added to the pretreatment and cotreatment fractions (#3 and 4). The concentration of CGRP released into the buffer was measured by enzyme-linked immunosorbant assay (Cat #589001, Cayman Chemical, Ann Arbor, MI).

Preparation of Spinal Cord Slices.

As described previously [90], young rats (postnatal 10-14 days) were deeply anesthetized with diethyl ether. For spinal nerve blocking, 0.3 mL of 2% lidocaine was injected to both sides of L4 to 5 lumbar vertebrae. Laminectomy was performed from mid-thoracic to low lumbar levels, and the spinal cord was quickly removed to cold modified artificial cerebrospinal fluid (aCSF) oxygenated with 95% 02 and 5% $CO_2$. The aCSF contained (in millimolar): 80 NaCl, 2.5 KCl, 1.25 $NaH_2PO_4$, 0.5 $CaCl_2$), 3.5 $MgCl_2$, 25 $NaHCO_3$, 75 sucrose, 1.3 ascorbate, 3.0 sodium pyruvate, with pH at 7.4 and osmolarity at 310 mOsm. Transverse 350-µm thick slices were obtained by a vibratome (VT1200S; Leica, Nussloch, Germany). Slices were then incubated for at least 1 hour at RT in an oxygenated recording solution containing (in millimolar): 125 NaCl, 2.5 KCl, 2 $CaCl_2$), 1 $MgCl_2$, 1.25 $NaH_2PO_4$, 26 $NaHCO_3$, 25 D-glucose, 1.3 ascorbate, 3.0 sodium pyruvate, with pH at 7.4 and osmolarity at 320 mOsm. The slices were then positioned in a recording chamber and continuously perfused with oxygenated recording solution at a rate of 3 to 4 mL/min before electrophysiological recordings at RT.

Electrophysiological Recording in Spinal Cord Slices by Whole-Cell Patch Clamp.

Substantia gelatinosa neurons were visualized and identified in the slices by means of infrared differential interference contrast video microscopy on an upright microscope (FN1; Nikon, Tokyo, Japan) equipped with a 3 40/0.80 water-immersion objective and a charge-coupled device camera. Patch pipettes with resistance at 6 to 10 MΩ were made from borosilicate glass (Sutter Instruments, Novato, CA) on a 4-steps micropipette puller (P-90; Sutter Instruments, Novato, CA). The pipette solution contained the following (in millimolar): 120 potassium gluconate, 20 KCl, 2 MgCl 2, 2 Na 2-ATP, 0.5 Na-GTP, 20 HEPES, 0.5 EGTA, with pH at 7.28 and osmolarity at 310 mOsm. The membrane potential was held at −60 mV using PATCHMASTER software in combination with a patch clamp amplifier (EPC10; HEKA Elektronik, Lambrecht, Germany).

The whole-cell configuration was obtained in voltage-clamp mode. To record spontaneous excitatory postsynaptic currents (sEPSCs), bicuculline methiodide (10 m M) and strychnine (1 m M) were added to the recording solution to block γ-aminobutyric acid-activated and glycine-activated currents. Hyperpolarizing step pulses (5 mV in intensity, 50 milliseconds in duration) were periodically delivered to monitor the access resistance (15-25 MΩ), and recordings were discontinued if the access resistance changed by more than 20%. For each neuron, sEPSCs were recorded for a total duration of 2 minutes. Currents were filtered at 3 kHz and digitized at 5 kHz. Data were further analyzed by the Mini-Analysis (Synatosoft Inc, NJ) and Clampfit 10.7 Program. The amplitude and frequency of sEPSCs were compared between neurons from animals in control and 5bk groups.

Implantation of Intrathecal Catheter.

For intrathecal (i.t.) drug administration, rats were chronically implanted with catheters as described by Yaksh and Rudy [89]. Rats were anesthetized with ketamine/xylazine and placed in a stereotactic head holder. The occipital muscles were separated from their occipital insertion and retracted caudally to expose the cisternal membrane at the base of the skull. Polyethylene tubing was passed caudally from the cisterna magna to the level of the lumbar enlargement. Animals were allowed to recover and were examined for evidence of neurologic injury. Animals with evidence of neuromuscular deficits were excluded.

Testing of Allodynia.

The assessment of tactile allodynia (i.e., a decreased threshold to paw withdrawal after probing with normally innocuous mechanical stimuli) consisted of testing the withdrawal threshold of the paw in response to probing with a series of calibrated fine (von Frey) filaments. Each filament was applied perpendicularly to the plantar surface of the paw of rats held in suspended wire mesh cages. Withdrawal threshold was determined by sequentially increasing and decreasing the stimulus strength (the "up and down" method), and data were analyzed with the nonparametric method of Dixon, as described by Chaplan et al [11] and expressed as the mean withdrawal threshold.

HIV Sensory Neuropathy (HIV SN).

Mechanical allodynia was produced by intrathecal administration of the human immunodeficiency virus-1 (HIV-1) envelope glycoprotein, GP120 [51]. Seven days after implantation of an intrathecal catheter, baseline behavioral measurements were obtained and then rats were randomly assigned to two groups. On days 10, 12 and 14, rats were injected i.t. with 300 ng of GP120 (Cat #4961, HIV-1 BaL gp120 recombinant protein, NIH-AIDS Reagent program) in a final volume of 20 μl in 0.9% saline and 0.1% BSA. Rats were tested on day 35 (i.e., 21 days after the last i.t. injection of GP120).

Paclitaxel-Induced Neuropathy Model.

Rats were given paclitaxel (Cat #P-925-1, Goldbio, Olivette, MO) based on the protocol described by Polomano et al. [60]. In brief, pharmaceutical-grade paclitaxel (Taxol) was resuspended at a concentration of 2 mg/ml in 30% 1:1 Cremophor EL: ethanol, 70% Saline and given to the rats at 2 mg/kg intraperitoneally (i.p.) every other day for a total of 4 injections (days 0, 2, 4, and 6), resulting in a final cumulative dose of 8 mg/kg. No abnormal spontaneous behavioral changes in the rats were noted during or after the treatment. Animals developed mechanical hyperalgesia within 10 days after the first paclitaxel injection.

Elevated Plus Maze (EPM).

The EPM consists of four elevated (50 cm) arms (50 cm long and 10 cm wide) with two opposing arms containing 30 cm high opaque walls. EPM testing occurred in a quiet testing room with ambient lighting at ~500 lux. On day of testing, rats were allowed to acclimate to the testing room for 20 minutes. Each rat was placed in a closed arm, facing the enter platform and cage mates started in the same closed arm. Each rat was allowed 5 minutes to explore the EPM and then returned to its home cage. Between animals the EPM was cleaned thoroughly with Versa-Clean (Fisher Scientific) . EPM performance was recorded using an overhead video camera (MHD Sport 2.0 WiFi Action Camera, Walmart-.com) for later quantification. Open and closed arm entries were defined as the front two paws entering the arm, and open arm time began the moment the front paws entered the open arm and ended upon exit. An anxiety index was also calculated; the index combines EPM parameters into one unified ratio with values ranging from 0 to 1, with a higher value indicating increased anxiety [33]. The following equation was used for calculation of the anxiety index: Anxiety Index=1−(open arm time/5 mn)+(open arm entry/total entry)

Spinal Nerve Ligation (SNL).

Nerve ligation, performed as described earlier [40; 53], produces signs of neuropathic dysesthesias, including tactile allodynia and thermal hypersensitivity. All nerve operations occurred 5 days after intrathecal catheter implantation. Rats were anesthetized with 2% isoflurane in 02 anesthesia delivered at 2 L/min. The skin over the caudal lumbar region was incised and the muscles retracted. The L5 and L6 spinal nerves were exposed, carefully isolated, and tightly ligated with 4-0 silk distal to the dorsal root ganglion without limiting the use of the left hind paw of the animal. All animals were allowed 7 days to recover before any behavioral testing. Any animals exhibiting signs of motor deficiency were euthanized.

Rotarod.

Rats were trained to walk on a rotating rod (10 rev/min; Rotamex 4/8 device) with a maximal cutoff time of 180 seconds. Training was initiated by placing the rats on a rotating rod and allowing them to walk until either falling off, or maximal cutoff time was reached. This process was repeated 6 times and the rats were allowed to recover for 24 hours before intrathecal compound administration. Prior to treatment, the rats were run once on a moving rod in order to establish a baseline value. Assessment consisted of placing the rats on the moving rod and timing until either they fell off or reached a maximum of 180 seconds.

Competition Radioligand Binding

Details on our cell lines, culture methods, and binding methods have been reported previously [59]. All cells were Chinese Hamster Ovary (CHO-KI) cells overexpressing human opioid receptor (mu [MOR], delta [DOR], or kappa [KOR]). Cell pellets for binding were prepared by growing cells to confluency in 15 cm dishes, 3 per pellet. The cells were collected using 5 mM EDTA in dPBS (no trypsin) and stored at −80° C. until the assay was performed. The assay was performed by incubating 18.5-25 µg of membrane protein with 0.97-4.76 nM of $^3$H-diprenorphine (PerkinElmer) and concentration curves of 5bk or positive control (naloxone for MOR and DOR, U50,488 for KOR) in a 200 µL volume for 1 hour at room temperature. Reactions were harvested using a 96 well format Brandel Cell Harvester, and data acquired using a PerkinElmer MicroBeta2 6-detector 96-well format scintillation counter. The data was normalized to binding in the presence of Vehicle (100%; 0.1% DMSO and 0.1% BSA) and non-specific binding (0%; 10 µM naloxone) and reported as the mean±SEM. Curves were fit using a 1-site binding 3-variable nonlinear regression model with GraphPad Prism 8.3, using the previously-measured $K_D$ values of $^3$H-diprenorphine in these cells [59]. The data output was reported as the mean Ki ±SEM of N=3 independent experiments.

Statistical Analysis.

All data was first tested for a Gaussian distribution using a D'Agostino-Pearson test (Prism 8 Software, Graphpad, San Diego, CA). SNI- (day 15 post-surgery), GP120- (day 15 post last injection) and paclitaxel- (day 15 post-injection) induced allodynia was quantified as percentage of maximum possible allodynia using the formula: percentage allodynia= [(baseline threshold—post-injury threshold)/baseline threshold]×100. Reversal of allodynia by drugs (that is, anti-allodynia) was quantified with respect to the area under the threshold-time curve (using the trapezoidal method) over the post-injection testing period. Data are reported as percentage of the maximum possible anti-allodynia, calculated for each rat as a ratio of its actual anti-allodynia compared to a hypothetical situation in which the drug brought withdrawal thresholds to their original baseline at all post-injection time points. The statistical significance of differences between means was determined by a parametric ANOVA followed by Tukey's post hoc or a non-parametric Kruskal Wallis test followed by Dunn's post-hoc test depending on if datasets achieved normality. Behavioral data with a time course were analyzed by Two-way ANOVA with Sidak's post hoc test. Differences were considered significant if p<0.05. Error bars in the graphs represent mean±SEM. See statistical analysis described in Table 1. All data were plotted in Prism 8. No outlier data were removed.

TABLE 1

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| FIG. 3A | Calcium imaging - screening with a 40 mM KCl challenge | One-way ANOVA p < 0.0001 | Dunnett's multiple comparisons test | DMSO 0.01% | |
| | | | DMSO 0.01% vs. 5aa < 0.0001 | n = 1032 | |
| | | | DMSO 0.01% vs. 5ab < 0.0001 | 5aa n = 378 | |
| | | | DMSO 0.01% vs. 5ac 0.9988 | 5ab n = 995 | |
| | | | DMSO 0.01% vs. 5ad 0.0023 | 5ac n = 471 | |
| | | | DMSO 0.01% vs. 5ae < 0.0001 | 5ad n = 200 | |
| | | | DMSO 0.01% vs. 5af < 0.0001 | 5ae n = 554 | |
| | | | DMSO 0.01% vs. 5ag < 0.0001 | 5af n = 244 | |
| | | | DMSO 0.01% vs. 5ah < 0.0001 | 5ag n = 242 | |
| | | | DMSO 0.01% vs. 5ai < 0.0001 | 5ah n = 275 | |
| | | | DMSO 0.01% vs. 5aj 0.9998 | 5ai n = 542 | |
| | | | DMSO 0.01% vs. 5ak 0.014 | 5aj n = 409 | |
| | | | DMSO 0.01% vs. 5al 0.5522 | 5ak n = 214 | |
| | | | DMSO 0.01% vs. 5am < 0.0001 | 5al n = 590 | |
| | | | DMSO 0.01% vs. 5an 0.0012 | 5am n = 216 | |
| | | | DMSO 0.01% vs. 5ao < 0.0001 | 5an n = 437 | |
| | | | DMSO 0.01% vs. 5ap < 0.0001 | 5ao n = 567 | |
| | | | DMSO 0.01% vs. 5aq < 0.0001 | 5ap n = 222 | |
| | | | DMSO 0.01% vs. 5ar < 0.0001 | 5aq n = 683 | |
| | | | DMSO 0.01% vs. 5as < 0.0001 | 5ar n = 455 | |
| | | | DMSO 0.01% vs. 5at < 0.0001 | 5as n = 357 | |
| | | | DMSO 0.01% vs. 5au < 0.0001 | 5at n = 934 | |
| | | | DMSO 0.01% vs. 5av < 0.0001 | 5au n = 885 | |
| | | | DMSO 0.01% vs. 5aw < 0.0001 | 5av n = 534 | |
| | | | DMSO 0.01% vs. 5ax < 0.0001 | 5aw n = 264 | |
| | | | DMSO 0.01% vs. 5ay < 0.0001 | 5ax n = 597 | |
| | | | DMSO 0.01% vs. 5az 0.9264 | 5ay n = 852 | |
| | | | DMSO 0.01% vs. 5ba < 0.0001 | 5az n = 1132 | |
| | | | DMSO 0.01% vs. 5bb < 0.0001 | 5ba n = 802 | |
| | | | DMSO 0.01% vs. 5bc < 0.0001 | 5bb n = 567 | |
| | | | DMSO 0.01% vs. 5bd < 0.0001 | 5bc n = 530 | |
| | | | DMSO 0.01% vs. 5be 0.9987 | 5bd n = 751 | |
| | | | DMSO 0.01% vs. 5bf 0.9988 | 5be n = 348 | |
| | | | DMSO 0.01% vs. 5bg < 0.0001 | 5bf n = 284 | |
| | | | DMSO 0.01% vs. 5bh < 0.0001 | 5bg n = 747 | |
| | | | DMSO 0.01% vs. 5bi < 0.0001 | 5bh n = 802 | |
| | | | DMSO 0.01% vs. 5bj 0.767 | 5bi n = 644 | |
| | | | DMSO 0.01% vs. 5bk < 0.0001 | 5bj n = 95 | |
| | | | DMSO 0.01% vs. 5bl < 0.0001 | 5bk n = 78 | |
| | | | DMSO 0.01% vs. 5bm < 0.0001 | 5bl n = 958 | |
| | | | DMSO 0.01% vs. 5bn 0.9994 | 5bm n = 381 | |

TABLE 1-continued

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| | | | DMSO 0.01% vs. 5bo < 0.0001 | 5bn n = 100 | |
| | | | DMSO 0.01% vs. 5bp < 0.0001 | 5bo n = 559 | |
| | | | DMSO 0.01% vs. 5bq < 0.0001 | 5bp n = 604 | |
| | | | DMSO 0.01% vs. 5br < 0.0001 | 5bq n = 681 | |
| | | | DMSO 0.01% vs. 5bs < 0.0001 | 5br n = 543 | |
| | | | DMSO 0.01% vs. 5bt < 0.0001 | 5bs n = 1250 | |
| | | | | 5bt n = 914 | |
| FIG. 3B | Calcium imaging - screening with a 90 mM KCl challenge | One-way ANOVA p < 0.0001 | Dunnett's multiple comparisons test | DMSO 0.01% n = 1032 | |
| | | | DMSO 0.01% vs. 5aa < 0.0001 | 5aa n = 378 | |
| | | | DMSO 0.01% vs. 5ab < 0.0001 | 5ab n = 995 | |
| | | | DMSO 0.01% vs. 5ac < 0.0001 | 5ac n = 471 | |
| | | | DMSO 0.01% vs. 5ad < 0.0001 | 5ad n = 200 | |
| | | | DMSO 0.01% vs. 5ae < 0.0001 | 5ae n = 554 | |
| | | | DMSO 0.01% vs. 5af < 0.0001 | 5af n = 244 | |
| | | | DMSO 0.01% vs. 5ag < 0.0001 | 5ag n = 242 | |
| | | | DMSO 0.01% vs. 5ah 0.3379 | 5ah n = 275 | |
| | | | DMSO 0.01% vs. 5ai < 0.0001 | 5ai n = 542 | |
| | | | DMSO 0.01% vs. 5aj < 0.0001 | 5aj n = 409 | |
| | | | DMSO 0.01% vs. 5ak < 0.0001 | 5ak n = 214 | |
| | | | DMSO 0.01% vs. 5al < 0.0001 | 5al n = 590 | |
| | | | DMSO 0.01% vs. 5am 0.0086 | 5am n = 216 | |
| | | | DMSO 0.01% vs. 5an 0.0086 | 5an n = 437 | |
| | | | DMSO 0.01% vs. 5ao < 0.0001 | 5ao n = 567 | |
| | | | DMSO 0.01% vs. 5ap 0.9803 | 5ap n = 222 | |
| | | | DMSO 0.01% vs. 5aq 0.7626 | 5aq n = 683 | |
| | | | DMSO 0.01% vs. 5ar 0.3921 | 5ar n = 455 | |
| | | | DMSO 0.01% vs. 5as 0.9997 | 5as n = 357 | |
| | | | DMSO 0.01% vs. 5at < 0.0001 | 5at n = 934 | |
| | | | DMSO 0.01% vs. 5au 0.9984 | 5au n = 885 | |
| | | | DMSO 0.01% vs. 5av < 0.0001 | 5av n = 534 | |
| | | | DMSO 0.01% vs. 5aw < 0.0001 | 5aw n = 264 | |
| | | | DMSO 0.01% vs. 5ax < 0.0001 | 5ax n = 597 | |
| | | | DMSO 0.01% vs. 5ay < 0.0001 | 5ay n = 852 | |
| | | | DMSO 0.01% vs. 5az < 0.0001 | 5az n = 1132 | |
| | | | DMSO 0.01% vs. 5ba < 0.0001 | 5ba n = 802 | |
| | | | DMSO 0.01% vs. 5bb 0.0046 | 5bb n = 567 | |
| | | | DMSO 0.01% vs. 5bc 0.285 | 5bc n = 530 | |
| | | | DMSO 0.01% vs. 5bd < 0.0001 | 5bd n = 751 | |
| | | | DMSO 0.01% vs. 5be 0.9988 | 5be n = 348 | |
| | | | DMSO 0.01% vs. 5bf 0.0577 | 5bf n = 284 | |
| | | | DMSO 0.01% vs. 5bg < 0.0001 | 5bg n = 747 | |
| | | | DMSO 0.01% vs. 5bh < 0.0001 | 5bh n = 802 | |
| | | | DMSO 0.01% vs. 5bi < 0.0001 | 5bi n = 644 | |
| | | | DMSO 0.01% vs. 5bj 0.0564 | 5bj n = 95 | |
| | | | DMSO 0.01% vs. 5bk < 0.0001 | 5bk n = 78 | |
| | | | DMSO 0.01% vs. 5bl < 0.0001 | 5bl n = 958 | |
| | | | DMSO 0.01% vs. 5bm < 0.0001 | 5bm n = 381 | |
| | | | DMSO 0.01% vs. 5bn 0.0007 | 5bn n = 100 | |
| | | | DMSO 0.01% vs. 5bo < 0.0001 | 5bo n = 559 | |
| | | | DMSO 0.01% vs. 5bp < 0.0001 | 5bp n = 604 | |
| | | | DMSO 0.01% vs. 5bq < 0.0001 | 5bq n = 681 | |
| | | | DMSO 0.01% vs. 5br < 0.0001 | 5br n = 543 | |
| | | | DMSO 0.01% vs. 5bs < 0.0001 | 5bs n = 1250 | |
| | | | DMSO 0.01% vs. 5bt < 0.0001 | 5bt n = 914 | |
| FIG. 3D | Calcium imaging - time course of effect of 5bk | One-way ANOVA p < 0.0001 | Dunnett's multiple comparisons test DMSO 0.01% vs. Acute p = 0.1863 DMSO 0.01% vs. 30 min p = 0.0043 DMSO 0.01% vs. 3 hr p < 0.0001 DMSO 0.01% vs. overnight p < 0.0001 | DMSO 0.01% n = 87 Acute 5bk n = 108 30 min 5bk n = 81 3 hr 5bk n = 75 overnight 5 bk n = 128 | |
| FIG. 3E | Calcium imaging - concentration response of 5bk | Non-linear regression | [Iinhibitor] vs. response (three parameters) IC50 = 4.195 μM; $r^2$ = 0.4137 | | |
| FIG. 5C | Whole cell patch clamp electrophysiology - Peak T type currents | | Unpaired t-test DMSO 0.01% vs. 5bk 20 μM p = 0.2343 ($V_{0.5}$) and p = 0.1009 (k) | DMSO 0.01% n = 16 5bk n = 16 | |

TABLE 1-continued

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| FIG. 5D | Whole cell patch clamp electrophysiology Voltage-dependence of half-activation ($V_{0.5}$) and slope (k) | Non-parametric test | Mann-Whitney test $V_{0.5}$: DMSO 0.01% vs. 5bk 20 μM p = 0.0019 | DMSO 0.01% n = 16 5bk n = 16 | |
| FIG. 5F | Whole cell patch clamp electrophysiology $\tau_{inactivation}$ | | Mann-Whitney test DMSO 0.01% vs. 5bk 20 μM p = 0.9591 | DMSO 0.01% n = 8 5bk n = 8 | |
| FIG. 5H | Whole cell patch clamp electrophysiology - 0-90% rise time at −40 mV | | Mann-Whitney test DMSO 0.01% vs. 5bk 20 μM p = 0.3292 | DMSO 0.01% n = 17 5bk n = 19 | |
| FIG. 5I | Whole cell patch clamp electrophysiology - Voltage-dependence of half-inactivation ($V_{0.5}$) and slope (k) | | Unpaired t-test DMSO 0.01% vs. 5bk 20 μM p = 0.7833 ($V_{0.5}$) and p = 0.0575 (k) | DMSO 0.01% n = 15 5bk n = 16 | |
| FIG. 6D | Whole cell patch clamp electrophysiology - Peak L type currents | | Mann-Whitney test DMSO 0.01% vs. 5bk 20 μM p = 0.4470 | DMSO 0.01% n = 10 5bk n = 9 | |
| FIG. 6E | Whole cell patch clamp electrophysiology Voltage-dependence of half-activation and inactivation ($V_{0.5}$) and slopes (k) of L-type currents | | Mann-Whitney test DMSO 0.01% vs. 5bk 20 μM p = 0.2222 (for Activation $V_{0.5}$) DMSO 0.01% vs. 5bk 20 uM p = 0.9318 (for Activation k) DMSO 0.01% vs. 5bk 20 μM p = 0.2222 (for Inactivation $V_{0.5}$) DMSO 0.01% vs. 5bk 20 μM p = 0.4862 (for Inactivation k) | DMSO 0.01% n = 10 5bk n = 9 | |
| FIG. 6I | Whole cell patch clamp electrophysiology - Peak P/Q type currents | | Mann-Whitney test DMSO 0.01% vs. 5bk 20 μM p = 0.8992 | DMSO 0.01% n = 12 5bk n = 12 | |
| FIG. 6J | Whole cell patch clamp electrophysiology - Voltage-dependence of half-activation and inactivation ($V_{0.5}$) and slopes (k) of P/Q-type currents | | Mann-Whitney test DMSO 0.01% vs. 5bk 20 μM p = 0.2496 (for Activation $V_{0.5}$) DMSO 0.01% vs. 5bk 20 μM p = 0.0694 (for Activation k) DMSO 0.01% vs. 5bk 20 μM p = 0.2017 (for Inactivation $V_{0.5}$) DMSO 0.01% vs. 5bk 20 μM p = 0.3637 (for Inactivation k) | DMSO 0.01% n = 10 5bk n = 8 | |
| FIG. 6N | Whole cell patch clamp electrophysiology - Peak N type currents | | Mann-Whitney test DMSO 0.01% vs. 5bk 20 μM p = 0.2575 | DMSO 0.01% n = 14 5bk n = 12 | |
| FIG. 6O | Whole cell patch clamp electrophysiology - Voltage-dependence of half-activation and inactivation ($V_{0.5}$) and slopes (k) of N-type currents | | Mann-Whitney test DMSO 0.01% vs. 5bk 20 μM p = 0.5003 (for Activation $V_{0.5}$) DMSO 0.01% vs. 5bk 20 μM p = 0.8481 (for Activation k) DMSO 0.01% vs. 5bk 20 μM p = 0.0930 (for Inactivation $V_{0.5}$) DMSO 0.01% vs. 5bk 20 μM p = 0.2784 (for Inactivation k) | DMSO 0.01% n = 12 5bk n = 17 | |
| FIG. 6S | Whole cell patch clamp electrophysiology - Peak R type currents | | Mann-Whitney test DMSO 0.01% vs. 5bk 20 μM p = 0.6830 | DMSO 0.01% n = 14 5bk n = 15 | |
| FIG. 6T | Whole cell patch clamp electrophysiology - Voltage-dependence of half-activation and inactivation ($V_{0.5}$) and slopes (k) of R type currents | | Mann-Whitney test DMSO 0.01% vs. 5bk 20 μM p = 0.7532 (for Activation $V_{0.5}$) DMSO 0.01% vs. 5bk 20 μM p = 0.5951 (for Activation k) DMSO 0.01% vs. 5bk 20 μM p = 0.9038 (for Inactivation $V_{0.5}$) DMSO 0.01% vs. 5bk 20 μM p = 0.8727 (for Inactivation k) | DMSO 0.01% n = 14 5bk n = 15 | |

TABLE 1-continued

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| FIG. 9 | Calcium imaging | Non-parametric test | Mann-Whitney test<br>Scramble DMSO vs. Scramble 5bk<br>p = 0.0132<br>siRNA CaV3.1 DMSO vs. siRNA CaV3.1 5bk p = 0.0040<br>siRNA CaV3.2 DMSO vs. siRNA CaV3.2 5bk p = 0.6277<br>siRNA CaV3.3 DMSO vs. siRNA CaV3.3 5bk p = 0.0469 | Scramble DMSO n = 42<br>Scramble 5bk n = 17<br>siRNA CaV3.1 DMSO n = 19<br>siRNA CaV3.1 5bk n = 13<br>siRNA CaV3.2 DMSO n = 10<br>siRNA CaV3.2 5bk n =12<br>siRNA CaV3.3 DMSO n = 24<br>siRNA CaV3.3 5bk n = 17 | |
| FIG. 10C | Constellation pharmacology - # of functional classes | z-test | DMSO 0.01% vs. 5bk 20 μM<br>P = 0.00288 | | |
| FIG. 10D | Constellation pharmacology - % responders | z-test | DMSO 0.01% vs. 5bk 20 μM<br>1 response: p = 0.02144<br>2 response: p = 0.63122<br>3 response: p = 0.48392<br>4 response: p = 0.65994<br>5 response: p = 0.60306<br>6 response: p = 0.98404 | DMSO 0.01% n =2002 cells<br>5bk 20 μM n = 2902 cells | |
| FIG. 10E | Constellation pharmacology - % responders | z-test | DMSO 0.01% vs. 5bk 20 μM<br>AITC: p = 0.41222<br>Acetylcholine: p = 0.23404<br>ATP: p < 0.00001<br>Histamine: p = 0.77948<br>Menthol: p = 0.10524<br>Capsaicin: p < 0.00001 | DMSO 0.01% n = 2002 cells<br>5bk 20 μM n = 2902 cells | |
| FIG. 10F | Constellation pharmacology - average peak response | z-test | DMSO 0.01% vs. 5bk 20 μM<br>ACh/ATP: p = 0.5552<br>ACh/Cap: p = 0.90448<br>ATP/Menthol: p = 0.79486<br>Menthol/Cap: p = 0.98404<br>AITC/ATP/Cap: p = 0.86502<br>ACh/ATP/Cap: p = 0.80258<br>ATP/Menthol/Cap: p = 0.84148<br>AITC/ATP/Menthol/Cap: p = 0.8807 | DMSO 0.01% n = 2002 cells<br>5bk 20 μM n = 2902 cells | |
| FIG. 10G | P Constellation pharmacology - Peak response to trigger | Mann-Whitney | DMSO 0.01% vs. 5bk 20 μM<br>AITC: p = 0.017<br>Acetylcholine: p = 0.0035<br>ATP: p < 0.0001<br>Histamine: p = 0.6790<br>Menthol: p < 0.0001<br>Capsaicin: p < 0.0001<br>KCl: p < 0.0001 | DMSO 0.01% n = 2002 cells<br>5bk 20 μM n = 2902 cells | |
| FIG. 10H | Constellation pharmacology - area under the curve | Mann-Whitney | DMSO 0.01% vs. 5bk 20 μM<br>AITC: p < 0.0001<br>Acetylcholine: p = 0.0002<br>ATP: p = 0.0434<br>Histamine: p = 0.0131<br>Menthol: p = 0.0001<br>Capsaicin: p = 0.9615 | DMSO 0.01% n = 2002 cells<br>5bk 20 μM n = 2902 cells | |
| FIG. 10I | Constellation pharmacology - Average Peak KCl response | Mann-Whitney | DMSO 0.01% vs. 5bk 20 μM<br>AITC: p = 0.2493<br>Acetylcholine: p < 0.0001<br>ATP: p < 0.0001<br>Histamine: p = 0.3729<br>Menthol: p < 0.0001<br>Capsaicin: p< 0.0001<br>KCl: p < 0.0001 | DMSO 0.01% n = 2002 cells<br>5bk 20 μM n = 2902 cells | |
| FIG. 13A-C | Competition Binding Assay for Mu, Delta, and Kappa opioid receptors | 3 variable, 1 site binding non-linear regression curve-fit | 5bk was reported as "Not Converged" for all 3 panels, meaning no measurable competition. Mathematically, this is defined as no fitted curve with an $R^2 > 0.6$. | Results in measure of affinity reported as mean Ki ± SEM of the N = 3 set. | |

TABLE 1-continued

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| FIG. 14B | Slice electrophysiology - Amplitude of EPSCs | Mann-Whitney p = 0.4332 | | Control (DMSO 0.01%): n = 17 5bk (20 μM): n = 17 | Control (DMSO 0.01%): n = 1 5bk (20 μM): n = 1 |
| FIG. 14C | Slice electrophysiology - Frequency of EPSCs | Mann-Whitney p < 0.0001 | | Control (DMSO 0.01%): n = 17 5bk (20 μM): n = 18 | |
| FIG. 15 | CGRP release from spinal cords | Two-way ANOVA | Dunnett's multiple comparisons test Baseline 1: DMSO 0.01% vs. 5bk 20 μM p =0.9998 Baseline 2: DMSO 0.01% vs. 5bk 20 μM p = 0.9935 Treatment: DMSO 0.01% vs. 5bk 20 μM p = 0.9994 Treatment plus 90 mM KCl: DMSO 0.01% vs. 5bk 20 μM p = 0.0002 Wash: DMSO 0.01% vs. 5bk 20 μM p = 0.8947 | DMSO 0.01% n = 4 5bk n = 4 for all conditions | |
| FIG. 16A | Spared nerve injury - paw withdrawal threshold | Two-way ANOVA | Sidak's post hoc test Vehicle vs. 5 bk: Pre: p > 0.9999    0 min: p > 0.9999    30 min: p > 0.9999    60 min: p > 0.9999   120 min: p = 0.0150   180 min: p = 0.0162   240 min: p = 0.0828   300 min: p = 0.9074 | Vehicle n = 6 5bk n = 6 for all conditions | |
| FIG. 16B | Spared nerve injury - % anti-allodynia | Two-way ANOVA | Sidak's post hoc test Vehicle vs. 5 bk:    30 min: p > 0.9999    60 min: p > 0.9999   120 min: p = 0.0344   180 min: p = 0.0341   240 min: p = 0.1245   300 min: p = 0.8773 | Vehicle n = 6 5bk n = 6 for all conditions | |
| FIG. 16C | Spared nerve injury - Area under the curve | | Mann Whitney test Vehicle vs. 5 bk p = 0.0411 | Vehicle n = 6 5bk n = 6 for all conditions | |
| FIG. 16D | GP120 - paw withdrawal threshold | Two-way ANOVA | Sidak's multiple comparisons post hoc test Vehicle vs. 5 bk: Pre: p > 0.9999    0 min: p > 0.9999    30 min: p = 0.9998    60 min: p = 0.0022   120 min: p = 0.0002   180 min: p = 0.0208   240 min: p = 0.7186   300 min: p = 0.6802 | Vehicle n = 6 5bk n = 6 for all conditions | |
| FIG. 16E | GP120 - % anti-allodynia | Two-way ANOVA | Sidak's multiple comparisons post hoc test Vehicle vs. 5 bk:    30 min: p = 0.9908    60 min: p = 0.0060   120 min: p = 0.0015   180 min: p = 0.0422   240 min: p = 0.9751   300 min: p = 0.8785 | Vehicle n = 6 5bk n = 6 for all conditions | |
| FIG. 16F | GP120 - Area under the curve | | Mann Whitney test Vehicle vs. 5 bk p = 0.0152 | Vehicle n = 6 5bk n = 6 for all conditions | |
| FIG. 16G | Paclitaxel - paw withdrawal threshold | Two-way ANOVA | Sidak's multiple comparisons post hoc test Vehicle vs. 5 bk: Pre: p >0.9999    0 min: p > 0.9999    30 min: p = 0.9994    60 min: p > 0.9999 | Vehicle n = 6 5bk n = 6 for all conditions | |

TABLE 1-continued

Statistical analyses of experiments.

| FIG. panel | Assay | Statistical test; findings | Post-hoc analysis (adjusted p-values) | Number of subjects | Number of subjects excluded (ROUT test) |
|---|---|---|---|---|---|
| FIG. 16H | Paclitaxel nerve injury - % anti-allodynia | Two-way ANOVA | 120 min: p = 0.0042<br>180 min: p = 0.0009<br>240 min: p = 0.0248<br>300 min: p > 0.9999<br>Sidak's multiple comparisons post hoc test<br>Vehicle vs. 5 bk:<br>  30 min: p = 0.9989<br>6 0 min: p = 0.9996<br>120 min: p = 0.0134<br>180 min: p = 0.0040<br>240 min: p = 0.0346<br>300 min: p = 0.9912 | Vehicle n = 6<br>5bk n = 6<br>for all<br>conditions | |
| FIG. 16I | Paclitaxel nerve injury - Area under the curve | | Mann Whitney test<br>Vehicle vs. 5 bk p = 0.0260 | Vehicle n = 6<br>5bk n = 6 | |
| FIG. 17A | Rotarod | Two-way ANOVA | Sidak's multiple comparisons post hoc test<br>Vehicle vs. 5 bk:<br>Pre: p >0.9999<br>  30 min: p = 0.9999<br>  60 min: p = 0.9995<br>120 min: p = 0.9893<br>180 min: p > 0.9999<br>240 min: p = 0.9960<br>300 min: p > 0.9999 | Vehicle n = 6<br>5bk n = 6<br>for all<br>conditions | |
| FIG. 17B | Anxiety (elevated plus maze) | Mann-Whitney p = 0.6230 | | Vehicle n = 7<br>5bk n = 7 | |

Example IV

Materials and Methods

Compound Synthesis Strategy and Characterization

The screening library was derived from Inventors' previous work in developing inhibitors targeting the influenza virus polymerase PA-PB1 inhibitors and the T-type Ca2+ channel blockers.

Animals

Pathogen-free adult female Sprague-Dawley rats (~100 g, Envigo, Placentia, CA) were kept in light (12-h light: 12-h dark cycle; lights on at 07:00 h) and temperature (23±3° C.) controlled rooms. Standard rodent chow and water were available ad libitum. All animal use was conducted in accordance with the National Institutes of Health guidelines, and the study was conducted in strict accordance with recommendations in the Guide for the Care and Use of Laboratory Animals of the University of Arizona (Protocol #: 16-141). All animals were housed and bred in the University of Arizona Laboratory Animal Research Center. All efforts were made to minimize animal suffering.

Dorsal Root Ganglion Neuronal Cultures

Dorsal root ganglia (DRG) from all levels were dissected from 100 g female Sprague-Dawley rats using known procedures as described previously (Bellampalli, S. S., Ji, Y., Moutal, A., Cai, S., Wijeratne, E. M. K., Gandini, M. A., Yu, J., Chefdeville, A., Dorame, A., Chew, L. A., Madura, C. L., Luo, S., Molnar, G., Khanna, M., Streicher, J. M., Zamponi, G. W., Gunatilaka, A. A. L., and Khanna, R. (2019) Betulinic acid, derived from the desert lavender Hyptis emoryi, attenuates paclitaxel-, HIV-, and nerve injury-associated peripheral sensory neuropathy via block of N- and T-type calcium channels, Pain 160, 117-135.) (hereinafter "Bellampalli et al."). Dorsal root ganglia were excised and placed in sterile DMEM (Cat #11965; Thermo Fisher Scientific, Waltham, MA). The ganglia were dissociated enzymatically with collagenase type I (5 mg/mL, Cat #LS004194; Worthington) and neutral protease (3.125 mg/mL, Cat #LS02104; Worthington, Lakewood, NJ) for 50 minutes at 37° C. under gentle agitation. The dissociated cells were then centrifuged (800 rpm for 3 min), and resuspended in DMEM containing 1% penicillin/streptomycin sulfate (Cat #15140, Life Technologies), 30 ng/mL nerve growth factor (Cat #N2513, Millipore Sigma), and 10% fetal bovine serum [HyClone]). The cells were seeded on poly-d-lysine- and laminin-coated 12- or 15-mm glass coverslips and incubated at 37° C. All cultures were used within 48 hours (Cat #P6407, Millipore Sigma).

Calcium Imaging

Changes in depolarization-induced calcium influx in rat DRG neurons were determined by loading neurons with 3 mM Fura-2AM for 30 minutes at 37° C. (Cat #F1221; Thermo Fisher, stock solution prepared at 1 mM in DMSO, 0.02% pluronic acid, Cat #P-3000MP; Life Technologies, Carlsbad, CA) as previously described in Bellampalli et al. DRG neurons were incubated overnight with 10 µM and 20 µM of test compounds. A standard bath solution containing 139 mM NaCl, 3 mM KCl, 0.8 mM $MgCl_2$, 1.8 mM $CaCl_2$), 10 mM Na-HEPES, 5 mM glucose, pH 7.4, was used. Depolarization was evoked with a 10 sec pulse of 40-potassium chloride. Fluorescence imaging was achieved with an inverted microscope, Nikon Eclipse TE2000-U, using an objective Nikon Super Fluor 4× and a Photometrics-cooled CCD camera CoolSNAPHQ (Roper Scientific, Tucson, AZ) controlled by Nis Elements software (version 4.20; Nikon Instruments). The excitation light was delivered by a Lambda-LS system (Sutter Instruments, Novato, CA). The excitation filters (340±5 nm and 380±7 nm) were controlled by a Lambda 10 to 2 optical filter change (Sutter Instruments). Fluorescence was recorded through a 505-nm dichroic mirror at 535±25 nm. Images were taken every ~2.4 seconds during the time course of the experiment to minimize photobleaching and phototoxicity. To provide acceptable image quality, a minimal exposure time that provided acceptable image quality was used. Changes in $[Ca^{2+}]c$ were monitored following a ratio of $F_{340}/F_{380}$, calculated after subtracting the background from both channels.

Whole-Cell Patch-Clamp Recordings of Total $Ca^{2+}$ Currents in Acutely Dissociated DRG Neurons Recordings were obtained from acutely dissociated DRG neurons as described in Bellampalli et al. Patch-clamp recordings were performed at room temperature (22-24° C.). Currents were recorded using an EPC 10 Amplifier-HEKA (HEKA Elektronik, Ludwigshafen, Germany) linked to a computer with Patchmaster software. DRG neurons were incubated overnight (~16-24 h) with 20 μM of 3-25-R and 3-14-3-S.

For total calcium current ($ICa^{2+}$) recordings, the external solution consisted of the following (in mM): 110 N-methyl-D-glucamine, 10 BaCl$_2$, 30 TEA-Cl, 10 HEPES, 10 glucose, 0.001 TTX (pH 7.29 adjusted with NaOH, and mOsm/L=310). Patch pipettes were filled with an internal solution containing (in mM): 150 CsCl2, 10 HEPES, 5 Mg-ATP, and 5 BAPTA, (pH 7.24 adjusted with CsOH, and from a holding potential of −90 mV to obtain the current-voltage (I-V) relation. Normalization of currents to each cell's capacitance (pF) was performed to allow for collection of current density data. For I-V curves, functions were fitted to data using a non-linear least squares analysis. I-V curves were fitted using double Boltzmann functions:

$$f=a+g1/(1+\exp((x-V_{1/2}1)/k1))+g2/(1+\exp(-(x-V_{1/2}2)/k2))$$

where x is the prepulse potential, $V_{1/2}$ is the mid-point potential and k is the corresponding slope factor for single Boltzmann functions. Double Boltzmann fits were used to describe the shape of the curve, not to imply the existence of separate channel populations. Numbers 1 and 2 simply indicate first and second mid-points; a along with g are fitting parameters.

Activation curves were obtained from the I-V curves by dividing the peak current at each depolarizing step by the driving force according to the equation: $G=I/(V_{mem}-E_{rev})$, where I is the peak current, $V_{mem}$ is the membrane potential and $E_{rev}$ is the reversal potential. The conductance (G) was normalized against the maximum conductance ($G_{max}$). Steady-state inactivation (SSI) curves were obtained by applying an H-infinity protocol that consisted of 1.5-seconds conditioning pre-pulses from −100 to +30 mV in 10-mV increments followed by a 20-millisecond test pulse to +10 mV. Inactivation curves were obtained by dividing the peak current recorded at the test pulse by the maximum current ($I_{max}$). Activation and SSI curves were fitted with the Boltzmann equation.

Cell Culture and Transient Transfection of HEK293T Cells

Human embryonic kidney HEK293T cells were cultured in DMEM supplemented with 10% fetal bovine serum and 1% penicillin/streptomycin sulfate, maintained in standard conditions (5% $CO_2$, 37° C., saturated humidity). Cells were transfected with 2 μg of either of the channel cDNAs using Lipofectamine 2000 when cell confluence reached 70-90%. Four to six hours after transfection, cells were seeded onto poly-l-lysine-coated coverslips. Positively transfected cells were indicated by the fluorescence of co-transfected enhanced green fluorescent protein (0.2 μg). All the experiments were performed 36 hours after cell transfection.

Whole-Cell Patch-Clamp Recordings of $Ca^{2+}$ Currents in Transiently Transfected HEK293T Cells For electrophysiological recording, the external solution contained (in mM): 105 CsCl, TEA-Cl, 2 CaCl$_2$), 1 MgCl$_2$, and 10 glucose (pH 7.4 adjusted with CsOH, and mOsm/L=295-305). The internal solution consisted of (in mM): 120 CsMeSO$_4$, 11 EGTA, 2 Mg-ATP, and HEPES (pH 7.4 adjusted with CsOH, and mOsm/L=295-305). All experiments were conducted at room temperature (22-24° C.). The T-type calcium currents were elicited by a depolarization to −20 or −10 mV for 200-millisecond from a hold potential of −90 mV. Data were collected by the Patchmaster software in a HEKA EPC-10 USB patch-clamp system. Voltage errors were minimized by using 80% series resistance compensation. The capacitance artifact was canceled by using the computer-controlled circuitry of the patch-clamp amplifier. The concentration-response curves of the test compounds on CaV3 channels were fitted to a Hill equation to estimate the potency of the compounds ($IC_{50}$).

Behavior Pain Panel

The analgesic profile of 3-14-3-S was analyzed by an in vivo screening tool, ALGOGram™ (ANS Biotech, Riom, France). This platform allowed for obtaining information about the effects of compounds in 5 different pain areas (Acute and tonic pain, inflammatory pain, neuropathic pain, postoperative pain and visceral pain), by comparing their activity on a battery of 10 validated behavioral pain models with an ANS Biotech reference historical database (Table 1). Assessment of the efficacy, and analgesic effects of a single administration (0.4 μg/μl, i.t.) 3-14-3-S was analyzed in the rat models of. Tail flick test in healthy rats, paw pressure test in healthy rats, acetic acid-induced writhing, formalin test, Bennett model of peripheral mononeuropathy, oxaliplatin-induced neuropathy, carrageenan-induced mechanical hyperalgesia, kaolin-induced arthritis, Brennan model of incisional pain; and trinitrobenzene sulfonic acid (TNBS)-induced visceral hypersensitivity (Table 2).

TABLE 2

Effects of a single administration (0.4 μg/μl, i.t.) of 3-14-3-S in ALGOGram ™.

| Pain area | Model (Test) | 3-14-3-S Percentage of activity vs. vehicle | Internal reference Reference ID | Percentage of activity vs. vehicle |
|---|---|---|---|---|
| Acute and tonic pain | Healthy rats (Paw pressure test) | 3% | Morphine 4 mg/kg s.c., T30 min | 67% |
| | Healthy rats (Tail flick test) | 5% | Morphine 4 mg/kg s.c., T30 min | 66% |
| | Acetic acid test (Abdominal cramps) | 33% | (−) U50, 488 H 3 mg/kg s.c., T30 min | 100% |
| | Formalin test (Paw licking time early phase) | 16% | Morphine 4 mg/kg s.c., T30 min | 65% |
| | Formalin test (Paw licking time late phase) | 36% | Morphine 4 mg/kg s.c., T30 min | 77% |
| Neuropathic pain | Bennett model (Paw pressure test) | 14% | Morphine 3 mg/kg s.c., T30 min | 188% |
| | Oxaliplatin (Paw Immersion test) | 6% | Duloxetine 100 mg/kg, p.o., T60 min | 66% |
| Inflammatory pain | Carrageenan (Paw pressure test) | 29% | Indomethacin 30 mg/kg, p.o., T60 min | 92% |

TABLE 2-continued

Effects of a single administration (0.4 µg/µl, i.t.)
of 3-14-3-S in ALGOGram ™.

| | | 3-14-3-S | Internal reference | |
|---|---|---|---|---|
| Pain area | Model (Test) | Percentage of activity vs. vehicle | Reference ID | Percentage of activity vs. vehicle |
| | Kao lin (Gait score) | -13% | Indomethacin 30 mg/kg, p.o., T60 min | 64% |
| Post-operative pain | Brennan model (Electronic Von Frey test) | -10% | Morphine 4 mg/kg s.c., T30 min | 107% |
| Visceral pain | TN BS (Colonic distension) | -11% | (-) U50, 488 H 3 mg/kg s.c., T30 min | 168% |

Testing: 120 min after treatment. n=4/model/test (excepted for 3-14-3-S-treated group in Oxaliplatin model n=3). Results are expressed for each group as a percentage of activity calculated from the mean value of the vehicle-treated animals and compared to naïve animals, control paw or cut-off value, depending on the test (from the ANS Biotech historical database).

Ligand Docking

Protein and ligand preparation and docking were conducted using the Schrodinger Docking Suite. Jun3-14-3-S and Z944 was prepared using LigPrep with possible ionization states at pH 7.0. The CryoEM structure of human CaV3.1 (PDB ID 6kzp) was prepared using the Protein Preparation Wizard and the charge on K1462 was manually adjusted from +1 to 0 prior to SiteMap analysis and docking. For docking, an enclosing box was generated at the centroid of residues N388, F956, V1505, V1820 at the default size and the ligand-midpoint box was expanded to 25×25×15 A to include the 3 open fenestrations. Docking was performed with Glide Standard Precision (SP) mode. The better of two poses was selected for visualization based on contacts and docking scores. Figures were generated with PyMOL.

Data Analysis

Graphing and statistical analysis was performed with GraphPad Prism (Version 9). All data sets were checked for normality using D'Agostino & Pearson test. Details of statistical tests, significance and sample sizes are reported in the appropriate figure legends. All data plotted represent mean±SEM. For electrophysiological recordings: peak current density as well as $V_{1/2}$ midpoint potential and k slope factor were compared using One-way ANOVA with the Tukey post hoc test.

Results and Discussion

Identification of 5bk-Derivative Compounds that Target T-Type $Ca^{2+}$ Channels in Sensory Neurons.

An analog of benzimidazolonepiperidine—5bk was previously identified as a modulator of the LVA $Ca^{2+}$ channels with a therapeutic potential for pain relief In order to discover novel compounds for pain treatment, 5bk was selected for additional optimization to accomplish preferential activity towards T-type $Ca^{2+}$ channels and a series of 47 compound derivatives were created (FIG. 21A). By using Fura 2-AM-based ratiometric calcium-imaging assays, the initial screen exhibited that in rat sensory neurons, compounds 1-159-2, 3-14-3 and 3-25 (at 20 µM) were the most potent inhibitors of potassium chloride (KCl)-evoked $Ca^{2+}$ influx triggered with 40 mM KCl. Compounds 1-159-2, 3-14-3 and 3-25 decreased $Ca^{2+}$ influx by ~92% (8.21±1.08%, n=51), ~73% (26.9±4.014%, n=93), and ~77% (22.2±1.67%, n=315) respectively, when compared to the control (0.05% DMSO) (FIG. 21B).

Next, the enantiomers of 1-159-2, 3-14-3, and 3-25 were separated by chiral HPLC and tested on whether the R or S enantiomer had more profound ability to block $Ca^{2+}$ influx (FIG. 21C). DRG stimulation with 40 mM KCl led to an increase in $Ca^{2+}$ influx as shown in the control group (0.05% DMSO) (FIGS. 21B, 22D, and 22E). Overnight incubation with 10 µM of derivative compounds revealed that, 3-25-R, 3-14-3-S and 1-159-2-R markedly suppressed average peak response (3-25-R: 28.5±2.0%, n=724; 3-14-3-S: 33.7±2.0%, n=869; 1-159-2-R: 33.5±2.1%, n=935) (FIGS. 21D and 22E) when compared to the control group. In comparison, 3-25-S (86.1±2.0%), 3-14-3-R (55.2±5.1%), and 1-159-2-S (42.0±2.2%) were less active.

Unlike HVA $Ca^{2+}$ channels, T-type $Ca^{2+}$ channels activate at voltages near the resting membrane potential. Previous works have reported that depolarizing superior cervical ganglia neurons with 40 mM $K^+$ changed the membrane voltage to ~-20 mV [19]. At this potential, T-type $Ca^{2+}$ channels are activated, whilst the majority of HVA $C^a$ channels are still in a closed state. Notwithstanding, mild depolarizations like this one could activate CaV1 channels in the DRGs, whereas stronger depolarizations (>60 mM $K^+$) could recruit CaV2 channels. To avoid any possible effects of 3-25-R, 3-14-3-S and 1-159-2-R on HVA $Ca^{2+}$ channels, $Ca^{2+}$ influx in DRG neurons was triggered with 90 mM KCl and found that $Ca^{2+}$ entry was less affected than with 40 mM (3-25-R: 62.43±1.967%, n=296; 3-14-3-S: 87.25±2.245%, n=228; 1-159-2-R: 67.37±2.294%, n=575) (data not shown). Whereby, these results suggest that inhibition of $Ca^{2+}$ influx by compounds 3-25-R, 3-14-3-S and 1-159-2-R was achieved by targeting T-type $Ca^{2+}$ channels.

Compounds 3-25-R and 3-14-3-S Decrease $Ca^{2+}$ Currents in Rat DRG Neurons

The above experiments identify three 5bk derivatives 3-25-R, 3-14-3-S and 1-159-2-R as potent inhibitors of VGCCs. To further assess if $Ca^{2+}$ currents were altered by the compounds, the two enantiomers 3-14-3-S and 3-25-R were selected and whole-cell patch-clamp recordings were performed in small- to medium-sized DRG neurons. Cells were treated overnight with a µM concentration of 3-14-3-S, 3-25-R or control (0.1% DMSO). From a holding potential of -90 mV, 200-ms depolarization steps from -70 to +60 mV (10 mV increments) evoked a family of $Ca^{2+}$ currents (FIG. 22A). Next current density-voltage relationships (FIG. 22B) were measured and it was observed that incubation with 3-14-3-S and 3-25-R decreased $Ca^{2+}$ current density at the majority of the voltages tested (FIG. 22B). Furthermore, at peak current density (FIG. 22C), the reduction in $Ca^{2+}$ currents imposed by 3-14-3-S and 3-25-R was ~56.97% and ~44.17% respectively, when compared to cells treated with 0.1% DMSO (DMSO: -96.91±12.39 pA/pF; 3-14-3-S: -41.70±7.927 pA/pF; 3-25-R: -54.1±8.385 pA/pF). Inspection of voltage-dependence of activation revealed no difference in the half activation potential and slope factors between groups (FIG. 22D and Table 3). Steady-state inactivation kinetics of the channels at multiple test potentials were also assessed by measuring the fraction of current remaining at +10 mV. As seen in FIG. 22D and Table 3, the results revealed no significant differences in half inactivation potential and slope factors between conditions. Collectively, the data corroborate the findings that both 3-25-R and 3-14-3-S, are tonic rather than state-dependent $Ca^{2+}$ channel blockers.

Half-maximal activation potential of activation and inactivation (V1/2) and slope values (k) for activation and inactivation are presented in Table 3.

TABLE 3

| Gating properties of calcium currents recorded from rat DRG neurons. | | | |
|---|---|---|---|
| | DMSO | 3-25-R | 3-14-3-S |
| Activation V1/2 | 1.817 ± 0.623 (8) | 2.383 ± 2.037 (10) | 4.083 ± 2.038 (9) |
| k | 5.250 ± 0.552 (8) | 9.659 ± 1.798 (10) | 9.308 ± 1.780 (9) |
| Inactivation V1/2 | −21.702 ± 0.786 (14) | −26.709 ± 2.655 (13) | −25.246 ± 2.129 (11) |
| k | −10.078 ± 0.711 (14) | −15.208 ± 2.714 (13) | −12.570 ± 2.035 (11) |

Values are means SEM calculated from fits of the data from the indicated number of individual cells (in parentheses) to the Boltzmann equation; $V_{1/2}$ midpoint potential (mV) for voltage-dependent of activation or inactivation; k, slope factor. These values pertain to FIG. 22. Data were analyzed with one-way ANOVA with Tukey post hoc test. DRG, dorsal root ganglia; DMSO, dimethyl sulfoxide; ANOVA, analysis of variance.

In situ hybridization studies have shown that all three CaV3 $Ca^{2+}$ channel isoforms are present in DRG sensory neurons. Medium-sized DRGs are the cells with the highest expression of functional T-type $Ca^{2+}$ channels, followed by small DRGs. Medium and small DRG neurons belong to lightly myelinated Aδ and unmyelinated C fibers. These primary afferent fibers are necessary for pain transmission since they send nociceptive information to the dorsal horn of the spinal cord. Calcium channels expressed along these fibers can facilitate the opening of $Na^+$ channels and therefore increase action potential firing frequency with the subsequent neurotransmitter release and increased excitability in the spinal cord. During pain conditions, exacerbated $Ca^{2+}$ influx has been observed due to an increase in the functional expression of VGCCs. Thus, inhibiting $Ca^{2+}$ currents in nociceptive DRGs has shown to have a therapeutic potential for pain relief.

Compound 3-14-3-S but not 3-25-R, Inhibits Transiently Expressed T-Type $Ca^{2+}$ Channels.

The previous data confirm that compounds 3-25-R and 3-14-3-S inhibit the functional activity of VGCCs. Because the initial results showed potential inhibition of LVA $Ca^{2+}$ channels (evoked by 40-mM KCl) (FIGS. 21B-1E), the focus was on T-type $Ca^{2+}$ channels. Even though the most abundant T-type $Ca^{2+}$ channel isoform existing in sensory neurons is CaV3.2, all three channel isoforms are present and display a relevant role in pain processing In this context, to decipher whether 3-25-R and 3-14-3-S could preferentially target a particular T-type $Ca^{2+}$ channel isoform, the individual T-type channel al-subunits were transiently transfected in HEK293T cells and measured whole-cell $Ca^{2+}$ currents by patch-clamp. Cells were incubated overnight with 3-25-R and 3-14-3-S at a final concentration of 50 μM. Subsequently, from a hold potential of −90 mV, T-type $Ca^{2+}$ currents were evoked by depolarizing the cell membrane to −20 or −10 mV (depending on each cell's specific I-V relationship) for 200-ms. Surprisingly, application of 3-25-R had negligible effects on CaV3.1, CaV3.2 and CaV3.3 mediated currents (FIG. 23A). In other words, $Ca^{2+}$ influx through these channels was not affected by 3-25-R. On the contrary, compound 3-14-3-S inhibited $Ca^{2+}$ entry through CaV3.1, CaV3.2 and CaV3.3 channels (FIG. 23B). Representative current traces in FIG. 23B shows that 3-14-3-S strongly suppressed LVA currents.

To complement these findings, concentration-response curves were generated to compare the potency of 3-14-3-S against all three T-type $Ca^{2+}$ channel isoforms (FIG. 23C). The inhibition of $Ca^{2+}$ currents in HEK293T cells by 3-14-3-S was concentration-dependent. 3-14-3-S inhibited CaV3.1, CaV3.2 and CaV3.3 channels with a similar $IC_{50}$ (23.02 μM for CaV3.1 at the depolarizing voltage of −10 mV, 35.58 μM for CaV3.2 at the depolarizing voltage of −10 mV, and 26.27 μM for CaV3.3 at the depolarizing voltage of −10 mV) (FIG. 23C). Since compound 3-25-R did not exert a significant block of LVA $Ca^{2+}$ currents, concentration-response curves were not constructed. Overall, the results suggest that compound 3-14-3-S acts as a pan-T-type calcium channel blocker. Moreover, earlier results indicated that 3-25-R showed a greater block of $Ca^{2+}$ influx than 3-14-3-S when DRGs were challenged with 90 mM KCl (data not shown). Thus, $Ca^{2+}$ current reductions imposed by 3-25-R (FIGS. 22A-23D) could have possibly been by inhibiting other VGCCs, for instance, HVA $Ca^{2+}$ channels.

Compound 3-14-3-S Reverses Nociceptive Behaviors in Experimental Models of Acute and Tonic, Neuropathic and Inflammatory Pain.

Because the initial goal was to target T-type $Ca^{2+}$ channels, compound 3-14-3-S was selected for additional feature analysis. Given the blocking activity of T-type $Ca^{2+}$ channels by 3-14-3-S, it was hypothesized that this compound could reverse nociception in different rodent models of pain. Hence, ALGOGram™ was employed, which is an in vivo screening tool that encompasses various preclinical models within the areas of acute and tonic pain, neuropathic pain, inflammatory pain, post-operative pain, and visceral pain (Table 1). The percentage of activity of the compound against the vehicle group was compared to an ANS Biotech internal reference according to the pain model used (Table 1). Firstly, in healthy rats, paw pressure test and tail flick test revealed that a single administration of compound 3-14-3-S (0.4 μg/μl, i.t.) maintained acute mechanical and thermal sensitivity intact (3 and 5% of activity respectively), emphasizing that the protective role of pain is minimally affected by this compound. Furthermore, the percentage of activity of 3-14-3-S in the acetic acid test (0.6% acetic acid), a parenterally administered chemical irritant that induces abdominal writhing movements in rats, was 33% (Internal reference and % of activity: (−) U50, 488 H, 100%). Likewise, administration of 3-14-3-S in the formalin test for nociception (2.5% formalin), yielded a percentage of activity of 16% and 36% in the early and late phase, respectively (Internal reference and % of activity: Morphine, 65% and 77%). The early phase seems to be caused mainly by activation of nociceptors, while the late phase appears to be due to functional changes occurring in the dorsal horn of the spinal cord [26], [27]. Thus, the data suggest that compound 3-14-3-S partially alleviates tonic pain (Table 2). *****

Within the neuropathic and inflammatory pain areas, in rats subjected to chronic constriction injury (Bennett model), 3-14-3-S had 14% of activity compared to vehicle treated group (Internal reference and % of activity: Morphine, 1[88]%). Meanwhile, the effect in Oxaliplatin-induced peripheral neuropathy (10 mg/kg oxaliplatin) was less pronounced. Intrathecal injection of 3-14-3-S produced 6% of activity in this model (Internal reference and % of activity: Duloxetine, 66%). On the other hand, in the inflammatory pain model induced by intraplanar injection of 2% carra-geenan, the percentage of activity of 3-14-3-S was reported to be 29% (Internal reference and % of activity: Indometha-cin, 92%). Nevertheless, 3-14-3-S was not efficacious when 10% Kaolin was administered into rats to induce arthritis (~13% of activity; Internal reference and % of activity: Indomethacin, 64%). Similarly, compound 3-14-3-S had no effect in the Brennan model of post-operative pain and in TNBS-induced visceral pain (50 mg/kg) (~10 and −11% of activity; Internal reference and % of activity: Morphine, 107%; and (−) U50, 488 H, 168%). Individual raw data is available in FIGS. 24A-25E. Overall, these results show that compound 3-14-3-S has a modest effect in nerve-injury induced neuropathic pain model and in carrageenan-induced inflammatory pain.

Accumulating evidence strongly suggest the involvement of LVA channels in pain Among the different T-type $Ca^{2+}$ channel isoforms expressed in the DRGs, CaV3.2 is pre-dominant. From increased mRNA and protein expression, to augmented T-type $Ca^{2+}$ currents and neuronal excitability in the DRGs and spinal cord, these channels have been impli-cated in several models of neuropathic, inflammatory and visceral pain. In mice lacking CaV3.2 channels, nociceptive responses were attenuated in various behavioral models of pain. Similarly, pharmacological inhibition of this channel has been utilized to expose the role of CaV3.2 in pain processing. This evidence highlights that targeting CaV3.2 channels offers a safe strategy for treatment of pain.

Along the same lines, CaV3.1 and CaV3.3 are also involved in the pathophysiology of pain from different etiologies. CaV3.1-null mice showed attenuated mechanical allodynia and thermal hyperalgesia in a neuropathic pain model of spinal nerve ligation. Similarly, previous works showed that intrathecal administration of antisense oligo-nucleotides directed against CaV3.3 reduced tactile allody-nia and thermal hyperalgesia after chronic compression of the DRGs, suggesting that Cav3.3 channels play a role in neuropathic pain. In addition, CaV3.1 and CaV3.3 have also been implicated in trigeminal neuropathic pain. CaV3.1 channel knockout and pharmacological blockade of Cav3.3 showed effectiveness in attenuating trigeminal neuropathic pain. Hence, CaV3.1 and CaV3.3 channels are relevant in the pathophysiology of pain and positions them as strategic targets to treat pain. Therefore, inhibition of T-type $Ca^{2+}$ channel isoforms by compound 3-14-3-S could potentially contribute to the antinociceptive effects observed in ALGO-Gram™. Overall, the behavioral results suggest that multi-targeting T-type $Ca^{2+}$ channels could be a more efficacious tactic to combat pain. A good example that blocking all three T-Type channels subtypes is beneficial for pain treatment is Z944. This compound is a pan-T-type $Ca^{2+}$ channel modu-lator that had a potential activity in modulating pain signal-ing in humans. Thus, the results lay the foundation for further experimental studies to identify inhibitors that target T-type $Ca^{2+}$ channels to resolve pain.

3-14-3-S Docking to CaV3.1 Channel.

Of the T-type channel isoforms, only structures of CaV3.1 are known at this time; thus 3-14-3-S was docked to the CaV3.1 structure with bound T-type inhibitor Z944 (FIGS. 25A-26C). Compared to the apo CaV3.1 structure, the Z944 bound structure exhibits partial unwinding of S6-II, placing residue F956 (F1007 in CaV3.2, F854 in CaV3.3) in the pore where it is thought to be important for inhibitor binding. 3-14-3-S docked in a conformation similar to that of Z944 with the 2-methylthiophene moiety located in fenestration II-III, the tetrazole within hydrogen bonding distance of K1462, and the piperazine ring within van der Waals distance of F956 (FIGS. 25B, 25C). However, 3-14-3-S does not extend towards the pore gate, deviating from the 'bent' conformation of Z944 at the benzaldehyde group which remains in the upper central portion of the pore (FIG. 25B).

INCORPORATION BY REFERENCE

The entire disclosure of each of the patent documents and scientific articles referred to herein is incorporated by ref-erence for all purposes. The following references are herein incorporated by reference in their entireties:

[1] Aziz-Donnelly A, Harrison T B. Update of HIV-Asso-ciated Sensory Neuropathies. Curr Treat Options Neurol 2017; 19(10):36.

[2] Bauer C S, Rahman W, Tran-van-Minh A, Lujan R, Dickenson A H, Dolphin A C. The anti-allodynic alpha (2)delta ligand pregabalin inhibits the trafficking of the calcium channel alpha(2)delta-1 subunit to presynaptic terminals in vivo. Biochemical Society transactions 2010; 38(2):525-528.

[3] Bellampalli S S, Ji Y, Moutal A, Cai S, Wijeratne E M K, Gandini M A, Yu J, Chefdeville A, Dorame A, Chew L A, Madura C L, Luo S, Molnar G, Khanna M, Streicher J M, Zamponi G W, Gunatilaka A A L, Khanna R. Betulinic acid, derived from the desert lavender Hyptis emoryi, attenuates paclitaxel-, HIV-, and nerve injury-associated peripheral sensory neuropathy via block of N- and T-type calcium channels. Pain 2019; 160(1):117-135.

[4] Bernal Sierra Y A, Haseleu J, Kozlenkov A, Begay V, Lewin G R. Genetic Tracing of Cav3.2 T-Type Calcium Channel Expression in the Peripheral Nervous System. Frontiers in molecular neuroscience 2017; 10:70.

[5] Blesneac I, Chemin J, Bidaud I, Huc-Brandt S, Vander-moere F, Lory P. Phosphorylation of the Cav3.2 T-type calcium channel directly regulates its gating properties. Proceedings of the National Academy of Sciences of the United States of America 2015; 112(44):13705-13710.

[6] Bourinet E, Alloui A, Monteil A, Barrere C, Couette B, Poirot O, Pages A, McRory J, Snutch T P, Eschalier A, Nargeot J. Silencing of the Cav3.2 T-type calcium channel gene in sensory neurons demonstrates its major role in nociception. EMBO J 2005; 24(2):315-324.

[7] Brittain J M, Duarte D B, Wilson S M, Zhu W, Ballard C, Johnson P L, Liu N, Xiong W, Ripsch M S, Wang Y, Fehrenbacher J C, Fitz S D, Khanna M, Park C K, Schmutzler B S, Cheon B M, Due M R, Brustovetsky T, Ashpole N M, Hudmon A, Meroueh S O, Hingtgen C M, Brustovetsky N, Ji R R, Hurley J H, Jin X, Shekhar A, Xu X M, Oxford G S, Vasko M R, White F A, Khanna R. Suppression of inflammatory and neuropathic pain by uncoupling CRMP-2 from the presynaptic Ca(2)(+) chan-nel complex. Nature medicine 2011; 17(7):822-829.

[8] Calvo M, Davies A J, Hebert H L, Weir G A, Chesler E J, Finnerup N B, Levitt R C, Smith B H, Neely G G, Costigan M, Bennett D L. The Genetics of Neuropathic Pain from Model Organisms to Clinical Application. Neuron 2019; 104(4):637-653.

[9] Candelas M, Reynders A, Arango-Lievano M, Neumayer C, Fruquiere A, Demes E, Hamid J, Lemmers C, Bernat C, Monteil A, Compan V, Laffray S, Inquimbert P, Le Feuvre Y, Zamponi G W, Mogrich A, Bourinet E, Mery P F. Cav3.2 T-type calcium channels shape electrical firing in mouse Lamina I I neurons. Sci Rep 2019; 9(1):3112.

[10] Catterall W A. Structure and function of neuronal $Ca^{2+}$ channels and their role in neurotransmitter release. Cell calcium 1998; 24(5-6):307-323.

[11] Chaplan S R, Bach F W, Pogrel J W, Chung J M, Yaksh T L. Quantitative assessment of tactile allodynia in the rat paw. Journal of neuroscience methods 1994; 53(1):55-63.

[12] Chen W, Chi Y N, Kang X J, Liu Q Y, Zhang H L, Li Z H, Zhao Z F, Yang Y, Su L, Cai J, Liao F F, Yi M, Wan Y, Liu F Y. Accumulation of Cav3.2 T-type Calcium Channels in the Uninjured Sural Nerve Contributes to Neuropathic Pain in Rats with Spared Nerve Injury. Frontiers in molecular neuroscience 2018; 11:24.

[13] Chen Y L, Tsaur M L, Wang S W, Wang T Y, Hung Y C, Lin C S, Chang Y F, Wang Y C, Shiue S J, Cheng J K. Chronic intrathecal infusion of mibefradil, ethosuximide and nickel attenuates nerve ligation-induced pain in rats. British journal of anaesthesia 2015; 115(1):105-111.

[14] Choe W, Messinger R B, Leach E, Eckle V S, Obradovic A, Salajegheh R, Jevtovic-Todorovic V, Todorovic S M. TTA-P2 is a potent and selective blocker of T-type calcium channels in rat sensory neurons and a novel antinociceptive agent. MolPharmacol 2011; 80(5):900-910.

[15] Choi S, Na H S, Kim J, Lee J, Lee S, Kim D, Park J, Chen C C, Campbell K P, Shin H S. Attenuated pain responses in mice lacking Ca(V)3.2 T-type channels. Genes Brain Behav 2007; 6(5):425-431.

[16] DePuy S D, Yao J, Hu C, McIntire W, Bidaud I, Lory P, Rastinejad F, Gonzalez C, Garrison J C, Barrett P Q. The molecular basis for T-type $Ca^{2+}$ channel inhibition by G protein beta2gamma2 subunits. Proceedings of the National Academy of Sciences of the United States of America 2006; 103(39):14590-14595.

[17] Dustrude E T, Moutal A, Yang X, Wang Y, Khanna M, Khanna R. Hierarchical CRMP2 posttranslational modifications control NaV1.7 function. Proceedings of the National Academy of Sciences of the United States of America 2016; 113(52):E8443-E8452.

[18] Dustrude E T, Wilson S M, Ju W, Xiao Y, Khanna R. CRMP2 protein SUMOylation modulates NaV1.7 channel trafficking. The Journal of biological chemistry 2013; 288(34):24316-24331.

[19] Egan M F, Zhao X, Smith A, Troyer M D, Uebele V N, Pidkorytov V, Cox K, Murphy M, Snavely D, Lines C, Michelson D. Randomized controlled study of the T-type calcium channel antagonist MK-8998 for the treatment of acute psychosis in patients with schizophrenia. Hum Psychopharmacol 2013; 28(2):124-133.

[20] Feng X J, Ma L X, Jiao C, Kuang H X, Zeng F, Zhou X Y, Cheng X E, Zhu M Y, Zhang D Y, Jiang C Y, Liu T. Nerve injury elevates functional Cav3.2 channels in superficial spinal dorsal horn. Molecular pain 2019; 15:1744806919836569.

[21] Flatters S J, Bennett G J. Ethosuximide reverses paclitaxel- and vincristine-induced painful peripheral neuropathy. Pain 2004; 109(1-2):150-161.

[22] Francois A, Schuetter N, Laffray S, Sanguesa J, Pizzoccaro A, Dubel S, Mantilleri A, Nargeot J, Noel J, Wood J N, Mogrich A, Pongs O, Bourinet E. The Low-Threshold Calcium Channel Cav3.2 Determines Low-Threshold Mechanoreceptor Function. Cell Rep 2015.

[23] Francois-Moutal L, Wang Y, Moutal A, Cottier K E, Melemedjian O K, Yang X, Wang Y, Ju W, Largent-Milnes™, Khanna M, Vanderah T W, Khanna R. A membrane-delimited N-myristoylated CRMP2 peptide aptamer inhibits CaV2.2 trafficking and reverses inflammatory and postoperative pain behaviors. Pain 2015; 156(7):1247-1264.

[24] Friesner R A, Banks J L, Murphy R B, Halgren T A, Klicic J J, Mainz D T, Repasky M P, Knoll E H, Shelley M, Perry J K, Shaw D E, Francis P, Shenkin P S. Glide: a new approach for rapid, accurate docking and scoring. 1. Method and assessment of docking accuracy. Journal of medicinal chemistry 2004; 47(7):1739-1749.

[25] Fukuoka T, Yamanaka H, Kobayashi K, Okubo M, Miyoshi K, Dai Y, Noguchi K. Re-evaluation of the phenotypic changes in L4 dorsal root ganglion neurons after L5 spinal nerve ligation. Pain 2012; 153(1):68-79.

[26] Garcia-Caballero A, Gadotti V M, Stemkowski P, Weiss N, Souza I A, Hodgkinson V, Bladen C, Chen L, Hamid J, Pizzoccaro A, Deage M, Francois A, Bourinet E, Zamponi G W. The deubiquitinating enzyme USP5 modulates neuropathic and inflammatory pain by enhancing Cav3.2 channel activity. Neuron 2014; 83(5):1144-1158.

[27] Girach A, Julian T H, Varrassi G, Paladini A, Vadalouka A, Zis P. Quality of Life in Painful Peripheral Neuropathies: A Systematic Review. Pain Res Manag 2019; 2019: 2091960.

[28] Gold M S, Weinreich D, Kim C S, Wang R, Treanor J, Porreca F, Lai J. Redistribution of Na(V)1.8 in uninjured axons enables neuropathic pain. The Journal of neuroscience: the official journal of the Society for Neuroscience 2003; 23(1):158-166.

[29] Gomez K, Calderon-Rivera A, Sandoval A, Gonzalez-Ramirez R, Vargas-Parada A, Ojeda-Alonso J, Granados-Soto V, Delgado-Lezama R, Felix R. Cdk5-Dependent Phosphorylation of CaV3.2 T-Type Channels: Possible Role in Nerve Ligation-Induced Neuropathic Allodynia and the Compound Action Potential in Primary Afferent C Fibers. The Journal of neuroscience: the official journal of the Society for Neuroscience 2020; 40(2):283-296.

[30] Gray W R, Olivera B M, Cruz U. Peptide toxins from venomous Conus snails. Annual review of biochemistry 1988; 57:665-700.

[31] Hamidi G A, Ramezani M H, Arani M N, Talaei S A, Mesdaghinia A, Banafshe H R. Ethosuximide reduces allodynia and hyperalgesia and potentiates morphine effects in the chronic constriction injury model of neuropathic pain. European journal of pharmacology 2012; 674(2-3):260-264.

[32] Head J, Mazza J, Sabourin V, Turpin J, Hoelscher C, Wu C, Sharan A. Waves of Pain Relief: A Systematic Review of Clinical Trials in Spinal Cord Stimulation Waveforms for the Treatment of Chronic Neuropathic Low Back and Leg Pain. World Neurosurg 2019; 131: 264-274 e263.

[33] Huynh T N, Krigbaum A M, Hanna J J, Conrad C D. Sex differences and phase of light cycle modify chronic stress effects on anxiety and depressive-like behavior. Behavioural brain research 2011; 222(1):212-222.

[34] Ibrahim M M, Patwardhan A, Gilbraith K B, Moutal A, Yang X, Chew L A, Largent-Milnes T, Malan T P, Vanderah T W, Porreca F, Khanna R. Long-lasting antinociceptive effects of green light in acute and chronic pain in rats. Pain 2017; 158(2):347-360.

[35] Jacus M O, Uebele V N, Renger J J, Todorovic S M. Presynaptic Cav3.2 channels regulate excitatory neurotransmission in nociceptive dorsal horn neurons. The Journal of neuroscience: the official journal of the Society for Neuroscience 2012; 32(27):9374-9382.

[36] Jagodic M M, Pathirathna S, Joksovic P M, Lee W, Nelson M T, Naik A K, Su P, Jevtovic-Todorovic V, Todorovic S M. Upregulation of the T-type calcium current in small rat sensory neurons after chronic constrictive injury of the sciatic nerve. JNeurophysiol 2008; 99(6):3151-3156.

[37] Jagodic M M, Pathirathna S, Nelson M T, Mancuso S, Joksovic P M, Rosenberg E R, Bayliss D A, Jevtovic-Todorovic V, Todorovic S M. Cell-specific alterations of T-type calcium current in painful diabetic neuropathy enhance excitability of sensory neurons. JNeurosci 2007; 27(12):3305-3316.

[38] Kang X J, Chi Y N, Chen W, Liu F Y, Cui S, Liao F F, Cai J, Wan Y. Increased expression of CaV3.2 T-type calcium channels in damaged DRG neurons contributes to neuropathic pain in rats with spared nerve injury. Molecular pain 2018; 14:1744806918765808.

[39] Kelley L A, Mezulis S, Yates C M, Wass M N, Stemnberg M J. The Phyre2 web portal for protein modeling, prediction and analysis. Nature protocols 2015; 10(6):845-858.

[40] Khanna R, Yu J, Yang X, Moutal A, Chefdeville A, Gokhale V, Shuja Z, Chew L A, Bellampalli S S, Luo S, Francois-Moutal L, Serafini M J, Ha T, Perez-Miller S, Park K D, Patwardhan A, Streicher J M, Colecraft H M, Khanna M. Targeting the CaVα-β interaction yields an antagonist of the N-type CaV2.2 channel with broad antinociceptive efficacy. Pain 2019.

[41] Lambert R C, Bessaih T, Leresche N. Modulation of neuronal T-type calcium channels. CNSNeurolDisordDrug Targets 2006; 5(6):611-627.

[42] Lee M. Z944: a first in class T-type calcium channel modulator for the treatment of pain. Journal of the peripheral nervous system: JPNS 2014; 19 Suppl 2:S11-12.

[43] Leresche N, Lambert R C. T-type calcium channels in synaptic plasticity. Channels (Austin) 2017; 11(2):121-139.

[44] Li Y, Tatsui C E, Rhines L D, North R Y, Harrison D S, Cassidy R M, Johansson C A, Kosturakis A K, Edwards D D, Zhang H, Dougherty P M. Dorsal root ganglion neurons become hyperexcitable and increase expression of voltage-gated T-type calcium channels (Cav3.2) in paclitaxel-induced peripheral neuropathy. Pain 2017; 158(3):417-429.

[45] Liu C N, Wall P D, Ben-Dor E, Michaelis M, Amir R, Devor M. Tactile allodynia in the absence of C-fiber activation: altered firing properties of DRG neurons following spinal nerve injury. Pain 2000; 85(3):503-521.

[46] Liu Q Y, Chen W, Cui S, Liao F F, Yi M, Liu F Y, Wan Y. Upregulation of Cav3.2 T-type calcium channels in adjacent intact L4 dorsal root ganglion neurons in neuropathic pain rats with L5 spinal nerve ligation. Neurosci Res 2019; 142:30-37.

[47] Maeda Y, Aoki Y, Sekiguchi F, Matsunami M, Takahashi T, Nishikawa H, Kawabata A. Hyperalgesia induced by spinal and peripheral hydrogen sulfide: evidence for involvement of Cav3.2 T-type calcium channels. Pain 2009; 142(1-2):127-132.

[48] Manji H. Neuropathy in HIV infection. Current opinion in neurology 2000; 13(5):589-592.

[49] Matthews E A, Dickenson A H. Effects of spinally delivered N- and P-type voltage-dependent calcium channel antagonists on dorsal hom neuronal responses in a rat model of neuropathy. Pain 2001; 92(1-2):235-246.

[50] Messinger R B, Naik A K, Jagodic M M, Nelson M T, Lee W Y, Choe W J, Orestes P, Latham J R, Todorovic S M, Jevtovic-Todorovic V. In vivo silencing of the Ca(V) 3.2 T-type calcium channels in sensory neurons alleviates hyperalgesia in rats with streptozocin-induced diabetic neuropathy. Pain 2009; 145(1-2):184-195.

[51] Milligan E D, O'Connor K A, Nguyen K T, Armstrong C B, Twining C, Gaykema R P, Holguin A, Martin D, Maier S F, Watkins L R. Intrathecal HIV-1 envelope glycoprotein gp120 induces enhanced pain states mediated by spinal cord proinflammatory cytokines. The Journal of neuroscience: the official journal of the Society for Neuroscience 2001; 21(8):2808-2819.

[52] Mintz I M, Venema V J, Swiderek K M, Lee T D, Bean B P, Adams M E. P-type calcium channels blocked by the spider toxin omega-Aga-IVA. Nature 1992; 355(6363): 827-829.

[53] Moutal A, Chew L A, Yang X, Wang Y, Yeon S K, Telemi E, Meroueh S, Park K D, Shrinivasan R, Gilbraith K B, Qu C, Xie J Y, Patwardhan A, Vanderah T W, Khanna M, Porreca F, Khanna R. (S)-lacosamide inhibition of CRMP2 phosphorylation reduces postoperative and neuropathic pain behaviors through distinct classes of sensory neurons identified by constellation pharmacology. Pain 2016; 157(7):1448-1463.

[54] Moutal A, Li W, Wang Y, Ju W, Luo S, Cai S, Francois-Moutal L, Perez-Miller S, Hu J, Dustrude E T, Vanderah T W, Gokhale V, Khanna M, Khanna R. Homology-guided mutational analysis reveals the functional requirements for antinociceptive specificity of collapsin response mediator protein 2-derived peptides. British journal of pharmacology 2017.

[55] Moutal A, Wang Y, Yang X, Ji Y, Luo S, Dorame A, Bellampalli S S, Chew L A, Cai S, Dustrude E T, Keener J E, Marty M T, Vanderah T W, Khanna R. Dissecting the role of the CRMP2-neurofibromin complex on pain behaviors. Pain 2017; 158(11):2203-2221.

[56] Newcomb R, Szoke B, Palma A, Wang G, Chen X, Hopkins W, Cong R, Miller J, Urge L, Tarczy-Hornoch K, Loo J A, Dooley D J, Nadasdi L, Tsien R W, Lemos J, Miljanich G. Selective peptide antagonist of the class E calcium channel from the venom of the tarantula *Hysterocrates gigas*. Biochemistry 1998; 37(44):15353-15362.

[57] Newshan G. HIV neuropathy treated with gabapentin. AIDS 1998; 12(2):219-221.

[58] Okubo K, Takahashi T, Sekiguchi F, Kanaoka D, Matsunami M, Ohkubo T, Yamazaki J, Fukushima N, Yoshida S, Kawabata A. Inhibition of T-type calcium channels and hydrogen sulfide-forming enzyme reverses paclitaxel-evoked neuropathic hyperalgesia in rats. Neuroscience 2011; 188:148-56. Epub;%2011 May 11.:148-156.

[59] Olson K M, Duron D I, Womer D, Fell R, Streicher J M. Comprehensive molecular pharmacology screening reveals potential new receptor interactions for clinically relevant opioids. PloS one 2019; 14(6):e0217371.

[60] Polomano R C, Mannes A J, Clark U S, Bennett G J. A painful peripheral neuropathy in the rat produced by the chemotherapeutic drug, paclitaxel. Pain 2001; 94(3):293-304.

[61] Reid C A, Clements J D, Bekkers J M. Nonuniform distribution of $Ca^{2+}$ channel subtypes on presynaptic terminals of excitatory synapses in hippocampal cultures. JNeurosci 1997; 17(8):2738-2745.

[62] Rettig J, Sheng Z H, Kim D K, Hodson C D, Snutch T P, Catterall W A. Isoform-specific interaction of the alphaIA subunits of brain $Ca^{2+}$ channels with the presynaptic proteins syntaxin and SNAP-25. ProcNatlAcadSciUSA 1996; 93(14):7363-7368.

[63] Rose K E, Lunardi N, Boscolo A, Dong X, Erisir A, Jevtovic-Todorovic V, Todorovic S M. Immunohistological demonstration of CaV3.2 T-type voltage-gated calcium channel expression in soma of dorsal root ganglion neurons and peripheral axons of rat and mouse. Neuroscience 2013; 250:263-274.

[64] Scroggs R S, Fox A P. Calcium current variation between acutely isolated adult rat dorsal root ganglion neurons of different size. JPhysiol 1992; 445:639-58.: 639-658.

[65] Sekiguchi F, Kawara Y, Tsubota M, Kawakami E, Ozaki T, Kawaishi Y, Tomita S, Kanaoka D, Yoshida S, Ohkubo T, Kawabata A. Therapeutic potential of RQ-00311651, a novel T-type Ca2+ channel blocker, in distinct rodent models for neuropathic and visceral pain. Pain 2016; 157(8):1655-1665.

[66] Sheng Z H, Rettig J, Cook T, Catterall W A. Calcium-dependent interaction of N-type calcium channels with the synaptic core complex. Nature 1996; 379(6564):451-454.

[67] Shin J B, Martinez-Salgado C, Heppenstall P A, Lewin G R. A T-type calcium channel required for normal function of a mammalian mechanoreceptor. NatNeurosci 2003; 6(7):724-730.

[68] Snider W D, McMahon S B. Tackling pain at the source: new ideas about nociceptors. Neuron 1998; 20(4): 629-632.

[69] Snutch T P, Zamponi G W. Recent advances in the development of T-type calcium channel blockers for pain intervention. British journal of pharmacology 2017.

[70] Staff N P, Fehrenbacher J C, Caillaud M, Damaj M I, Segal R A, Rieger S. Pathogenesis of paclitaxel-induced peripheral neuropathy: A current review of in vitro and in vivo findings using rodent and human model systems. Exp Neurol 2019; 324:113121.

[71] Stemkowski P, Garcia-Caballero A, Gadotti V M, M'Dahoma S, Huang S, Black S A, Chen L, Souza I A, Zhang Z, Zamponi G W. TRPV1 Nociceptor Activity Initiates USP5/T-type Channel-Mediated Plasticity. Cell Rep 2016; 17(11):2901-2912.

[72] Stepan A F, Walker D P, Bauman J, Price D A, Baillie T A, Kalgutkar A S, Aleo M D. Structural Alert/Reactive Metabolite Concept as Applied in Medicinal Chemistry to Mitigate the Risk of Idiosyncratic Drug Toxicity: A Perspective Based on the Critical Examination of Trends in the Top 200 Drugs Marketed in the United States. Chem Res Toxicol 2011; 24(9):1345-1410.

[73] Stucky C L, Lewin G R. Isolectin B(4)-positive and -negative nociceptors are functionally distinct. The Journal of neuroscience: the official journal of the Society for Neuroscience 1999; 19(15):6497-6505.

[74] Takahashi T, Aoki Y, Okubo K, Maeda Y, Sekiguchi F, Mitani K, Nishikawa H, Kawabata A. Upregulation of Ca(v)3.2 T-type calcium channels targeted by endogenous hydrogen sulfide contributes to maintenance ofneuropathic pain. Pain 2010; 150(1):183-191.

[75] Teichert R W, Memon T, Aman J W, Olivera B M. Using constellation pharmacology to define comprehensively a somatosensory neuronal subclass. Proceedings of the National Academy of Sciences of the United States of America 2014; 111(6):2319-2324.

[76] Teichert R W, Schmidt E W, Olivera B M. Constellation pharmacology: a new paradigm for drug discovery. Annual review of pharmacology and toxicology 2015; 55:573-589.

[77] Teleb M, Zhang F X, Huang J, Gadotti V M, Farghaly A M, AboulWafa OM, Zamponi G W, Fahmy H. Synthesis and biological evaluation of novel N3-substituted dihydropyrimidine derivatives as T-type calcium channel blockers and their efficacy as analgesics in mouse models of inflammatory pain. Bioorganic & medicinal chemistry 2017; 25(6):1926-1938.

[78] Todorovic S M, Jevtovic-Todorovic V. T-type voltage-gated calcium channels as targets for the development of novel pain therapies. British journal of pharmacology 2011; 163(3):484-495.

[79] Todorovic S M, Jevtovic-Todorovic V. Neuropathic pain: role for presynaptic T-type channels in nociceptive signaling. Pflugers Archiv: European journal of physiology 2013; 465(7):921-927.

[80] Tringham E, Powell K L, Cain S M, Kuplast K, Mezeyova J, Weerapura M, Eduljee C, Jiang X, Smith P, Morrison J L, Jones N C, Braine E, Rind G, Fee-Maki M, Parker D, Pajouhesh H, Parmar M, O'Brien T J, Snutch T P. T-type calcium channel blockers that attenuate thalamic burst firing and suppress absence seizures. Science translational medicine 2012; 4(121):121ra119.

[81] Waxman S G, Zamponi G W. Regulating excitability of peripheral afferents: emerging ion channel targets. Nature neuroscience 2014; 17(2):153-163.

[82] Webster L R, Fakata K L, Charapata S, Fisher R, MineHart M. Open-label, multicenter study of combined intrathecal morphine and ziconotide: addition of morphine in patients receiving ziconotide for severe chronic pain. Pain Med 2008; 9(3):282-290.

[83] Weiss N, Black S A, Bladen C, Chen L, Zamponi G W. Surface expression and function of Cav3.2 T-type calcium channels are controlled by asparagine-linked glycosylation. Pflugers Archiv: European journal of physiology 2013; 465(8):1159-1170.

[84] Weiss N, Hameed S, Fernandez-Femandez J M, Fablet K, Karmazinova M, Poillot C, Proft J, Chen L, Bidaud I, Monteil A, Huc-Brandt S, Lacinova L, Lory P, Zamponi G W, De Waard M. A Ca(v)3.2/syntaxin-TA signaling complex controls T-type channel activity and low-threshold exocytosis. The Journal of biological chemistry 2012; 287(4):2810-2818.

[85] Weiss N, Zamponi G W. Control of low-threshold exocytosis by T-type calcium channels. Biochimica et biophysica acta 2012.

[86] Wen X J, Xu S Y, Chen Z X, Yang C X, Liang H, Li H. The roles of T-type calcium channel in the development of neuropathic pain following chronic compression of rat dorsal root ganglia. Pharmacology 2010; 85(5):295-300.

[87] Xiao W, Naso L, Bennett G J. Experimental studies of potential analgesics for the treatment of chemotherapy-evoked painful peripheral neuropathies. Pain Med 2008; 9(5):505-517.

[88] Xie J Y, Chew L A, Yang X, Wang Y, Qu C, Wang Y, Federici L M, Fitz S D, Ripsch M S, Due M R, Moutal A, Khanna M, White F A, Vanderah T W, Johnson P L, Porreca F, Khanna R. Sustained relief of ongoing experimental neuropathic pain by a CRMP2 peptide aptamer with low abuse potential. Pain 2016; 157(9):2124-2140.

[89] Yaksh T L, Rudy T A. Chronic catheterization of the spinal subarachnoid space. Physiology & behavior 1976; 17(6):1031-1036.

[90] Yu J, Moutal A, Dorame A, Bellampalli S S, Chefdeville A, Kanazawa I, Pham N Y N, Park K D, Weimer J M, Khanna R. Phosphorylated CRMP2 Regulates Spinal Nociceptive Neurotransmission. Molecular neurobiology 2018.

[91] Yuan S B, Shi Y, Chen J, Zhou X, Li G, Gelman B B, Lisinicchia J G, Carlton S M, Ferguson M R, Tan A, Sarna S K, Tang S J. Gp120 in the pathogenesis of human immunodeficiency virus-associated pain. Annals of neurology 2014; 75(6):837-850.

[92] Yue J, Liu L, Liu Z, Shu B, Zhang Y. Upregulation of T-type Ca$^{2+}$ channels in primary sensory neurons in spinal nerve injury. Spine (Phila Pa 1976) 2013; 38(6):463-470.

[93] Zhang J, Hu Y, Foley C, Wang Y, Musharrafieh R, Xu S, Zhang Y, Ma C, Hulme C, Wang J. Exploring Ugi-Azide Four-Component Reaction Products for Broad-Spectrum Influenza Antivirals with a High Genetic Barrier to Drug Resistance. Sci Rep 2018; 8(1):4653.

[94] Zhao Y, Huang G, Wu Q, Wu K, Li R, Lei J, Pan X, Yan N. Cryo-E M structures of apo and antagonist-bound human Cav3.1. Nature 2019.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound encompassed within:

including pharmaceutically acceptable salts, and/or solvates thereof, wherein R1 is selected from

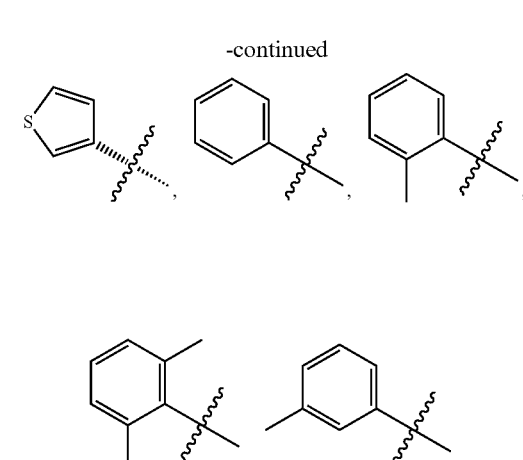

-continued

-continued wherein R2 is selected from

-continued wherein R3 is selected from

2. The compound of claim 1, wherein the compound is selected from the group consisting of:

115

116

-continued

117

-continued

118

119

-continued

120

-continued

121

-continued

122

-continued

123

-continued 2-197-2

2-203-2

2-203-1

2-145-1

124

-continued 3-32-1

3-32-3

3-32-2

3-32-5

125

-continued 3-32-6

3-10-1

3-10-3

3-32-4

126

-continued 3-8-2

3-8-3

3-32-8

3-8-1

127

-continued 3-9-1

3-32-9

3-1-1

3-13-1

128

-continued 3-13-2

3-13-3

3-14-2

3-14-3

129
-continued

130
-continued 3-5-2

2-199-2

3-6-2

2-183-1

3-25

3-4-2

1-159-2

1-157-2

1-157-1

2-143-2

2-193-1

3. The compound of claim 1, wherein the compound is encompassed with a pharmaceutical composition.

4. A method of treating, ameliorating, or preventing a condition related to pan-T-type activity or CaV3.2 activity in a patient comprising administering to said patient a therapeutically effective amount of the pharmaceutical composition of claim 3, wherein said condition related to pan-T-type activity or CaV3.2 activity is one or more of pain related to general neuropathy; pain related to diabetes related neuropathy; pain related to HIV-associated peripheral sensory neuropathy; pain related to chemotherapy-induced peripheral neuropathy (CIPN); pain related to spinal nerve ligation (SNL) induced neuropathy, and pain related to pan-T-type activity or CaV3.2 activity.

5. The method of claim 4, wherein said patient is a human patient.

6. The method of claim 4, further comprising administering to said patient one or more agents for treating pain.

7. A method for inhibiting pan-T-type related activity or CaV3.2 related activity in a subject, comprising administering to the subject a compound of claim 1, wherein administration of the compound results in one or more of the following in the subject:

inhibiting depolarization-induced calcium influx related to pan-T-type voltage gated calcium channel activity;

inhibiting depolarization-induced calcium influx related to CaV3.2 voltage gated calcium channel activity;

inhibiting, preventing and/or ameliorating neuropathy pain related to pan-T-type activity inhibiting, preventing and/or ameliorating neuropathy pain related to CaV3.2 activity;

inhibiting, preventing and/or ameliorating pain related to pan-T-type activity;

inhibiting, preventing and/or ameliorating pain related to CaV3.2 activity;

inhibiting, preventing and/or ameliorating pain related to HIV-associated peripheral sensory neuropathy;

inhibiting, preventing and/or ameliorating pain related to chemotherapy-induced peripheral neuropathy (CIPN);

inhibiting, preventing and/or ameliorating pain related to spinal nerve ligation (SNL) induced neuropathy;

inhibiting, preventing and/or ameliorating tonic, neuropathic, and/or inflammatory pain;

inhibiting spontaneous excitatory post-synaptic currents via actions presynaptically; and inhibiting release of the pronociceptive neurotransmitter calcitonin gene related peptide (CGRP).

8. The method of claim 7, wherein the subject is human subject suffering from or at risk from pain related to pan-T-type activity or CaV3.2 activity.

9. A compound selected from the group consisting of:

134

135

-continued

136

137
-continued

138
-continued

139

140

141
-continued

142
-continued 2-197-2

3-32-1

2-203-2

3-32-3

3-32-2

2-203-1  35

2-145-1

3-32-5

143                                                          144
-continued                                                  -continued 3-32-6                                                      3-8-2

3-10-1                                                      3-8-3

3-10-3                                                      3-32-8

50                                                          3-8-1

3-32-4

145

-continued 3-9-1

146

-continued 3-13-2

3-32-9

3-13-3

3-1-1

3-14-2

3-13-1

3-14-3

147
-continued

148
-continued 3-5-2

2-199-2

3-6-2

2-183-1

3-25

3-4-2

1-159-2

| 149 | 150 |
|---|---|
| -continued | -continued |

1-157-2

2-193-2

2-193-1

1-157-1

2-201-2

2-143-2 and

3-3-2

\*  \*  \*  \*  \*